United States Patent
Takahashi et al.

(10) Patent No.: US 9,657,310 B2
(45) Date of Patent: *May 23, 2017

(54) EXPRESSION VECTOR

(71) Applicant: JCR Pharmaceuticals Co., Ltd., Hyogo (JP)

(72) Inventors: Kenichi Takahashi, Hyogo (JP); Shinji Kakimoto, Hyogo (JP)

(73) Assignee: JCR PHARMACEUTICALS CO., LTD., Ashiya-Shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/396,929

(22) PCT Filed: Apr. 25, 2013

(86) PCT No.: PCT/JP2013/062251
§ 371 (c)(1),
(2) Date: Mar. 10, 2015

(87) PCT Pub. No.: WO2013/161958
PCT Pub. Date: Oct. 31, 2013

(65) Prior Publication Data
US 2015/0337331 A1    Nov. 26, 2015

(30) Foreign Application Priority Data
Apr. 27, 2012  (JP) ................. 2012-102796

(51) Int. Cl.
*C12N 15/00*    (2006.01)
*C12N 9/00*    (2006.01)
(Continued)

(52) U.S. Cl.
CPC ............ *C12N 15/85* (2013.01); *C07K 14/505* (2013.01); *C07K 14/59* (2013.01);
(Continued)

(58) Field of Classification Search
None
See application file for complete search history.

(56) References Cited

U.S. PATENT DOCUMENTS 5,770,359 A    6/1998    Wilson et al.
8,809,017 B2*  8/2014    Yang ............... C12P 21/02
                                          435/320.1

(Continued)

FOREIGN PATENT DOCUMENTS

CN    102321668    1/2012
CN    102409060    4/2012

(Continued)

OTHER PUBLICATIONS

Orlinger et al. "Selection and Analysis of Mutations in an Encephalomyocarditis Virus Internal Ribosome Entry Site That Improve the Efficiency of a Bicistrionic Flavivirus Construct," Journal of Virology, vol. 81, No. 22: 12619-12629 (2007).*

(Continued)

Primary Examiner — Janet L Andres
Assistant Examiner — M. Franco Salvoza
(74) Attorney, Agent, or Firm — Hamre, Schumann, Mueller & Larson, P.C.

(57) ABSTRACT

Disclosed are a novel expression vector for efficient expression of recombinant proteins in mammalian cells, a mammalian cell transformed with the vector, and a method for production of the mammalian cell. The expression vector is an expression vector for expression of a mammalian protein and includes a gene expression regulatory site, and a gene encoding the protein downstream thereof, and an internal ribosome entry site further downstream thereof, and a gene encoding a glutamine synthetase further downstream thereof, and a dihydrofolate reductase gene downstream of (Continued)

either the same gene expression regulatory site or another gene expression regulatory site in addition to the former.

16 Claims, 27 Drawing Sheets

(51) Int. Cl.
    *C12N 15/85* (2006.01)
    *C12N 15/52* (2006.01)
    *C12N 9/06* (2006.01)
    *C07K 14/59* (2006.01)
    *C07K 14/505* (2006.01)
    *C07K 16/28* (2006.01)

(52) U.S. Cl.
    CPC .......... *C07K 16/2887* (2013.01); *C12N 9/003* (2013.01); *C12N 9/93* (2013.01); *C12N 15/52* (2013.01); *C07K 2317/14* (2013.01); *C12N 2800/107* (2013.01); *C12N 2830/00* (2013.01); *C12N 2830/42* (2013.01); *C12N 2830/50* (2013.01); *C12N 2830/60* (2013.01); *C12N 2840/60* (2013.01); *C12Y 105/01003* (2013.01); *C12Y 603/01002* (2013.01)

(56) References Cited

U.S. PATENT DOCUMENTS

| | | | | |
|---|---|---|---|---|
| 2007/0065912 A1* | 3/2007 | Carson | .................. | C07K 16/00 435/69.1 |
| 2011/0105734 A1* | 5/2011 | Kawasaki | ............ | C07K 14/505 530/397 |
| 2013/0244231 A1* | 9/2013 | Takahashi | .............. | C12N 15/67 435/6.1 |

FOREIGN PATENT DOCUMENTS

| | | |
|---|---|---|
| JP | 63-502955 | 11/1988 |
| JP | 08-256776 | 10/1996 |
| JP | 10-327871 | 12/1998 |
| JP | 2009-273427 | 11/2009 |
| WO | WO 0066758 | * 11/2000 |
| WO | 2005/040364 | 5/2005 |
| WO | 2012/063799 | 5/2012 |

OTHER PUBLICATIONS

Skarnes et al. "A conditional knockout resource for the genome-wide study of mouse gene function," Nature 474(7351): 337-342 (2011).*

International Search Report of PCT/JP2013/062251, dated Jul. 30, 2013, 4 pages total.

Martin et al., "Development of a new bicistronic retroviral vector with strong IRES activity," BMC Biotechnol., 2006, vol. 6, No. 4, pp. 1-9.

Cacciatore et al., "Gene amplification and vector engineering to achieve rapid and high-level therapeutic protein production using the Dhfr-based CHO cell selection system," Biotechnol. Adv., 2010, vol. 28, No. 6, pp. 673-681.

Wang et al., "Dual gene amplification and selection system with dihydrofolate reductase and glutamine synthetase genes effectively increase the foreign gene expression," Chinese J. Exp. Clin. Virol., 2002, vol. 16, No. 6, pp. 59-61 (English language abstract provided).

Kaufman et al., "Construction of a modular dihydrofolate reductase cDNA gene: analysis of signals utilized for efficient expression," Molecular and Cellular Biology, 1982, vol. 2, No. 11, pp. 1304-1319.

International Preliminary Report on Patentability for PCT/JP2013/062251, dated Oct. 14, 2014, 10 pages total.

Pu, H. et al., "Rapid Establishment of High-Producing Cell Lines Using Dicistronic Vectors with Glutamine Synthetase as the Selection Marker," Molecular Biotechnology, vol. 10, p. 17-25, 1998, 9 pages.

Trouet et al., "Use of bicistronic GFP-expression vector to characterise ion channels after transfection in mammalian cells," Springer-Verlag 1997, Eur J Physiol, vol. 434, p. 632-638, 7 pages.

Havenga, M.J.E. et al., "Second gene expression in bicistronic constructs using short synthetic intercistrons and viral IRES sequences," Gene 222 (1998) 319-327, An International Journal on Genes and Genomes, 9 pages.

Van Blokland, H.J.M. et al., "A novel, high stringency selection system allows screening of few clones for high protein expression," ScienceDirect Journal of Biotechnology 128 (2007) 237-245, 9 pages.

Davies, M.V. et al., "The Sequence Context of the Initiation Codon in the Encephalomycarditis Virus Leader Modulates Efficiency of Internal Translation Initiation," Journal of Virology, Apr. 1992, p. 1924-1932, American Society for Microbiology, vol. 66, No. 4, 9 pages.

Bochkov, Y. A. et al., "Translational efficiency of EMCV IRES in bicistronic vectors is dependent upon IRES sequence and gene location," www.biotechniques.com, Bio Techniques, vol. 41, p. 283-292, No. 3, 2006, 5 pages.

Meng, Y.G. et al., "Green fluorescent protein as a second selectable marker for selection of high producing clones from transfected CHO cells," Gene 242 (2000) 201-207, An International Journal on Genes, Genomes and Evolution, 7 pages.

Wirth, M. et al., "Isolation of overproducing recombinant mammalian cell lines by a fast and simple selection procedure," Gene, vol. 73 (1988) 419-426, Elsevier, GEN 02795, 8 pages.

* cited by examiner

SEQUENCE LISTING

<160> NUMBER OF SEQ ID NOS: 59

<210> SEQ ID NO 1
<211> LENGTH: 23
<212> TYPE: DNA
<213> ORGANISM: Murine endogenous retrovirus

<400> SEQUENCE: 1
atgataatat ggccacaacc atg                    23

```
<210> SEQ ID NO 2
<211> LENGTH: 23
<212> TYPE: DNA
<213> ORGANISM: Artificial Sequence
<220> FEATURE:
<223> OTHER INFORMATION: Modified murine encephalomyocarditis virus
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 2
atgataatnn ngccacaacc nnn                                       23

<210> SEQ ID NO 3
<211> LENGTH: 23
<212> TYPE: DNA
<213> ORGANISM: Artificial Sequence
<220> FEATURE:
<223> OTHER INFORMATION: Modified murine encephalomyocarditis virus
<220> FEATURE:
<221> NAME/KEY: misc_feature
<222> LOCATION: (9)..(11)
<223> OTHER INFORMATION: n is a, c, g, or t

<400> SEQUENCE: 3
atgataatnn ngccacaacc atg                                       23

<210> SEQ ID NO 4
<211> LENGTH: 23
<212> TYPE: DNA
<213> ORGANISM: Artificial Sequence
<220> FEATURE:
<223> OTHER INFORMATION: Modified murine encephalomyocarditis virus

<400> SEQUENCE: 4
atgataagct tgccacaacc atg                                       23

<210> SEQ ID NO 5
<211> LENGTH: 596
<212> TYPE: DNA
<213> ORGANISM: Murine endogenous retrovirus

<400> SEQUENCE: 5
cccccccccc tctccctccc cccccctaa  cgttactggc cgaagccgct tggaataagg   60
ccggtgtgcg tttgtctata tgttattttc caccatattg ccgtcttttg gcaatgtgag  120
ggcccggaaa cctggccctg tcttcttgac gagcattcct aggggtcttt ccctctcgc   180 caaaggaatg caaggtctgt tgaatgtcgt gaaggaagca gttcctctgg aagcttcttg  240
aagacaaaca acgtctgtag cgaccctttg caggcagcgg aaccccccac ctggcgacag  300
gtgcctctgc ggccaaaagc cacgtgtata agatacacct gcaaaggcgg cacaacccca  360
gtgccacgtt gtgagttgga tagttgtgga aagagtcaaa tggctctcct caagcgtatt  420
caacaagggg ctgaaggatg cccagaaggt accccattgt atgggatctg atctggggcc  480
tcggtgcaca tgctttacat gtgtttagtc gaggttaaaa aaacgtctag gccccccgaa  540
ccacggggac gtggttttcc tttgaaaaac acgatgataa tatggccaca accatg      596

<210> SEQ ID NO 6
```

<211> LENGTH: 596
<212> TYPE: DNA
<213> ORGANISM: Artificial Sequence
<220> FEATURE:
<223> OTHER INFORMATION: Modified murine encephalomyocarditis virus

<400> SEQUENCE: 6

```
cccccccccc tctccctccc ccccccctaa cgttactggc cgaagccgct tggaata

| | | |
|---|---|---|
| att ggc aag aac gga gac cta ccc tgg cct ccg ctc agg aac gag ttc<br>Ile Gly Lys Asn Gly Asp Leu Pro Trp Pro Pro Leu Arg Asn Glu Phe<br>             20                        25                        30 | | 96 |
| aag tac ttc caa aga atg acc aca acc tct tca gtg gaa ggt aaa cag<br>Lys Tyr Phe Gln Arg Met Thr Thr Thr Ser Ser Val Glu Gly Lys Gln<br>             35                        40                        45 | | 144 |
| aat ctg gtg att atg ggt agg aaa acc tgg ttc tcc att cct gag aag<br>Asn Leu Val Ile Met Gly Arg Lys Thr Trp Phe Ser Ile Pro Glu Lys<br> 50                        55                        60 | | 192 |
| aat cga cct tta aag gac aga att aat ata gtt ctc agt aga gaa ctc<br>Asn Arg Pro Leu Lys Asp Arg Ile Asn Ile Val Leu Ser Arg Glu Leu<br>65                    70                        75                        80 | | 240 |
| aaa gaa cca cca cga gga gct cat ttt ctt gcc aaa agt ttg gat gat<br>Lys Glu Pro Pro Arg Gly Ala His Phe Leu Ala Lys Ser Leu Asp Asp<br>                       85                        90                        95 | | 288 |
| gcc tta aga ctt att gaa caa ccg gaa ttg gca agt aaa gta gac atg<br>Ala Leu Arg Leu Ile Glu Gln Pro Glu Leu Ala Ser Lys Val Asp Met<br>             100                     105                      110 | | 336 |
| gtt tgg ata gtc gga ggc agt tct gtt tac cag gaa gcc atg aat caa<br>Val Trp Ile Val Gly Gly Ser Ser Val Tyr Gln Glu Ala Met Asn Gln<br>             115                     120                      125 | | 384 |
| cca ggc cac ctt aga ctc ttt gtg aca agg atc atg cag gaa ttt gaa<br>Pro Gly His Leu Arg Leu Phe Val Thr Arg Ile Met Gln Glu Phe Glu<br> 130                       135                        140 | | 432 |
| agt gac acg ttt ttc cca gaa att gat ttg ggg aaa tat aaa ctt ctc<br>Ser Asp Thr Phe Phe Pro Glu Ile Asp Leu Gly Lys Tyr Lys Leu Leu<br>145                    150                        155                        160 | | 480 |
| cca gaa tac cca ggc gtc ctc tct gag gtc cag gag gaa aaa ggc atc<br>Pro Glu Tyr Pro Gly Val Leu Ser Glu Val Gln Glu Glu Lys Gly Ile<br>             165                     170                      175 | | 528 |
| aag tat aag ttt gaa gtc tac gag aag aaa gac taa<br>Lys Tyr Lys Phe Glu Val Tyr Glu Lys Lys Asp<br>             180                     185 | | 564 |

```
<210> SEQ ID NO 10
<211> LENGTH: 187
<212> TYPE: PRT
<213> ORGANISM: Mus musculus

<400> SEQUENCE: 10
```

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 11
<211> LENGTH: 564
<212> TYPE: DNA
<213> ORGANISM: Artificial Sequence
<220> FEATURE:
<223> OTHER INFORMATION: Modified Mus musculus DHFR
<220> FEATURE:
<221> NAME/KEY: CDS
<222> LOCATION: (1)..(564)

<400> SEQUENCE: 11

```
atg gtt cga cca ttg aac tgc atc gtc gcc gtg tcc caa aat atg ggg      48
Met Val Arg Pro Leu Asn Cys Ile Val Ala Val Ser Gln Asn Met Gly
1               5                   10                  15 att ggc aag aac gga gac cta ccc tgg cct ccg ctc agg aac gag tgg      96
Ile Gly Lys Asn Gly Asp Leu Pro Trp Pro Pro Leu Arg Asn Glu Trp
            20                  25                  30 aag tac ttc caa aga atg acc aca acc tct tca gtg gaa ggt aaa cag     144
Lys Tyr Phe Gln Arg Met Thr Thr Thr Ser Ser Val Glu Gly Lys Gln
        35                  40                  45 aat ctg gtg att atg ggt agg aaa acc tgg ttc tcc att cct gag aag     192
Asn Leu Val Ile Met Gly Arg Lys Thr Trp Phe Ser Ile Pro Glu Lys
    50                  55                  60 aat cga cct tta aag gac aga att aat ata gtt ctc agt aga gaa ctc     240
Asn Arg Pro Leu Lys Asp Arg Ile Asn Ile Val Leu Ser Arg Glu Leu
65                  70                  75                  80 aaa gaa cca cca cga gga gct cat ttt ctt gcc aaa agt ttg gat gat     288
Lys Glu Pro Pro Arg Gly Ala His Phe Leu Ala Lys Ser Leu Asp Asp
                85                  90                  95 gcc tta aga ctt att gaa caa ccg gaa ttg gca agt aaa gta gac atg     336
Ala Leu Arg Leu Ile Glu Gln Pro Glu Leu Ala Ser Lys Val Asp Met
            100                 105                 110 gtt tgg ata gtc gga ggc agt tct gtt tac cag gaa gcc atg aat caa     384
Val Trp Ile Val Gly Gly Ser Ser Val Tyr Gln Glu Ala Met Asn Gln
        115                 120                 125 cca ggc cac ctt aga ctc ttt gtg aca agg atc atg cag gaa ttt gaa     432
Pro Gly His Leu Arg Leu Phe Val Thr Arg Ile Met Gln Glu Phe Glu
    130                 135                 140 agt gac acg ttt ttc cca gaa att gat ttg ggg aaa tat aaa ctt ctc     480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc     528
Pro Glu Tyr Pro Gly Val Leu Ser Glu Val Gln Glu Glu Lys Gly Ile
                165                 170                 175 aag tat aag ttt gaa gtc tac gag aag aaa gac taa                     564
Lys Tyr Lys Phe Glu Val Tyr Glu Lys Lys Asp
            180                 185
```

<210> SEQ ID NO 12
<211> LENGTH: 187
<212> TYPE: PRT
<213> ORGANISM: Artificial Sequence
<220> FEATURE:
<223> OTHER INFORMATION: Synthetic Construct

<400> SEQUENCE: 12

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Trp
                20                  25                  30

Lys Tyr Phe Gln Arg Met Thr Thr Thr Ser Ser Val Glu Gly Lys Gln
            35                  40                  45

Asn Leu Val Ile Met Gly Arg Lys Thr Trp Phe Ser Ile Pro Glu Lys
        50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 13
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 13
gaggccgcct cggcctctga                                               20

<210> SEQ ID NO 14
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 14
aaccatcgtg atgggtgcta ttcctttgc                                     29

<210> SEQ ID NO 15
<211> LENGTH: 2216
<212> TYPE: DNA
<213> ORGANISM: Artificial Sequence
<220> FEATURE:
<223> OTHER INFORMATION: IRES-Hygr-mPGKpA, synthetic sequence
<220> FEATURE:
<221> NAME/KEY: CDS
<222> LOCATION: (716)..(1741)

<400> SEQUENCE: 15
ctcgaggaat tcactccttc aggtgcaggc ttgcctatca gaaggtggtg gctggtgtgg    60
ccaactggct cacaaatacc actgagatcg acgtatcga taagcttgat atcgaattcc   120 gcccccccccc cctctccctc ccccccccct aacgttactg gccgaagccg cttggaataa   180

```
ggccggtgtg cgtttgtcta tatgttattt tccaccatat tgccgtcttt tggcaatgtg    240
agggcccgga aacctggccc tgtcttcttg acgagcattc ctaggggtct ttcccctctc    300
gccaaaggaa tgcaaggtct gttgaatgtc gtgaaggaag cagttcctct ggaagcttct    360
tgaagacaaa caacgtctgt agcgacccct tgcaggcagc ggaacccccc acctggcgac    420
aggtgcctct gcggccaaaa gccacgtgta taagatacac ctgcaaaggc ggcacaaccc    480
cagtgccacg ttgtgagttg gatagttgtg gaaagagtca atggctctc ctcaagcgta    540 ttcaacaagg ggctgaagga tgcccagaag gtaccccatt gtatgggatc tgatctgggg    600
cctcggtgca catgctttac atgtgtttag tcgaggttaa aaaaacgtct aggccccccg    660
aaccacgggg acgtggtttt cctttgaaaa acacgatgat aatatggcca caacc atg    718
                                                              Met
                                                              1
```

```
aaa aag cct gaa ctc acc gcg acg tct gtc gag aag ttt ctg atc gaa    766
Lys Lys Pro Glu Leu Thr Ala Thr Ser Val Glu Lys Phe Leu Ile Glu
        5                  10                 15 aag ttc gac agc gtc tcc gac ctg atg cag ctc tcg gag ggc gaa gaa    814
Lys Phe Asp Ser Val Ser Asp Leu Met Gln Leu Ser Glu Gly Glu Glu
            20                 25                 30 tct cgt gct ttc agc ttc gat gta gga ggg cgt gga tat gtc ctg cgg    862
Ser Arg Ala Phe Ser Phe Asp Val Gly Gly Arg Gly Tyr Val Leu Arg
    35                 40                 45 gta aat agc tgc gcc gat ggt ttc tac aaa gat cgt tat gtt cat cgg    910
Val Asn Ser Cys Ala Asp Gly Phe Tyr Lys Asp Arg Tyr Val His Arg
50                  55                 60                 65 cac ttt gca tcg gcc gcg ctc ccg att ccg gaa gtg ctt gac att ggg    958
His Phe Ala Ser Ala Ala Leu Pro Ile Pro Glu Val Leu Asp Ile Gly
                70                 75                 80 gaa ttc agc gag agc ctg acc tat tgc atc tcc cgc cgt gca cag ggt   1006
Glu Phe Ser Glu Ser Leu Thr Tyr Cys Ile Ser Arg Arg Ala Gln Gly
            85                 90                 95 gtc acg ttg caa gac ctg cct gaa acc gaa ctg ccc gct gtt ctg cag   1054
Val Thr Leu Gln Asp Leu Pro Glu Thr Glu Leu Pro Ala Val Leu Gln
        100                105                110 ccg gtc gcg gag gcc atg gat gcg atc gct gcg gcc gat ctt agc cag   1102
Pro Val Ala Glu Ala Met Asp Ala Ile Ala Ala Ala Asp Leu Ser Gln
    115                120                125 acg agc ggg ttc ggc cca ttc gga ccg caa gga atc ggt caa tac act   1150
Thr Ser Gly Phe Gly Pro Phe Gly Pro Gln Gly Ile Gly Gln Tyr Thr
130                135                140                145 acg tgg cgt gat ttc ata tgc gcg att gct gat ccc cat gtg tat cac   1198
Thr Trp Arg Asp Phe Ile Cys Ala Ile Ala Asp Pro His Val Tyr His
                150                155                160 tgg caa act gtg atg gac gac acc gtc agt gcg tcc gtc gcg cag gct   1246
Trp Gln Thr Val Met Asp Asp Thr Val Ser Ala Ser Val Ala Gln Ala
            165                170                175 ctc gat gag ctg atg ctt tgg gcc gag gac tgc ccc gaa gtc cgg cac   1294
Leu Asp Glu Leu Met Leu Trp Ala Glu Asp Cys Pro Glu Val Arg His
        180                185                190 ctc gtg cac gcg gat ttc ggc tcc aac aat gtc ctg acg gac aat ggc   1342
Leu Val His Ala Asp Phe Gly Ser Asn Asn Val Leu Thr Asp Asn Gly
    195                200                205 cgc ata aca gcg gtc att gac tgg agc gag gcg atg ttc ggg gat tcc   1390
Arg Ile Thr Ala Val Ile Asp Trp Ser Glu Ala Met Phe Gly Asp Ser
210                215                220                225 caa tac gag gtc gcc aac atc ttc ttc tgg agg ccg tgg ttg gct tgt   1438
Gln Tyr Glu Val Ala Asn Ile Phe Phe Trp Arg Pro Trp Leu Ala Cys
```

-continued

```
                    230                  235                   240
atg gag cag cag acg cgc tac ttc gag cgg agg cat ccg gag ctt gca    1486
Met Glu Gln Gln Thr Arg Tyr Phe Glu Arg Arg His Pro Glu Leu Ala
                245                  250                   255 gga tcg ccg cgg ctc cgg gcg tat atg ctc cgc att ggt ctt gac caa    1534
Gly Ser Pro Arg Leu Arg Ala Tyr Met Leu Arg Ile Gly Leu Asp Gln
                260                  265                   270 ctc tat cag agc ttg gtt gac ggc aat ttc gat gat gca gct tgg gcg    1582
Leu Tyr Gln Ser Leu Val Asp Gly Asn Phe Asp Asp Ala Ala Trp Ala
            275                  280                   285 cag ggt cga tgc gac gca atc gtc cga tcc gga gcc ggg act gtc ggg    1630
Gln Gly Arg Cys Asp Ala Ile Val Arg Ser Gly Ala Gly Thr Val Gly
290                  295                  300                   305 cgt aca caa atc gcc cgc aga agc gcg gcc gtc tgg acc gat ggc tgt    1678
Arg Thr Gln Ile Ala Arg Arg Ser Ala Ala Val Trp Thr Asp Gly Cys
                310                  315                   320 gta gaa gta ctc gcc gat agt gga aac cga cgc ccc agc act cgt ccg    1726
Val Glu Val Leu Ala Asp Ser Gly Asn Arg Arg Pro Ser Thr Arg Pro
                325                  330                   335 agg gca aag gaa tag tcgagaaatt gatgatctat taagcaataa agacgtccac    1781
Arg Ala Lys Glu
            340 taaaatggaa gttttttcctg tcatactttg ttaagaaggg tgagaacaga gtacctacat  1841 tttgaatgga aggattggag ctacgggggt ggggtgggg tgggattaga taaatgcctg    1901 ctctttactg aaggctcttt actattgctt tatgataatg tttcatagtt ggatatcata   1961 atttaaacaa gcaaaccaa attaagggcc agctcattcc tccactcacg atctatagat    2021 ccactagctt ggcgtaatca tggtcatagc tgtttcctgt gtgaaattgt tatccgctca   2081 caattccaca caacatacga gccggaagca taaagtgtaa agcctggggt gcctaatgag   2141 tgagctaact cacattaatt gcgttgcgct cactgcccgc tttccagtcg ggaaacctgt   2201 cgtgccagcg gatcc                                                   2216

<210> SEQ ID NO 16
<211> LENGTH: 341
<212> TYPE: PRT
<213> ORGANISM: Artificial Sequence
<220> FEATURE:
<223> OTHER INFORMATION: Synthetic Construct

<400> SEQUENCE: 16

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val His
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125
```

```
Gln Thr Ser Gly Phe Gly Pro Phe Gly Pro Gln Gly Ile Gly Gln Tyr
        130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 17
<211> LENGTH: 53
<212> TYPE: DNA
<213> ORGANISM: Artificial Sequence
<220> FEATURE:
<223> OTHER INFORMATION: Primer IRES5', synthetic sequence

<400> SEQUENCE: 17
caactcgagc ggccgccccc cccccctctc cctccccccc ccctaacgtt act         53

<210> SEQ ID NO 18
<211> LENGTH: 22
<212> TYPE: DNA
<213> ORGANISM: Artificial Sequence
<220> FEATURE:
<223> OTHER INFORMATION: Primer IRES3', synthetic sequence

<400> SEQUENCE: 18
caagaagctt ccagaggaac tg                                            22

<210> SEQ ID NO 19
<211> LENGTH: 30
<212> TYPE: DNA
<213> ORGANISM: Artificial Sequence
<220> FEATURE:
<223> OTHER INFORMATION: Primer mPGKP5', synthetic sequence

<400> SEQUENCE: 19
gcgagatctt accgggtagg ggaggcgctt                                    30
```

<210> SEQ ID NO 20
<211> LENGTH: 30
<212> TYPE: DNA
<213> ORGANISM: Artificial Sequence
<220> FEATURE:
<223> OTHER INFORMATION: Primer mPGKP3', synthetic sequence

<400> SEQUENCE: 20
gaggaattcg atgatcggtc gaaaggcccg                                30

<210> SEQ ID NO 21
<211> LENGTH: 532
<212> TYPE: DNA
<213> ORGANISM: Artificial Sequence
<220> FEATURE:
<223> OTHER INFORMATION: mPGKp, synthetic sequence

<400> SEQUENCE: 21
gcgagatctt accgggtagg ggaggcgctt tcccaaggc agtctggagc atgcgcttta    60
gcagccccgc tgggcacttg gcgctacaca agtggcctct ggcctcgcac acattccaca   120
tccaccggta ggcgccaacc ggctccgttc tttggtggcc ccttcgcgcc accttctact   180
cctcccctag tcaggaagtt ccccccccgcc ccgcagctcg cgtcgtgcag gacgtgacaa   240
atggaagtag cacgtctcac tagtctcgtg cagatggaca gcaccgctga gcaatggaag   300
cgggtaggcc tttggggcag cggccaatag cagctttgct ccttcgcttt ctgggctcag   360
aggctgggaa ggggtgggtc cggggcggg ctcaggggcg ggctcagggg cggggcgggc    420
gcccgaaggt cctccggagg cccggcattc tgcacgcttc aaaagcgcac gtctgccgcg   480
ctgttctcct cttcctcatc tccgggcctt tcgaccgatc atcgaattcc tc          532

<210> SEQ ID NO 22
<211> LENGTH: 36
<212> TYPE: DNA
<213> ORGANISM: Artificial Sequence
<220> FEATURE:
<223> OTHER INFORMATION: Primer GS5', synthetic sequence

<400> SEQUENCE: 22
aatatggcca caaccatggc gacctcagca agttcc                         36

<210> SEQ ID NO 23
<211> LENGTH: 38
<212> TYPE: DNA
<213> ORGANISM: Artificial Sequence
<220> FEATURE:
<223> OTHER INFORMATION: Primer GS3', synthetic sequence

<400> SEQUENCE: 23
ggaggatccc tcgagttagt ttttgtattg gaagggct                       38

<210> SEQ ID NO 24
<211> LENGTH: 28
<212> TYPE: DNA
<213> ORGANISM: Artificial Sequence
<220> FEATURE:
<223> OTHER INFORMATION: Primer puro5', synthetic sequence

<400> SEQUENCE: 24
gcttaagatg accgagtaca agcccacg                                  28

<210> SEQ ID NO 25
<211> LENGTH: 30

<212> TYPE: DNA
<213> ORGANISM: Artificial Sequence
<220> FEATURE:
<223> OTHER INFORMATION: Primer puro3', synthetic sequence

<400> SEQUENCE: 25
cccatcgtga tggtcaggca ccgggcttgc                                           30

<210> SEQ ID NO 26
<211> LENGTH: 620
<212> TYPE: DNA
<213> ORGANISM: Artificial Sequence
<220> FEATURE:
<223> OTHER INFORMATION: Synthetic sequence containing puromycin
      resistance gene
<220> FEATURE:
<221> NAME/KEY: CDS
<222> LOCATION: (8)..(607)

<400> SEQUENCE: 26

```
gcttaag atg acc gag tac aag ccc acg gtg cgc ctc gcc acc cgc gac          49
        Met Thr Glu Tyr Lys Pro Thr Val Arg Leu Ala Thr Arg Asp
        1               5                   10 gac gtc ccc agg gcc gta cgc acc ctc gcc gcc gcg ttc gcc gac tac          97
Asp Val Pro Arg Ala Val Arg Thr Leu Ala Ala Ala Phe Ala Asp Tyr
15                  20                  25                  30 ccc gcc acg cgc cac acc gtc gat ccg gac cgc cac atc gag cgg gtc         145
Pro Ala Thr Arg His Thr Val Asp Pro Asp Arg His Ile Glu Arg Val
                35                  40                  45 acc gag ctg caa gaa ctc ttc ctc acg cgc gtc ggg ctc gac atc ggc         193
Thr Glu Leu Gln Glu Leu Phe Leu Thr Arg Val Gly Leu Asp Ile Gly
            50                  55                  60 aag gtg tgg gtc gcg gac gac ggc gcc gcg gtg gcg gtc tgg acc acg         241
Lys Val Trp Val Ala Asp Asp Gly Ala Ala Val Ala Val Trp Thr Thr
65                  70                  75 ccg gag agc gtc gaa gcg ggg gcg gtg ttc gcc gag atc ggc ccg cgc         289
Pro Glu Ser Val Glu Ala Gly Ala Val Phe Ala Glu Ile Gly Pro Arg
            80                  85                  90 atg gcc gag ttg agc ggt tcc cgg ctg gcc gcg cag caa cag atg gaa         337
Met Ala Glu Leu Ser Gly Ser Arg Leu Ala Ala Gln Gln Gln Met Glu
95                  100                 105                 110 ggc ctc ctg gcg ccg cac cgg ccc aag gag ccc gcg tgg ttc ctg gcc         385
Gly Leu Leu Ala Pro His Arg Pro Lys Glu Pro Ala Trp Phe Leu Ala
                115                 120                 125 acc gtc ggc gtc tcg ccc gac cac cag ggc aag ggt ctg ggc agc gcc         433
Thr Val Gly Val Ser Pro Asp His Gln Gly Lys Gly Leu Gly Ser Ala
            130                 135                 140 gtc gtg ctc ccc gga gtg gag gcg gcc gag cgc gcc ggg gtg ccc gcc         481
Val Val Leu Pro Gly Val Glu Ala Ala Glu Arg Ala Gly Val Pro Ala
145                 150                 155 ttc ctg gag acc tcc gcg ccc cgc aac ctc ccc ttc tac gag cgg ctc         529
Phe Leu Glu Thr Ser Ala Pro Arg Asn Leu Pro Phe Tyr Glu Arg Leu
            160                 165                 170 ggc ttc acc gtc acc gcc gac gtc gag gtg ccc gaa gga ccg cgc acc         577
Gly Phe Thr Val Thr Ala Asp Val Glu Val Pro Glu Gly Pro Arg Thr
175                 180                 185                 190 tgg tgc atg acc cgc aag ccc ggt gcc tga ccatcacgat ggg                  620
Trp Cys Met Thr Arg Lys Pro Gly Ala
                195
```

<210> SEQ ID NO 27
<211> LENGTH: 199
<212> TYPE: PRT

<213> ORGANISM: Artificial Sequence
<220> FEATURE:
<223> OTHER INFORMATION: Synthetic Construct

<400> SEQUENCE: 27

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Arg His Ile Glu Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 28
<211> LENGTH: 44
<212> TYPE: DNA
<213> ORGANISM: Artificial Sequence
<220> FEATURE:
<223> OTHER INFORMATION: Primer SV40polyA5', synthetic sequence

<400> SEQUENCE: 28
caacaagcgg ccgcccctcga gttcccttta gtgagggtta atgc                    44

<210> SEQ ID NO 29
<211> LENGTH: 24
<212> TYPE: DNA
<213> ORGANISM: Artificial Sequence
<220> FEATURE:
<223> OTHER INFORMATION: Primer SV40polyA3', synthetic sequence

<400> SEQUENCE: 29
cccctgaacc tgaaacataa aatg                                           24

<210> SEQ ID NO 30
<211> LENGTH: 25
<212> TYPE: DNA
<213> ORGANISM: Artificial Sequence
<220> FEATURE:
<223> OTHER INFORMATION: Primer mIRES-GS5', synthetic sequence

<400> SEQUENCE: 30

```
acacgatgat aagcttgcca caacc                                            25
```

<210> SEQ ID NO 31
<211> LENGTH: 21
<212> TYPE: DNA
<213> ORGANISM: Artificial Sequence
<220> FEATURE:
<223> OTHER INFORMATION: Primer mIRES-GS3', synthetic sequence

<400> SEQUENCE: 31

```
ctccacgata tccctgccat a                                                21
```

<210> SEQ ID NO 32
<211> LENGTH: 23
<212> TYPE: DNA
<213> ORGANISM: Artificial Sequence
<220> FEATURE:
<223> OTHER INFORMATION: Primer SV40polyA5'-2, synthetic sequence

<400> SEQUENCE: 32

```
actaactcga gttccctttta gtg                                             23
```

<210> SEQ ID NO 33
<211> LENGTH: 26
<212> TYPE: DNA
<213> ORGANISM: Artificial Sequence
<220> FEATURE:
<223> OTHER INFORMATION: Primer SV40polyA3'-2, synthetic sequence

<400> SEQUENCE: 33

```
aacggatcct tatcggattt taccac                                           26
```

<210> SEQ ID NO 34
<211> LENGTH: 18
<212> TYPE: DNA
<213> ORGANISM: Artificial Sequence
<220> FEATURE:
<223> OTHER INFORMATION: Primer mNeoA5', synthetic sequence

<400> SEQUENCE: 34

```
atcgccgtcg ggcatgcg                                                    18
```

<210> SEQ ID NO 35
<211> LENGTH: 19
<212> TYPE: DNA
<213> ORGANISM: Artificial Sequence
<220> FEATURE:
<223> OTHER INFORMATION: Primer mNeoA3', synthetic sequence

<400> SEQUENCE: 35

```
gatctcgtcg tgacccatg                                                   19
```

<210> SEQ ID NO 36
<211> LENGTH: 79
<212> TYPE: DNA
<213> ORGANISM: Artificial Sequence
<220> FEATURE:
<223> OTHER INFORMATION: Primer mNeoB5', synthetic sequence

<400> SEQUENCE: 36

```
ataatgcggc cgcaacagtc tcgaacttaa ggctagacat atgattgaac aagatggatt      60
gcacgcaggt tctgctgcc                                                   79
```

<210> SEQ ID NO 37
<211> LENGTH: 34

```
<212> TYPE: DNA
<213> ORGANISM: Artificial Sequence
<220> FEATURE:
<223> OTHER INFORMATION: Primer mNeoB3', synthetic sequence

<400> SEQUENCE: 37
ataatgcggc cgctcagaag aactcgtcaa gaag                           34

<210> SEQ ID NO 38
<211> LENGTH: 26
<212> TYPE: DNA
<213> ORGANISM: Artificial Sequence
<220> FEATURE:
<223> OTHER INFORMATION: Primer mNeoC5', synthetic sequence

<400> SEQUENCE: 38
gccttcttga cgagttcttc tgagcg                                    26

<210> SEQ ID NO 39
<211> LENGTH: 21
<212> TYPE: DNA
<213> ORGANISM: Artificial Sequence
<220> FEATURE:
<223> OTHER INFORMATION: Primer mNeoC3', synthetic sequence

<400> SEQUENCE: 39
ccatacgcgg atccttatcg c                                         21

<210> SEQ ID NO 40
<211> LENGTH: 35
<212> TYPE: DNA
<213> ORGANISM: Artificial Sequence
<220> FEATURE:
<223> OTHER INFORMATION: Primer mNeoD5', synthetic sequence

<400> SEQUENCE: 40
caacttaagt tgatgattga acaagatgga ttgca                          35

<210> SEQ ID NO 41
<211> LENGTH: 30
<212> TYPE: DNA
<213> ORGANISM: Artificial Sequence
<220> FEATURE:
<223> OTHER INFORMATION: Primer SVpA-Mega-F, synthetic sequence

<400> SEQUENCE: 41
gacgagttct tctgactcga gttccctta                                 30

<210> SEQ ID NO 42
<211> LENGTH: 42
<212> TYPE: DNA
<213> ORGANISM: Artificial Sequence
<220> FEATURE:
<223> OTHER INFORMATION: Primer SVpA-BstXI-R, synthetic sequence

<400> SEQUENCE: 42
gcagaaccac cgcggtggag atctttacca catttgtaga gg                  42

<210> SEQ ID NO 43
<211> LENGTH: 34
<212> TYPE: DNA
<213> ORGANISM: Artificial Sequence
<220> FEATURE:
<223> OTHER INFORMATION: Primer SVpA-Not-F, synthetic sequence

<400> SEQUENCE: 43
```

```
ataagaatgc ggccgcctcg agttcccttt agtg                              34
```

<210> SEQ ID NO 44
<211> LENGTH: 45
<212> TYPE: DNA
<213> ORGANISM: Artificial Sequence
<220> FEATURE:
<223> OTHER INFORMATION: Primer SVpA-BstXI-R, synthetic sequence

<400> SEQUENCE: 44

```
gcagaaccac cgcggtggtc gacgaagatc ttaccacatt tgtag                  45
```

<210> SEQ ID NO 45
<211> LENGTH: 620
<212> TYPE: DNA
<213> ORGANISM: Artificial Sequence
<220> FEATURE:
<223> OTHER INFORMATION: Synthetic sequence containing Modified
      DHFR(F31W)

<400> SEQUENCE: 45

```
tgggatatcc ttaaggctag agccaccatg gttcgaccat tgaactgcat cgtcgccgtg   60
tcccaaaata tggggattgg caagaacgga gacctaccct ggcctccgct caggaacgag  120
tggaagtact ccaaagaat gaccacaacc tcttcagtgg aaggtaaaca gaatctggtg   180
attatgggta ggaaaacctg gttctccatt cctgagaaga tcgacctttt aaggacaga   240 attaatatag ttctcagtag agaactcaaa gaaccaccac gaggagctca ttttcttgcc  300
aaaagtttgg atgatgcctt aagacttatt gaacaaccgg aattggcaag taaagtagac  360 atggttttgga tagtcggagg cagttctgtt taccaggaag ccatgaatca accaggccac  420
cttagactct ttgtgacaag gatcatgcag gaatttgaaa gtgacacgtt tttcccagaa  480
attgatttgg ggaaatataa acttctccca gaatacccag gcgtcctctc tgaggtccag  540
gaggaaaaag gcatcaagta taagtttgaa gtctacgaga agaaagacta agcgggactc  600
gagggatcac gatgggaccg                                             620
```

<210> SEQ ID NO 46
<211> LENGTH: 372
<212> TYPE: DNA
<213> ORGANISM: Artificial Sequence
<220> FEATURE:
<223> OTHER INFORMATION: Synthetic sequence containing human TSH alpha

<400> SEQUENCE: 46

```
acgcgtcgcc accatggact actaccgcaa gtacgccgcc atcttcctgg tgaccctgag   60
cgtgttcctg cacgtgctgc acagcgcccc cgacgtccag gactgccccg agtgcaccct  120
gcaggagaac cccttcttca gccagccgg cgccccatc ctgcagtgca tgggctgctg   180
cttcagccgc gcctacccca ccccctgcg cagcaagaag accatgctgg tgcagaagaa  240
cgtgaccagc gagagcacat gttgcgtggc caagagctac aaccgcgtga ccgtgatggg  300
cggcttcaag gtggagaacc acaccgcctg ccactgcagc acctgctact accacaagag  360
ctaagcggcc gc                                                     372
```

<210> SEQ ID NO 47
<211> LENGTH: 441
<212> TYPE: DNA
<213> ORGANISM: Artificial Sequence
<220> FEATURE:
<223> OTHER INFORMATION: Synthetic sequence containing human TSH beta

<400> SEQUENCE: 47

```
acgcgtcgcc accatggcaa ccgccctgtt cctgatgagc atgctgttcg gcctgacctg      60
cggccaggcc atgagcttct gcatccccac cgagtacacc atgcacatcg agcgccgcga     120
gtgcgcctac tgcctgacca tcaacaccac catctgcgcc ggctactgca tgacccgcga     180
catcaacggc aagctgttcc tgcccaagta cgccctgagc caggacgtgt gcacctaccg     240
cgacttcatc taccgcaccg tggagatccc cggctgcccc ctgcacgtgg cccctactt     300
cagctacccc gtggccctga ctgcaagtg cggcaagtgc aacaccgact acagcgactg     360
catccacgag gccatcaaga ccaactactg caccaagccc cagaagagct acctggtggg     420
cttcagcgtg taagcggccg c                                               441
```

<210> SEQ ID NO 48
<211> LENGTH: 125
<212> TYPE: DNA
<213> ORGANISM: Artificial Sequence
<220> FEATURE:
<223> OTHER INFORMATION: Synthetic sequence containing WAP3'UTR

<400> SEQUENCE: 48

```
gcggccgcct acccaggagt ccctggctgc caggagagtt gggcctgagt tcccccctctt      60
ggacccagag agcttgtgac gcctcctccc tgctgctaat aaaactactc agcttctaac     120
ggccg                                                                 125
```

<210> SEQ ID NO 49
<211> LENGTH: 37
<212> TYPE: DNA
<213> ORGANISM: Artificial Sequence
<220> FEATURE:
<223> OTHER INFORMATION: Primer TSHalpha5', synthetic sequence

<400> SEQUENCE: 49

```
ccgacgcgtc gccaccatgg actactaccg caagtac                               37
```

<210> SEQ ID NO 50
<211> LENGTH: 45
<212> TYPE: DNA
<213> ORGANISM: Artificial Sequence
<220> FEATURE:
<223> OTHER INFORMATION: Primer TSHalpha3', synthetic sequence

<400> SEQUENCE: 50

```
ggcagccagg gactcctggg tagttagctc ttgtggtagt agcag                      45
```

<210> SEQ ID NO 51
<211> LENGTH: 35
<212> TYPE: DNA
<213> ORGANISM: Artificial Sequence
<220> FEATURE:
<223> OTHER INFORMATION: Primer TSHbeta5', synthetic sequence

<400> SEQUENCE: 51

```
ccgacgcgtc gccaccatgg caaccgccct gttcc                                 35
```

<210> SEQ ID NO 52
<211> LENGTH: 45
<212> TYPE: DNA
<213> ORGANISM: Artificial Sequence
<220> FEATURE:
<223> OTHER INFORMATION: Primer TSHbeta3', synthetic sequence

<400> SEQUENCE: 52

<210> SEQ ID NO 53
<211> LENGTH: 27
<212> TYPE: DNA
<213> ORGANISM: Artificial Sequence
<220> FEATURE:
<223> OTHER INFORMATION: Primer WAP3', synthetic sequence

<400> SEQUENCE: 53
tttggcggcc gcttagaagc tgagtag    27

<210> SEQ ID NO 54
<211> LENGTH: 36
<212> TYPE: DNA
<213> ORGANISM: Artificial Sequence
<220> FEATURE:
<223> OTHER INFORMATION: Primer dE-BbsI-F, synthetic sequence

<400> SEQUENCE: 54
gctgatgaag acccgggacc tgaaataacc tctgaa    36

<210> SEQ ID NO 55
<211> LENGTH: 36
<212> TYPE: DNA
<213> ORGANISM: Artificial Sequence
<220> FEATURE:
<223> OTHER INFORMATION: Primer SynpA-BbsI-R, synthetic sequence

<400> SEQUENCE: 55
ccacaggaag accgcgcgtt atcgctatcg attcac    36

<210> SEQ ID NO 56
<211> LENGTH: 1438
<212> TYPE: DNA
<213> ORGANISM: Artificial Sequence
<220> FEATURE:
<223> OTHER INFORMATION: Rituximab heavy chain, synthetic sequence

<400> SEQUENCE: 56
acgcgtccgc cgccaccatg ggctggagcc tgatcctgct gttcctggtg gccgtggcca    60
cccgcgtgct gagccaggtg cagctgcagc agcctggcgc tgagctggtc aaacccggcg    120
ccagcgtgaa gatgagctgc aaggccacg gctacacctt caccagctac aacatgcact    180
gggtgaagca accccccggc cgcggcctgg agtggatcgg cgccatctac cccggcaacg    240
gcgacaccag ctacaaccag aagttcaagg gcaaggccac cctgaccgcc gacaagagca    300
gcagcaccgc ctacatgcag ctgagcagcc tgaccagcga ggacagcgcc gtgtactact    360
gcgcccgcag cacctactac ggcggcgact ggtacttcaa cgtgtgggc gccggcacca    420 ccgtgaccgt gagcgccgcc agcaccaagg gcctagcgt attccccctg gcccccagca    480
gcaagagcac cagcggcggc accgccgccc tgggctgcct cgtgaaagac tacttccccg    540
agcccgtgac cgtgagctgg aacagcggcg ccctgaccag cggcgtgcac accttccccg    600
ccgtgctgca gagcagcggc ctgtacagc tgagcagcgt ggtgaccgtg cccagcagca    660
gcctgggcac ccagacctac atctgcaacg tgaaccacaa gcccagcaac accaaggtgg    720
acaagaaggc cgagcccaag agctgcgaca agacccacac ctgccccccc tgccccgccc    780
ccgagctgct gggcggcccc agcgtgttcc tgttcccccc caagcccaag gacaccctga    840
tgatcagccg cacccctgaa gtgacctgcg tggtggtgga cgtgagccac gaggacccg    900

```
aggtgaagtt caactggtac gtggacggcg tggaggtgca caacgccaag accaagcccc      960
gcgaggagca gtacaacagc acctaccgcg tggtgagcgt gctgaccgtg ctgcaccagg     1020
actggctgaa cggcaaggag tacaagtgca aggtgagcaa caaggccctg cccgccccca     1080
tcgagaagac catcagcaag gccagggcc agccccgcga gccccaggtg tacaccctgc      1140
cccccagccg cgacgagctg accaagaacc aggtgagcct gacctgcctg gtgaagggct     1200
tctaccccag cgacatcgcc gtggagtggg agagcaacgg ccagcccgag aacaactaca     1260
agaccacccc ccccgtgctg gacagcgacg gcagcttctt cctgtacagc aagctgaccg     1320
tggacaagag ccgctggcag cagggcaacg tgttcagctg cagcgtgatg cacgaggccc     1380
tgcacaacca ctacacccag aagagcctga gcctgagccc cggcaagtaa gcggccgc      1438
```

<210> SEQ ID NO 57
<211> LENGTH: 733
<212> TYPE: DNA
<213> ORGANISM: Artificial Sequence
<220> FEATURE:
<223> OTHER INFORMATION: Rituximab light chain, synthetic sequence

<400> SEQUENCE: 57

```
acgcgtccgc cgccaccatg gacttccagg tgcagatcat cagcttcctg ctgatcagcg      60
ccagcgtgat catgagccgc ggccagatcg tgctgagcca gagccccgcc atcctgagcg     120
ccagccccgg cgagaaggtg accatgacct gccgcgccag cagcagcgtg agctacatcc     180
actggttcca gcagaagccc ggcagcagcc ccaagccctg gatctacgcc accagcaacc     240
tggccagcgg cgtgcccgtg cgcttcagcg gcagcggcag cggcaccagc tacagcctga     300
ccatcagccg cgtggaggcc gaggacgccg ccacctacta ctgccagcag tggaccagca     360 accccccac cttcggcggc ggcaccaagc tggagatcaa cgcaccgtg gccgccccca      420 gcgtgttcat cttccccccc agcgacgagc agctgaagag cggcaccgcc agcgtggtgt     480
gcctgctgaa caacttctac ccccgcgagg ccaaggtgca gtggaaggtg gacaacgccc     540
tgcagagcgg caacagccag gagagcgtga ccgagcagga cagcaaggac agcacctaca     600
gcctgagcag caccctgacc ctgagcaagg ccgactacga gaagcacaag gtgtacgcct     660
gcgaggtgac ccaccagggc ctgagcagcc ccgtgaccaa gagcttcaac cgcggcgagt     720
gctaagcggc cgc                                                       733
```

<210> SEQ ID NO 58
<211> LENGTH: 36
<212> TYPE: DNA
<213> ORGANISM: Artificial Sequence
<220> FEATURE:
<223> OTHER INFORMATION: Primer dE-BbsI-F, synthetic sequence

<400> SEQUENCE: 58

```
gctgatgaag acccgggacc tgaaataacc tctgaa                               36
```

<210> SEQ ID NO 59
<211> LENGTH: 36
<212> TYPE: DNA
<213> ORGANISM: Artificial Sequence
<220> FEATURE:
<223> OTHER INFORMATION: Primer SynpA-BbsI-R, synthetic sequence

<400> SEQUENCE: 59

```
ccacaggaag accgcgcgtt atcgctatcg attcac                               36
```

EXPRESSION VECTOR

TECHNICAL FIELD

The present invention relates to a novel expression vector for efficient expression of recombinant proteins in mammalian cells, and in particular to an expression vector that comprises a gene expression regulatory site, a gene encoding a protein of interest downstream thereof, an internal ribosome entry site further downstream thereof, a gene encoding a glutamine synthetase still further downstream thereof, and a dihydrofolate reductase gene downstream of either the same gene expression regulatory site or another gene expression regulatory site in addition to the former.

BACKGROUND ART

In some fields of industry such as drug manufacturing, a familiar technology is a method for production of a recombinant protein of interest using mammalian cells transformed with an expression vector that contains an incorporated gene encoding the protein. Using this technology, various products are produced and marketed, e.g., lysosomal enzymes such as α-galactosidase A, iduronate-2-sulfatase, glucocerebrosidase, galsulfase, α-L-iduronidase, α-glucosidase, and the like; tissue plasminogen activator (t-PA); blood coagulation factors such as blood coagulation factor VII, blood coagulation factor VIII, blood coagulation factor IX, and the like; erythropoietin; interferon; thrombomodulin; follicle-stimulating hormone; granulocyte colony-stimulating factor (G-CSF); various antibody medicaments, and the like.

In performing this technology, it is a general practice to employ an expression vector in which a gene encoding a protein of interest is incorporated downstream of a gene regulatory site that induces a potent expression of a gene, such as a cytomegalovirus (CMV)-derived promoter, SV40 early promoter (SV40 enhancer/promoter), or elongation factor 1α (EF-1) promoter. Mammalian cells, after introduction therein of such an expression vector, come to express the protein of interest that is incorporated in the expression vector. The levels of its expression, however, vary and are not even among those cells. Therefore, for efficient production of the recombinant protein, a step is required to select, from the mammalian cells containing the expression vector introduced therein, those cells which express the protein of interest at high levels. For performing this selection step, a gene that acts as a selection marker is incorporated in an expression vector.

The most popular of such selection markers are enzymes (drug resistance markers) that decompose drugs such as puromycin, neomycin, and the like. Mammalian cells will be killed in the presence of these drugs beyond certain concentrations. Mammalian cells into which an expression vector has been introduced, however, become viable in the presence of those drugs because such cells can decompose the drugs with the drug selection markers incorporated in the expression vector and thus detoxify them or weaken their toxicity. Therefore, when those cells having such an incorporated expression marker are cultured in a medium containing one of the above mentioned drugs beyond a certain concentration, only such cells grow that express the corresponding selection marker at high levels, and as a result, they are selected. Such cells that express a drug selection marker at high levels also tend to express, at high levels, a gene encoding a protein of interest incorporated together in the expression vector, and as a result, mammalian cell thus will be obtained that express the protein of interest at high levels.

There is also known a method to obtain mammalian cells that express a protein of interest at high levels utilizing dihydrofolate reductase (DHFR) as a selection marker (Non-patent Document 1). Dihydrofolate reductase is an enzyme which reduces dihydrofolate to tetrahydrofolate. Mammalian cells will die if they are cultured in a thymidine-hypoxanthine-free medium in the presence of methotrexate (MTX), an inhibitor of DHFR, beyond a certain concentration. However, if an expression vector containing an incorporated DHFR gene as a selection marker is introduced into mammalian cells, they become capable of growing even at higher concentrations of MTX because of elevated expression levels of DHFR in them. In this circumstance, if culture is continued gradually elevating the MTX concentration, such cells are obtained that can grow in the presence of even higher concentrations of MTX. This phenomenon is thought to occur because of increase in number of the copies of the expression vector incorporated into the genome of the mammalian cells by multiplication. That is, an increase in number of copies of the expression vector leads to a corresponding increase in number of the DHFR genes in the genome of each cell, resulting in relatively enhanced levels of expression of DHFR. In this process, the number of copies of the gene encoding a protein of interest and simultaneously incorporated in the expression vector also increases, and thus gives mammalian cells that express the protein of interest at high levels.

Expression vectors are also known in which a glutamine synthetase (GS) is used as a selection marker (cf. Patent Documents 1 and 2). Glutamine synthetase is an enzyme which synthesizes glutamine from glutamic acid and ammonia. If mammalian cells are cultured in a medium which lacks glutamine in the presence of methionine sulfoximine (MSX), an inhibitor of glutamine synthetase, beyond a certain concentration, the cells will be annihilated. However, if an expression vector into which a glutamine synthetase has been incorporated as a selection marker is introduced into mammalian cells, the cells, now with increased levels of expression of the glutamine synthetase, become capable of growing even in the presence of higher concentrations of MSX. In doing this, if culture is continued with a gradually increasing concentration of MSX, such cells are obtained that can grow in the presence of still higher concentrations of MSX. This phenomenon occurs in the same mechanism as where DHFR is used as a selection marker. Therefore, by incorporating in an expression vector a gene encoding a protein of interest together with a GS gene, such mammalian cells will be obtained that express the protein of interest at high levels. For example, Patent Document 1 discloses that by employment of a GS gene and methionine sulfoximine (MSX) enables greater increase of the copy number of the vector DNA than where DHFR gene and methotrexate (MTX) are employed. Further, Patent Document 2 discloses that by employment of a GS gene and MSX, the copy number of a different, heterozygous gene can also be increased, along with increased number of copies of the GS gene, which thereby enables increased production levels of a polypeptide of interest.

Thus, expression vectors containing a selection marker are suitable for efficient production of recombinant proteins, and thus are commonly used. A gene encoding a protein of interest and a gene encoding a selection marker are generally incorporated in an expression vector downstream of respective different gene regulatory sites (cf. Patent Document 3).

However, a method is also known in which genes encoding a protein of interest and a selection marker are incorporated in series downstream of a single gene regulatory site to let them express themselves (cf. Patent Documents 4-7). In performing this, an internal ribosome entry site (IRES) and the like are inserted between the genes encoding a protein of interest and a selection marker, which enables expression of two genes under a single gene regulatory site. Various internal ribosome entry sites are known: for example, those derived from picornavirus, poliovirus, encephalomyocarditis virus, and chicken infectious Fabricius bursal disease virus (cf. Patent Documents 8-10).

Among expression vectors utilizing an internal ribosome entry site, there are known an expression vector in which herpes simplex virus thymidine kinase is incorporated as a selection marker downstream of an internal ribosome entry site (cf. Patent Document 11), and an expression vector in which three or more genes are combined using two or more internal ribosome entry sites (cf. Patent Document 12).

As mentioned above, owing to development of various expression vectors, methods for production of recombinant proteins using mammalian cells have been in practical use for production of medicaments, such as erythropoietin and the like. However, development of expression vectors which are more efficient than conventional ones are consistently sought in order to lower the cost for their production.

PRIOR ART DOCUMENTS

Patent Documents

[Patent Document 1] Japanese Patent Application Publication No. S63-502955
[Patent Document 2] Japanese Patent Application Publication No. H05-504050
[Patent Document 3] Japanese Patent Application Publication No. 2009-273427
[Patent Document 4] Japanese Patent Application Publication No. S59-173096
[Patent Document 5] Japanese Patent Application Publication No. S60-19938 7
[Patent Document 6] Japanese Patent Application Publication No. H04-500004
[Patent Document 7] Japanese Patent Application Publication No. H08-256776
[Patent Document 8] Japanese Patent Application Publication No. H06-509713
[Patent Document 9] Japanese Patent Application Publication No. H08-502644
[Patent Document 10] Japanese Patent Application Publication No. H10-327871
[Patent Document 11] Japanese Patent Application Publication No. 2008-539785
[Patent Document 12] Japanese Patent Application Publication No. 2004-520016

Non-Patent Documents

[Non-patent Document 1] Kaufman R J. et al., Mol Cel Biol. 2, 1304-19 (1982)

SUMMARY OF INVENTION

Problem to be Solved by Invention

The objectives are to provide a novel expression vector for efficient expression of recombinant proteins in mammalian cells, mammalian cells transformed with the vector, and a method for production of such mammalian cells.

Means to Solve the Problem

In a study directed to the above objectives, the present inventors transformed mammalian cells with an expression vector in which are incorporated a gene expression regulatory site, and a gene encoding a protein of interest, such as human follicle-stimulating hormone, downstream thereof, an internal ribosome entry site further downstream thereof, and a gene encoding glutamine synthetase still further downstream thereof, and a dihydrofolate reductase gene downstream of either the same gene expression regulatory site or another gene expression regulatory site in addition to the former, and thereby found that a high level expression of the gene encoding the protein thereby becomes available, having completed the present invention. Thus, the present invention provides what follows.

1 An expression vector for expression of a protein, comprising a gene expression regulatory site (A), and a gene encoding the protein downstream thereof, an internal ribosome entry site further downstream thereof, a gene encoding a glutamine synthetase still further downstream thereof, and additionally a dihydrofolate reductase gene downstream of either the same gene expression regulatory site (A) or another gene expression regulatory site (B) in addition to the former.

2. The expression vector according to 1 above, wherein the gene expression regulatory site (A) and/or the gene expression regulatory site (B) are selected from the group consisting of a cytomegalovirus-derived promoter, SV40 early promoter, and elongation factor 1 promoter.

3. The expression vector according to 1 or 2 above, wherein the internal ribosome entry site is derived from the 5' untranslated region of a virus or a gene selected from the group consisting of a virus of *Picornaviridae, Picornaviridae Aphthovirus*, hepatitis A virus, hepatitis C virus, coronavirus, bovine enterovirus, Theiler's murine encephalomyelitis virus, Coxsackie B virus, human immunoglobulin heavy chain binding protein gene, drosophila antennapedia gene, and drosophila Ultrabithorax gene.

4. The expression vector according to 1 or 2 above, wherein the internal ribosome entry site is derived from the 5' untranslated region of a virus of *Picornaviridae*.

5. The expression vector according to 1 or 2 above, wherein the internal ribosome entry site is derived from the 5' untranslated region of mouse encephalomyocarditis virus.

6. The expression vector according to one of 1 to 5 above, wherein the internal ribosome entry site is that which is prepared by introducing one or more mutations into the nucleotide sequence of a wild-type internal ribosome entry site.

7. The expression vector according to 6 above, wherein the nucleotide sequence of the wild-type internal ribosome entry site includes two or more start codons, wherein part of the two or more codons have been destroyed by the mutation.

8. The expression vector according to 5 above, wherein the internal ribosome entry site comprises the nucleotide sequence set forth as SEQ ID NO:1.

9. The expression vector according to 5 above, wherein the internal ribosome entry site comprises the nucleotide sequence set forth as SEQ ID NO:2.

10. The expression vector according to 5 above, wherein the internal ribosome entry site comprises the nucleotide sequence set forth as SEQ ID NO:3.

11. The expression vector according to 5 above, wherein the internal ribosome entry site comprises the nucleotide sequence set forth as SEQ ID NO:4.

12. The expression vector according to 5 above, wherein the internal ribosome entry site comprises the nucleotide sequence set forth as SEQ ID NO:5.

13. The expression vector according to 5 above, wherein the internal ribosome entry site comprises the nucleotide sequence set forth as SEQ ID NO:6.

14. The expression vector according to one of 1 to 13 above, further comprising, either in the region between the gene encoding the protein and the internal ribosome entry site or in the region downstream of the gene encoding the glutamine synthetase, another internal ribosome entry site in addition to the former internal ribosome entry site, and a drug resistance gene downstream thereof.

15. The expression vector according to one of 1 to 13 above, wherein the expression vector, in addition to the gene expression regulatory site (A) and the gene expression regulatory site (B), further comprises another gene expression regulatory site (C) and a drug resistance gene downstream thereof.

16. The expression vector according to 14 or 15 above, wherein the drug resistance gene is a puromycin or neomycin resistance gene.

17. The expression vector according to one of 1 to 16 above, wherein the gene encoding the protein is a human-derived gene.

18. The expression vector according to 17 above, wherein the human-derived gene is selected from the group consisting of the genes encoding lysosomal enzymes, tissue plasminogen activator (t-PA), blood coagulation factors, erythropoietin, interferon, thrombomodulin, thyroid stimulating hormone (TSH), follicle-stimulating hormone, granulocyte colony-stimulating factor (G-CSF), and antibodies.

19. The expression vector according to 17 above, wherein the human-derived gene is a gene encoding a lysosomal enzyme.

20. The expression vector according to 19 above, wherein the lysosomal enzyme is selected from the group consisting of α-galactosidase A, iduronate-2-sulfatase, glucocerebrosidase, galsulfase, α-L-iduronidase, and acid α-glucosidase.

21. The expression vector according to 17 above, wherein the human-derived gene is a gene encoding erythropoietin.

22. A mammalian cell transformed with the expression vector according to one of 1 to 21 above.

23. The cell according to 22 above, wherein the mammalian cell lacks the intrinsic dihydrofolate reductase gene.

24. The cell according to 22 or 23 above, wherein the mammalian cell is a CHO cell.

25. A method for production of a transformed cell expressing a gene encoding the protein comprising the steps of:

(a) introducing the expression vector according to one of 1 to 21 above into a mammalian cell, (b) subjecting the mammalian cell containing the introduced expression vector to a selective culture in the presence of an inhibitor of dihydrofolate reductase, and (c) subjecting the cells selected through the selective culture to a further selective culture in the presence of an inhibitor of glutamine synthetase.

26. A method for production of a transformed cell expressing a gene encoding the protein comprising the steps of:

(a) introducing the expression vector according to one of 14 to 16 above into a mammalian cell, (b) subjecting the mammalian cell containing the introduced expression vector to a selective culture in the presence of an inhibitor of dihydrofolate reductase, and (c) subjecting the cells selected through the selective culture to a further selective culture in the presence of an inhibitor of glutamine synthetase, further comprising the step of subjecting the mammalian cell containing the introduced expression vector to a selective culture in the presence of a drug corresponding to the drug resistance gene.

Effect of Invention

According to the present invention, an expression vector is provided for efficient expression of a recombinant protein of interest in mammalian cells. Transformed cells which efficiently produce a recombinant protein can be obtained by introducing the expression vector into mammalian cells and then subjecting the cells to a selective culture. Use of thus obtained transformed cells enables significant cost reduction in the production of recombinant proteins.

BRIEF DESCRIPTION OF DRAWINGS

FIG. 1-2 A diagram illustrating a flow of the method for construction of pE-neo vector.

FIG. 2-1 A diagram illustrating a flow of the method for construction of pE-hygr vector.

FIG. 2-2 A diagram illustrating a flow of the method for construction of pE-hygr vector.

FIG. 2-3 A diagram illustrating a flow of the method for construction of pE-hygr vector.

FIG. 3-1 A diagram illustrating a flow of the method for construction of pE-IRES-GS-puro.

FIG. 3-2 A diagram illustrating a flow of the method for construction of pE-IRES-GS-puro.

FIG. 3-3 A diagram illustrating a flow of the method for construction of pE-IRES-GS-puro.

FIG. 3-4 A diagram illustrating a flow of the method for construction of pE-IRES-GS-puro.

FIG. 3-5 A diagram illustrating a flow of the method for construction of pE-IRES-GS-puro.

FIG. 3-6 A diagram illustrating a flow of the method for construction of pE-IRES-GS-puro.

FIG. 3-7 A diagram illustrating a flow of the method for construction of pE-IRES-GS-puro.

FIG. 3-8 A diagram illustrating a flow of the method for construction of pE-IRES-GS-puro.

FIG. 3-9 A diagram illustrating a flow of the method for construction of pE-IRES-GS-puro.

FIG. 4 A diagram illustrating a flow of the method for construction of pE-mIRES-GS-puro.

FIG. 5 A diagram illustrating a flow of the method for construction of pE-mIRES-GS.

FIG. 6 A diagram illustrating a flow of the method for construction of pE-mIRES-GS-mNeo FIG. 7 A diagram illustrating a flow of the method for construction of pBlue-EF1/mIRES-mNeo FIG. 8 A diagram illustrating a flow of the method for construction of pBlue-EF1/SVpA FIG. 9 A diagram illustrating a flow of the method for construction of pE-mDHFR31

FIG. 10-1 A diagram illustrating a flow of the method for construction of pCI-neo (TSHα-WAP3'UTR)

FIG. 10-2 A diagram illustrating a flow of the method for construction of pCI-neo (TSHβ-WAP3'UTR)

FIG. 18-1 A diagram illustrating a flow of the method for construction of pBlue-EF1/SVpA(RTX-L)

FIG. 18-2 A diagram illustrating a flow of the method for construction of pE-mIRES-GS-dual(RTX)

FIG. 18-3 A diagram illustrating a flow of the method for construction of pE-mIRES-GS-dual+mDHFR31(RTX)

MODE FOR CARRYING OUT THE INVENTION

Figure 1:
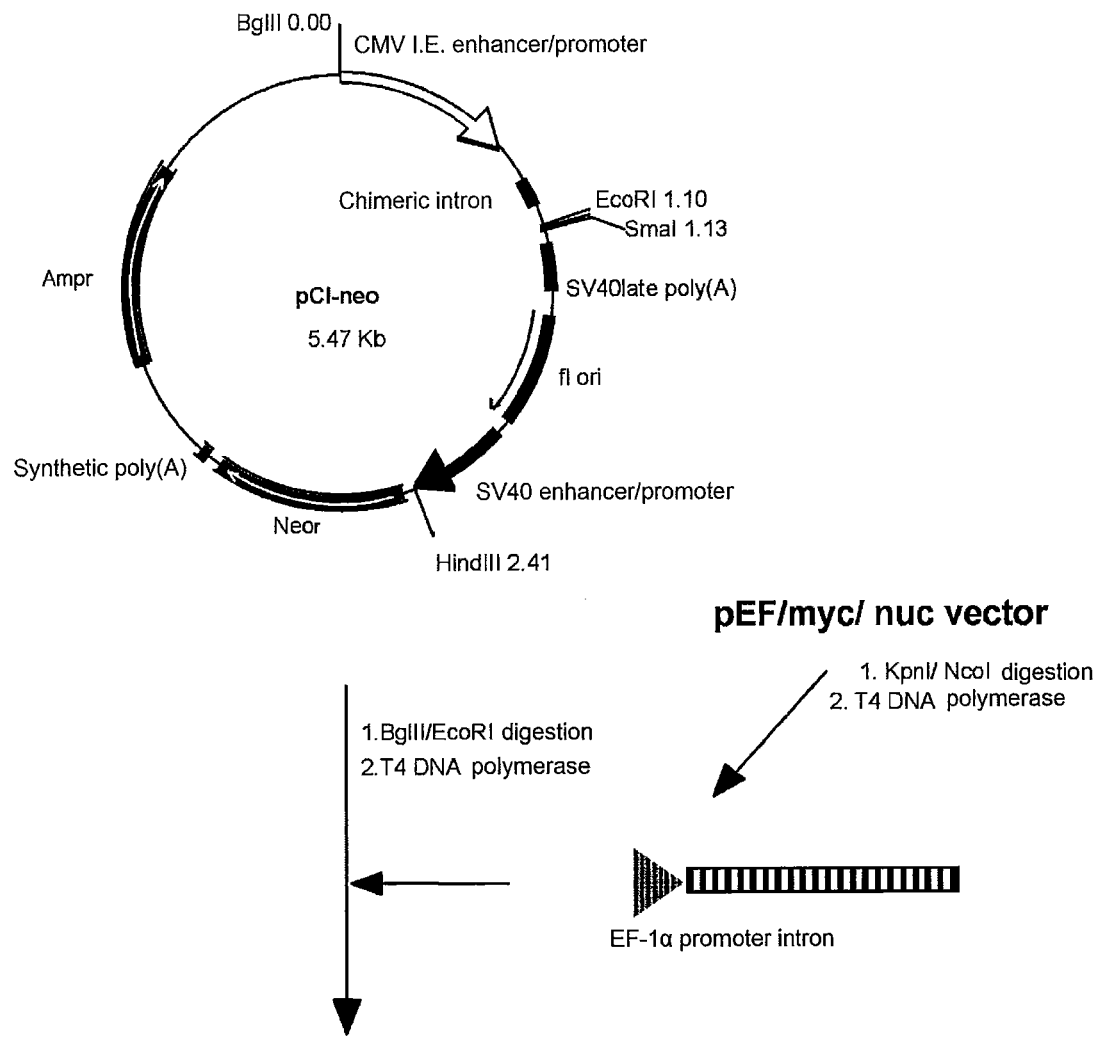
FIG. 1-1 A diagram illustrating a flow of the method for construction of pE-neo vector.

In the present invention, the term "gene" means structural gene. The term "gene expression regulatory site" means a DNA region which can regulate (control) the transcription frequency of the gene located downstream thereof, and generally is called a promoter or a promoter gene. A gene expression regulatory site is present upstream of almost every gene which is expressed in the body, regulating (controlling) the transcription frequency of the gene, and its nucleotide sequence is diverse. Though there is no particular limitation to it as far as it is able to strongly induce expression of a gene incorporated downstream thereof in mammalian cells, a gene expression regulatory site which can be used in the present invention is preferably a virus-derived promoter, such as a cytomegalovirus (CMV)-derived promoter, SV40 early promoter, and the like; and elongation factor 1α (EF-1) promoter, and the like.

In the present invention, the term "internal ribosome entry site" means a region (structure) inside an mRNA chain to which a ribosome can directly binds and start translation independently from a cap structure, or a region (structure) in a DNA which generates such a region through translation. In the present invention, the term "gene encoding an internal ribosome entry site" means a region (structure) in a DNA which generates such a site through translation. Internal ribosome entry site is generally called IRES, and found in the 5' untranslated region of viruses of *Picornaviridae* (poliovirus, rhinovirus, mouse encephalomyocarditis virus, and the like), *Picornaviridae Aphthovirus*, hepatitis A virus, hepatitis C virus, coronavirus, bovine enterovirus, Theiler's murine encephalomyelitis virus, Coxsackie B virus, and the like, and the 5' untranslated region of human immunoglobulin heavy chain binding protein, drosophila antennapedia gene, drosophila Ultrabithorax gene, and the like. In the case of a picornavirus, its IRES is a region consisting of about 450 bp present in the 5' untranslated region of its mRNA. Here, "5' untranslated region of a virus" means the 5' untranslated region of a viral mRNA, or a region (structure) in a DNA which, when translated, generates such a region.

In the present invention, there is no particular limitation as to which of internal ribosome entry sites is employed, and any one of them may be used as far as it can act as an internal ribosome entry site in a mammalian cell, in particular a. Chinese hamster ovary-derived cell (CHO cell). Among them, preferred is an internal ribosome entry site derived from the 5' untranslated region of a virus, more preferred an internal ribosome entry site derived from the 5' untranslated region of a virus of *Picornaviridae*, and still more preferred an internal ribosome entry site derived from mouse encephalomyocarditis virus.

In the present invention, internal ribosome entry sites having a wild-type nucleotide sequence may be used directly. Further, any of mutant-type internal ribosome entry sites derived by introducing one or more mutations (such as substitution, deletion, and/or insertion) into one of those wild-type internal ribosome entry sites may also be used so long as it can act as an internal ribosome entry site in mammalian cells (especially, CHO cells). Further, a chimeric-type internal ribosome entry site may also be used which is derived by fusion of two or more internal ribosome entry sites.

In addition, in the present invention, placing a gene encoding a glutamine synthetase (GS gene) under the regulation of an internal ribosome entry site, enables control of expression levels of the GS gene. By controlling the expression levels of the GS gene under the regulation of an internal ribosome entry site, it is possible to select mammalian cells which express a recombinant protein at high levels, as mentioned later.

Besides, in the present invention, a culture performed to select those cells in which a selective marker is incorporated, regardless whether they are GS gene-incorporated cells or not, is referred to as a "selective culture", and the medium employed to select those cells as a "selective medium".

Where the expression levels of a GS gene is controlled under the regulation of an internal ribosome entry site, a proper one may be used that is selected as desired from various internal ribosome entry sites. It is also possible to use an internal ribosome entry site that is prepared by incorporating mutations into a wild-type.

For example, where there are multiple start codons (ATG) within a wild-type internal ribosome entry site each of them can be employed as an initiation point of translation, an internal ribosome entry site can be used that is prepared by destruction of part of those start codons. The term "destruction" here means introduction of one or more mutations into a sequence of a gene to thereby prevent the intrinsic function of the gene from working. For example, the internal ribosome entry site of the wild-type mouse encephalomyocarditis virus has three start codons (ATG) at its 3' end, whose sequence is set forth as SEQ ID NO:1 (5'-ATGataatATGgc-cacaaccATG-3': start codons shown in upper letters for clarity). If it is intended to lower the expression level of the GS gene located downstream of this internal ribosome entry site, the start codon to be destroyed by introduction of a mutation is preferably the 2nd or 3rd start codon from the 5' end, more preferably the 2nd start codon. Thus, examples of an internal ribosome entry sites containing such an introduced mutation include those having at their 3' end a nucleotide sequence set forth as SEQ ID NO:2 (5'-ATGataatnnngccacaaccnnn-3': n representing any nucleotide, provided that these three "n" s do not constitute a start codon ATG. The same shall apply hereinafter.) or a nucleotide sequence set forth as SEQ ID NO:7 (5'-ATGataannnngccacaaccnnn-3') or a nucleotide sequence set forth as SEQ ID NO:3 (5'-ATGataatnnngccacaaccATG-3') or a nucleotide sequence set forth as SEQ ID NO:8 (5'-ATGataannnngccacaaccATG-3'). More specifically, an example is an internal ribosome entry site having at its 3' end a nucleotide sequence set forth as SEQ ID NO:4 (5'-ATGataagcttgccacaaccATG-3'), in which the 2nd start codon from the 5' end has been destroyed by mutation. Still more specifically, the internal ribosome entry site of the wild-type mouse encephalomyocarditis virus comprises a nucleotide sequence set forth as SEQ ID NO:5. Further, an example of nucleotide sequences which are prepared by introducing a mutation into the above nucleotide sequence is the one set forth as SEQ ID NO:6.

Furthermore, the expression levels of a GS gene placed downstream of a wild-type and/or a mutant-type internal ribosome entry site may be controlled by other methods. For example, lowered expression level of the gene can also be achieved either by incorporating the GS gene in an out-of-frame fashion relative to the start codon in the internal ribosome entry site or by introducing a nucleotide sequence that inhibits transcription or translation between the internal ribosome entry site and the GS gene. There is no particular limitation as to a nucleotide sequence that inhibits transcription, and examples include the polymerase addition signal (5'-aataaa-3') and the like. Examples of such nucleotide sequences that inhibit translation include a stop codon that induces a reading through.

In the present invention, there is no particular limitation as to the term "glutamine synthetase" so long as it is capable of synthesizing glutamine from glutamic acid and ammonia, and it may be of any origin including mammals, reptiles, birds, amphibians, insects such as *Bombyx mori, Spodoptera frugiperda, Geometridae*, and the like, of *Lepidoptera; Drosophila* of *Diptera*; procaryotes; nematodes; yeasts; actinomycetes; filamentous fungi; ascomycetes; Basidiomycota; and plants. Among these, preferred are those originating from mammals, and one originating from human or Chinese hamster (esp. originating from CHO cells) may be preferably used.

In the present invention the term "intrinsic GS gene" means the glutamine synthetase inherently occurring in the original genome of a cell in which an expression vector is to be incorporated, and the term "exogenous GS gene" means a glutamine synthetase gene that is introduced into the cell by an expression vector.

Furthermore, there is no particular limitation as to the term "glutamine synthesis inhibiter", and any compound may be used so long as it is capable of inhibiting the activity of the glutamine synthetase mentioned above. Preferred examples include methionine sulfoximine (MSX).

If cells in which the expression vector of the present invention has been introduced are cultured in a medium in the presence of an inhibitor of glutamine synthetase (GS inhibitor), cells with lower expression levels of glutamine synthetase will be annihilated because they now are incapable of synthesizing glutamine, and thus those cells with higher expression levels of glutamine synthetase will be selectively obtained. By elevating the concentration of the GS inhibitor stepwise, cells will be obtained which exhibit still higher expression levels of glutamine synthetase. This elevation of the expression levels of glutamine synthetase is brought about mainly through increase in the copy number of the incorporated GS gene in the chromosomes by gene multiplication. When this occurs, the number of the copies of the gene encoding a protein of interest incorporated in the expression vector is also increased by gene multiplication, thus yielding such mammalian cells that express the protein of interest at high levels.

However, CHO cells have an intrinsic GS gene of their own, and therefore there is a possibility that the number of copies of the intrinsic GS gene may be increased through multiplication by a glutamine synthetase inhibitor employed. If this occurred, the cells will grow in the presence of the glutamine synthetase inhibitor even without multiplication of the incorporated GS gene in the expression vector, resulting in failure to obtain cells that exhibit high expression levels of the above-mentioned protein of interest. This problem can be solved by additional incorporation of a second selection marker gene, a different one from a GS gene, into the expression vector.

First, an expression vector containing a GS gene and a second selection marker gene, which is not a GS gene, are incorporated into a cell. The cell, then, is subjected to a selective culture using the second selection marker before performing a selective culture using the GS gene. Since no GS gene receives a selection pressure during the selection process using the second selection marker, the second selection marker incorporated in the expression vector, and therefore the gene encoding the above-mentioned protein of interest and the GS gene incorporated both in the expression vector can be increased in their numbers by multiplication, without receiving any influence from the intrinsic GS gene. As a result, such cells will be obtained that express the above-mentioned protein of interest at levels elevated to a certain degree. Up to this point of the process, the number of copies of the exogenous GS gene has been increased by multiplication, whereas the intrinsic GS gene has never been increased by multiplication.

The selective medium that is employed in the selection using the second selection marker (second selective medium) may be a medium supplemented with a compound, as a selection compound, that is used to perform the selection of cells based on the second selection marker, such as a drug that inhibits the activity of the gene product encoded by the second selection marker, a compound that is cytotoxic and is to be detoxified or attenuated by the gene product encoded by the second selection marker, and the like; or a medium from which such a compound is removed as a selection compound that the cells, after introduction of the second selection marker, will no more require as a nutrient (namely, a compound that is required by the cells as a nutrient only before the introduction of the second marker). In the case where the second selection marker is DHFR, examples of selection compounds to be added to the medium include methotrexate (MTX) and aminopterin. Also if the second selection marker is DHFR, the selection compounds to be removed from the medium are hypoxanthine and thymidine.

If the selection with the second selection marker is performed using a medium supplemented with a selection compound, cells with still further elevated expression levels of the second selection marker can be obtained by stepwise increasing the concentration of the selection compound. This increase in the expression levels of the second selection marker is caused by the increase in the copy number of the second selection marker by gene multiplication, and thus, in this manner, the number of other genes that have been incorporated into the expression vector, i.e., the GS gene and an aforementioned gene encoding a protein of interest, can be increased still more efficiently by multiplication.

Selection of cells then is performed by switching the selection marker to a GS gene. At the start of such a selection using a GS gene as the selection marker, the copy number of the exogenous GS gene has been increased compared with that of the intrinsic GS gene. Therefore, performing a selection of cells by switching the selection marker to a GS gene at this time point will enhance the probability of the exogenous GS gene, which is superior in number, being more greatly amplified by multiplication than the intrinsic GS gene. Thus, by having selected cells in advance by using the second selection marker that is not a GS gene, multiplication of the exogenous GS gene can be boosted during selection using a GS gene while suppressing multiplication of the intrinsic GS gene. As a result, cells that highly express a protein, of interest can be obtained efficiently.

In the present invention, the second selection marker may be incorporated downstream of a separately provided another gene expression regulatory site (the second gene expression regulatory site) in addition to the aforementioned gene expression regulatory site that controls the expression of the recombinant protein of interest. Again, in the present invention, the second selection marker may be provided with a second internal ribosome entry site placed upstream thereof, and through this, be incorporated either into the region between the above-mentioned gene encoding the protein of interest and the internal ribosome entry site downstream thereof, or into the a region downstream of the GS gene. By this way, the expression levels of the second selection marker can be controlled also by the second internal ribosome entry site. In this case, the second internal ribosome entry site may have either the same nucleotide sequence as the internal ribosome entry site upstream of the GS gene or a different nucleotide sequence therefrom. Besides, the second internal ribosome entry site may be chosen as desired from the above-mentioned various internal ribosome entry sites.

In the present invention, while there is no particular limitation as to what is chosen as a second selection marker so far as it is a different selection marker from a GS gene, no gene that confers a drug resistance (drug resistance gene) to mammalian cells is generally not included as candidates of a second selection marker. However, in the case where a third selection marker mentioned later is incorporated into the expression vector to perform further selection of mammalian cells using it, a drug resistance gene may be employed as a second selection marker. A dihydrofolate reductase (DHFR) gene may suitably be used as a second selection marker.

In the present invention, the term "dihydrofolate reductase" (DHFR) means an enzyme that is responsible for the reaction in which dihydrofolate is reduced to tetrahydrofolate. As far as it is an enzyme having this function, there is no particular limitation as for its origin, and thus any one of such enzymes may be employed regardless of their origin including mammals; reptiles; birds; amphibians; insects such as Bombyx mori of Lepidoptera, Spodoptera frugiperda, Geometridae, Drosophila of Diptera; prokaryotes; nematodes; yeasts, Actinobacteria, filamentous fungi, ascomycetes, and basidiomycetes, as well as those originating from plants. Preferred is one originating from mammals, and in particular, those originating from human, mouse, and Chinese hamster (esp. from CHO cells) may suitably be used. In addition to wild-type enzymes originating from these species, mutant-type enzymes that are prepared by introduction of one or more mutations into wild-type enzymes may also be used insofar as they are enzymatically active, and thus are also included in the term "dihydrofolate reductase". There are such mutant-type enzymes that have, e.g., a difference in their enzyme activity, or a difference in their sensitivity to dihydrofolate reductase inhibitors, from their corresponding wild-type enzymes. Examples of dihydrofolate reductases suitably used include mouse wild-type DHFR, and a mutant-type DHFR that is prepared by replacing the phenylalanine at position 31 from the N-terminus of mouse wild-type DHFR with tryptophan (Mclvor R S et al., Nucleic Acids Research, 18(23), 7025-32 (1990)). The nucleotide sequence and the amino acid sequence of mouse wild-type DHFR are set forth as SEQ ID NO:9 and SEQ ID NO:10, respectively, and the nucleotide sequence and the amino acid sequence of their corresponding mutant-type DHFR are set forth as SEQ ID NO:11 and SEQ ID NO:12.

Further, in the present invention, the term "intrinsic DHFR gene" means the DHFR gene that originally and inherently occurs in the genome of the cells into which an expression vector is to be introduced, and the term "exogenous DHFR gene" means a DHFR gene that is introduced in the cells using an expression vector. Still further, in the present invention, insofar as it can inhibit the activity of the above dihydrofolate reductase (DHFR), there is no particular limitation as to "dihydrofolate reductase inhibitors", and thus any one of them may be employed, of which preferred are antifolates and more preferred are methotrexate (MTX) and aminopterin.

In the present invention, when cells having an introduced expression vector containing a DHFR gene as a second selection marker are subjected to culture in the presence of a dihydrofolate reductase inhibitor (DHFR inhibitor), those cells which express the lower levels of DHFR will be annihilated because of their failure to synthesize tetrahydrofolate, thereby selectively yielding cells that express DHFR at the higher levels. By increasing stepwise the concentration of the DHFR inhibitor, cells will be obtained that express DHFR at still higher levels. This increase in the expression level of DHFR is mainly due to the increase of the number of copies of the DHFR gene incorporated in the chromosome through gene multiplication. When this occurs, the other gene incorporated in the expression vector, i.e., the GS gene and the gene encoding the protein of interest are also increase in their copy number due to gene multiplication. As a result, cells are obtained that express the protein of interest at some elevated levels and have an increased number of copies of the exogenous GS gene as compared with those of the intrinsic GS gene. At this point of time, by switching the selection marker to the GS gene and carrying out selection of cells, probability of amplification of the exogenous GS gene, which is superior in number, by gene multiplication becomes greater than the intrinsic GS gene. As a result, cells that express the protein of interest can be obtained efficiently.

When increasing stepwise the concentration of a DHFR inhibitor added to a selective medium, its maximum concentration, where the DHFR inhibitor is methotrexate, is preferably 0.25-5 µM more preferably 0.5-1.5 µM, and still more preferably about 1.0 µM.

In the present invention, a third selection marker, in addition to a GS gene and a second selection marker, may be incorporated into the expression vector. A drug resistance gene may suitably be used as a third selection marker. In the present invention, while there is no particular limitation as to what third selection marker may be employed insofar as it can provide a drug resistance to mammalian cells, preferred are genes that can confer the cells with resistance to such drugs as puromycin, hygromycin, blasticidin, and neomycin. With this regard, drugs such as puromycin, hygromycin, blasticidin, neomycin, and the like are "drugs corresponding to the drug resistance genes", respectively. Among these drug resistance genes, examples include a puromycin resistance gene, a hygromycin resistance gene, a blasticidin resistance gene, and a neomycin resistance gene.

In the present invention, expression levels of a third selection marker may be regulated by incorporating it downstream of a separate gene expression regulatory site (third gene expression regulatory site) provided separately from the gene expression regulatory site by which a recombinant protein is regulated.

Furthermore, in the present invention, a third selection marker may be provided with a second internal ribosome entry site (a third internal ribosome entry site in the case where a second internal ribosome entry site is provided upstream of the second selection maker. The same shall apply hereinafter.) placed upstream thereof, and through this, be incorporated into the region between the gene encoding the protein of interest and the internal ribosome entry site downstream thereof, or into a region downstream of the GS gene, or the like. By this way, the expression level of the third selection marker can be controlled by the second internal ribosome entry site. In this case, the second internal ribosome entry site employed may be either the same as the internal ribosome entry site upstream of the GS gene, and the internal ribosome entry site upstream of the second selection marker if provided, or different one. Further, the second internal ribosome entry site upstream of the third selection marker may be chosen as desired from the various internal ribosome entry sites mentioned above. Also with regard to the second internal ribosome entry site, one or more mutations may be introduced for optimization, as described above.

Where the second selection marker mentioned above is a drug resistance gene, a drug resistance gene used as the third selection marker herein is chosen from drug resistance genes other than the second selection marker. Like the second selection marker, the third selection marker can amplify the GS gene without multiplying the intrinsic GS gene. Thus, by performing selection of cells using the third selection marker, either before or after selection using the second selection marker, the exogenous GS gene can be multiplied without multiplying the intrinsic GS gene. As a result, cells can be efficiently obtained that express the protein of interest at high levels.

In the present invention, there is no particular limitation as to the species of an animal whose gene is incorporated, as encoding a recombinant protein, into an expression vector, whether or not it originates from mammal including human. For example, such a gene is generally of human origin if the expression vector according to the present invention is used for production of ethical pharmaceuticals, and generally originating from the same species of a domestic animal to be treated if the expression vector is used for production of drugs for domestic animals. Again; there is no particular limitation as to what recombinant protein of interest a gene encodes, either, but preferred are such genes that encode lysosomal enzymes including α-galactosidase A, iduronate-2-sulfatase, glucocerebrosidase, galsulfase, α-L-iduronidase, and acid α-glucosidase; tissue plasminogen activator (t-PA); blood coagulation factors including blood coagulation factor WI, blood coagulation factor WIT, and blood coagulation factor IX; erythropoietin, interferons, thrombomodulin, follicle stimulating hormone, granulocyte colony-stimulating factor (G-CSF); DNase I, thyroid stimulating hormone, (TSH) or various antibody medicaments. Examples of antibody medicaments include mouse antibodies, humanized mouse antibodies, and human-mouse chimeric antibodies, human antibodies, and the like, and an example is rituximab, a human-mouse chimeric anti-human CD20 antibody.

In the present invention, where expression of an antibody is intended, a gene encoding either the heavy chain or the light chain of it is incorporated into a vector in such a manner that its expression will be controlled by the gene expression regulatory site that controls the expression of the GS gene, while the gene encoding the other of the chains is incorporated in such a manner that its expression will be controlled by another gene expression regulatory site separately placed in the vector. As gene expression regulatory sites employed here are preferably the same type so that the heavy and light chain of the antibody may be expressed at comparable levels.

Furthermore, in the present invention, if the expression of a protein that forms a heterodimer is intended, a gene encoding one of the subunits taking part in the formation of the heterodimer is incorporated in such a manner that its expression is controlled by the gene expression regulatory site that controls expression of the GS gene, and the gene encoding the other of the subunits is incorporated so that its expression is controlled by another gene expression regulatory site placed in the vector. The expression regulatory sites used for this are preferably of the same type so that the two subunits may be expressed at comparable levels. Examples of proteins that form such heterodimers include follicle stimulating hormone and thyroid stimulating hormone (TSH), and the like.

In the present invention, introduction of an expression vector into mammalian cells is made for the purpose of allowing a gene encoding a recombinant protein to express itself in the mammalian cells. Therefore, it may be made by any method so long as it meets this purpose. An expression vector is a circular plasmid in general, and it may be introduced into cells either in the circular form or after linearized by cleavage with a restriction enzyme.

In the present invention, there is no particular limitation as to mammalian cells into which an expression vector according to the present invention is introduced so long as they can express an intended recombinant protein, and they may be primary culture cells of those collected from organs, muscle tissues, skin tissues, connective tissue, nerve tissue, blood, bone marrow, and the like excised from the body, or their subcultured cells or cell lines established so as to keep their characteristics through repeated subcultures. Those cells may be either normal cells or cells which have become cancerous. Cells which can be used particularly preferably are CHO cells derived from the ovary of a Chinese hamster; human fibroblasts; and COS cells derived from the renal fibroblast of an African green monkey.

Further, mammalian cells into which an expression vector is introduced may have a mutation in their intrinsic gene corresponding to the second selection marker.

In the case where the mutation in the intrinsic gene corresponding to the second selection marker is such that it either lowers or eliminates the expression levels of the gene, or lowers or eliminates the function of the protein encoded by the intrinsic gene, selection pressures from on the selection compound is the more strongly applied to the exogenous second selection marker during the selection process using the second selection marker, and therefore multiplication of the second selection marker is the more accelerated. For example, where the second selection marker is a DHFR gene, if the mutation of the intrinsic DHFR gene is such that it lowers the expression levels of dihydrofolate reductase or eliminates the dihydrofolate reductase, selection pressure from the DHFR inhibitor is applied exclusively to the exogenous DHFR gene during the selection process utilizing the DHFR gene, and therefore multiplication of the exogenous DHFR gene is the more accelerated.

Therefore, by employing such cells that have a mutation in the intrinsic gene corresponding to the second selection marker, cells can be obtained more efficiently that express the protein of interest at high levels.

Before selection by the GS gene, mammalian cells in which the expression vector has been introduced (expression vector-introduced cells) are cultured in a selective medium for cell selection based on the second selection marker. If the second selection marker is DHFR, the medium employed here is a medium supplemented with a DHFR inhibitor. For this, aminopterin or methotrexate (MTX) is preferably used as a DHFR inhibitor. Again, if the second selection marker is a drug resistance gene, the drug corresponding to the drug resistance gene is used.

In the case where DHFR is used as the second selection marker, mammalian cells employed into which an expression vector is to be introduced may be those cells which have a mutation in the intrinsic DHFR gene that causes lowering or elimination of the expression levels of DHFR. Examples of such cells include DG44 strain. DG44 strain fails to express intrinsic DHFR gene. Therefore, when cells of this strain are employed, selection pressure is applied exclusively to the exogenous DHFR gene, and thus the exogenous DHFR gene is efficiently amplified by multiplication. A selective culture may be performed using a medium containing a DHFR inhibitor such as aminopterin or methotrexate (MTX). In doing this, by stepwise increasing the concentration of the DHFR inhibitor, those cells can be obtained which express DHFR at higher levels. Where the concentration of a DHFR inhibitor added to the selective medium is increased stepwise, its maximum concentration, if the DHFR inhibitor is methotrexate, is preferably 0.25-5 µM, more preferably 0.5-1.5 µM, and still more preferably about 1.0 µM.

As a cell strain that lacks a DHFR gene exhibits auxotrophy for hypoxanthine and thymidine, culturing of cells of such a strain to maintain and grow them is conducted in a medium supplemented with these compounds. On the other hand, cells into which an exogenous DHFR gene has been introduced have no auxotrophy for hypoxanthine or thymidine anymore, and therefore, supplementation of the medium with these compounds is not needed. Thus, if an expression vector containing a DHFR gene as a second selection marker is introduced into such cells that exhibit scarce or no DHFR activity to be of an intrinsic DHFR gene due to the lack of the intrinsic DHFR gene, those cells in which the exogenous DHFR gene has been introduced can be selective cultured using a medium containing no hypoxanthine or thymidine as the selective medium. Further, a medium that contains no hypoxanthine or thymidine but is supplemented with a DHFR inhibitor can also be used as a selective medium.

Then, the cells containing the introduced expression vector are cultured in a medium adapted to selection of cells containing an introduced GS gene. A medium employed here is a medium containing little or no glutamine and supplemented with a glutamine synthetase inhibitor (e.g., MSX).

By increasing stepwise the concentration of a GS inhibitor added to the selective medium, cells containing the introduced expression vector that express the GS gene at higher levels can be selected. This is partly due to the fact that the copy number of the GS gene incorporated in the genome of the expression vector-introduced cells multiplies in the process of the selective culture, and among the expression vector-introduced cells, only those with elevated expression levels of the GS gene thus will selectively grow. As the copy number of the gene encoding the recombinant protein incorporated in the expression vector also increases at the same time, the expression levels of the gene also increases. Thus, expression vector-introduced cells with relatively higher expression levels of the recombinant protein of interest can be selected by in this manner of selective culture of the expression vector-introduced cells. In the present specification, expression vector-introduced cells thus selected are referred to as transformed cells.

In the present invention, where the concentration of a GS inhibitor added to a selective medium is increased stepwise, their maximum concentration is preferably 100-1000 µM, more preferably 200-500 µM, and still more preferably about 300 µM where the GS inhibitor is methionine sulfoximine (MSX).

According to the present invention, it is also possible, in addition to selective culture using the second selective medium, to culture the cells containing the introduced expression vector in a medium adapted for selection utilizing a third selection marker before a selective culture using the second selective medium. In this case, the third selective culture using the third selection marker may be carried out either before or after the second selective culture. The third selection marker is a drug resistance gene. Therefore, a drug corresponding to the drug resistance gene is added to the selective medium. In doing this, increasing stepwise the concentration of the drug in the selective medium will give cells expressing the drug resistance gene at increased levels. When increasing stepwise the concentration of the drug added to the selective medium that corresponds to the drug resistance gene, the maximum concentration of the drug is preferably 3-30 µM if the drug is puromycin, and more preferably 5-20 µM, still more preferably about 10 µM. If the drug is G418, its maximum concentration is 0.4-1.5 mg/mL, more preferably 0.8-1.2 mg/mL, and still more preferably about 1 mg/mL.

Examples

Though the present invention will be described in further detail below with reference to examples, it is not intended that the present invention be limited to the examples.

Figures 1, 2:
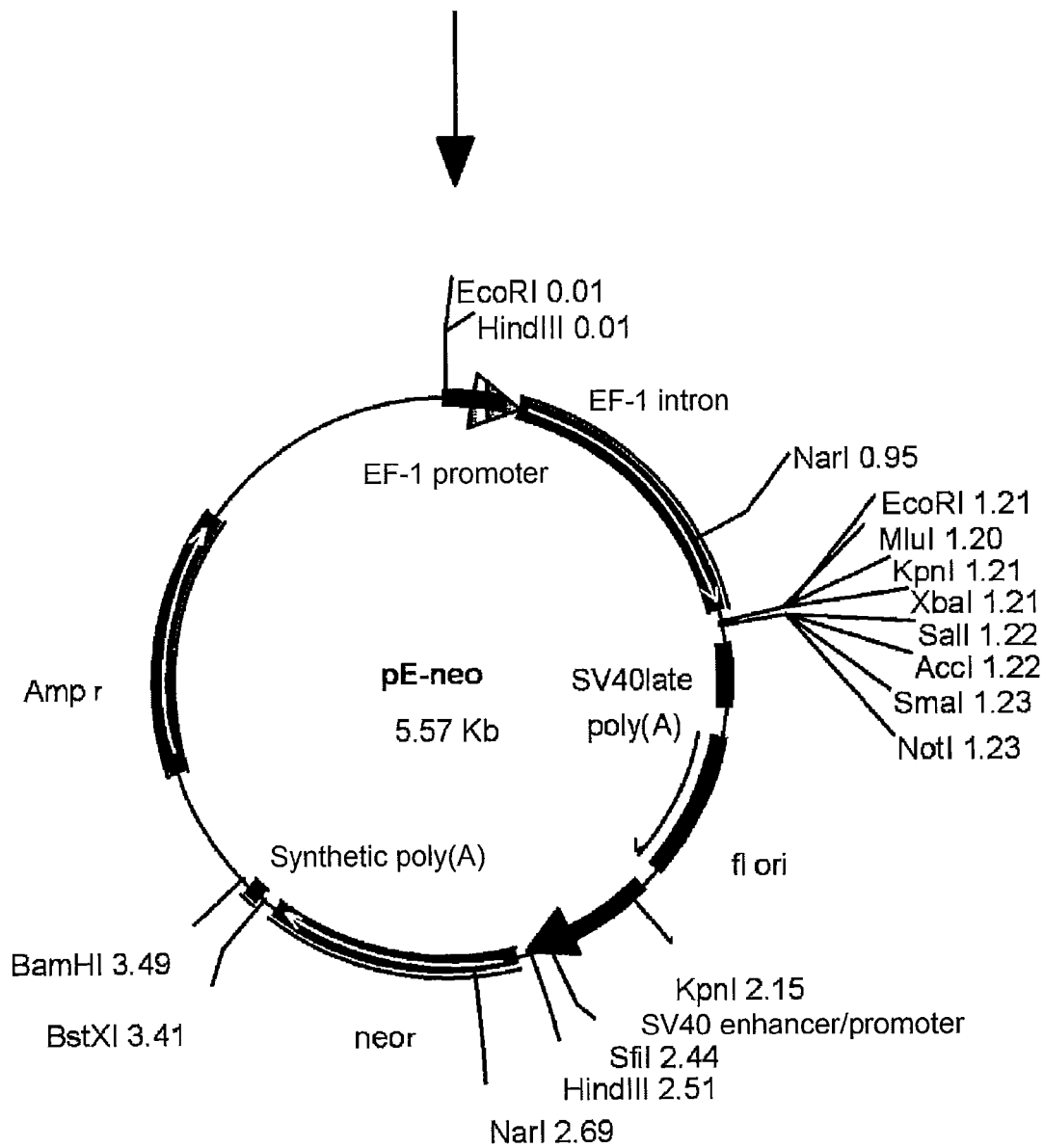

[Construction of pE-Neo Vector and pE-Hygr Vector]

pEF/myc/nuc vector (Invitrogen) was digested with KpnI and NcoI to cut out a region which includes EF-1 promoter and its first intron, which then was blunt-ended with T4 DNA polymerase. Separately, pCI-neo (Invitrogen), after digested with BglII and EcoRI to remove a region containing CMV enhancer/promoter and introns, was blunt-ended with T4 DNA polymerase. Into this was inserted the above-mentioned region (after blunt-ended) including above-mentioned EF-1α promoter and its first intron to construct pE-neo vector (FIG. 1-1 and FIG. 1-2).

pE-neo vector was digested with SfiI and BstXI to cut out a region of about 1 kbp including a neomycin resistance gene (FIG. 2-1). A hygromycin resistance gene was amplified by PCR using pcDNA3.1/Hygro(+) (Invitrogen), as a template, and primer Hyg-Sfi5' (SEQ ID NO:13) and primer Hyg-BstX3' (SEQ ID NO:14)(FIG. 2-2). The hygromycin gene thus amplified then was digested with SfiI and BstXI and inserted into the pE-neo vector mentioned above to construct pE-hygr vector (FIG. 2-3).

[Construction of pE-IRES-GS-puro]

Figures 1, 2:
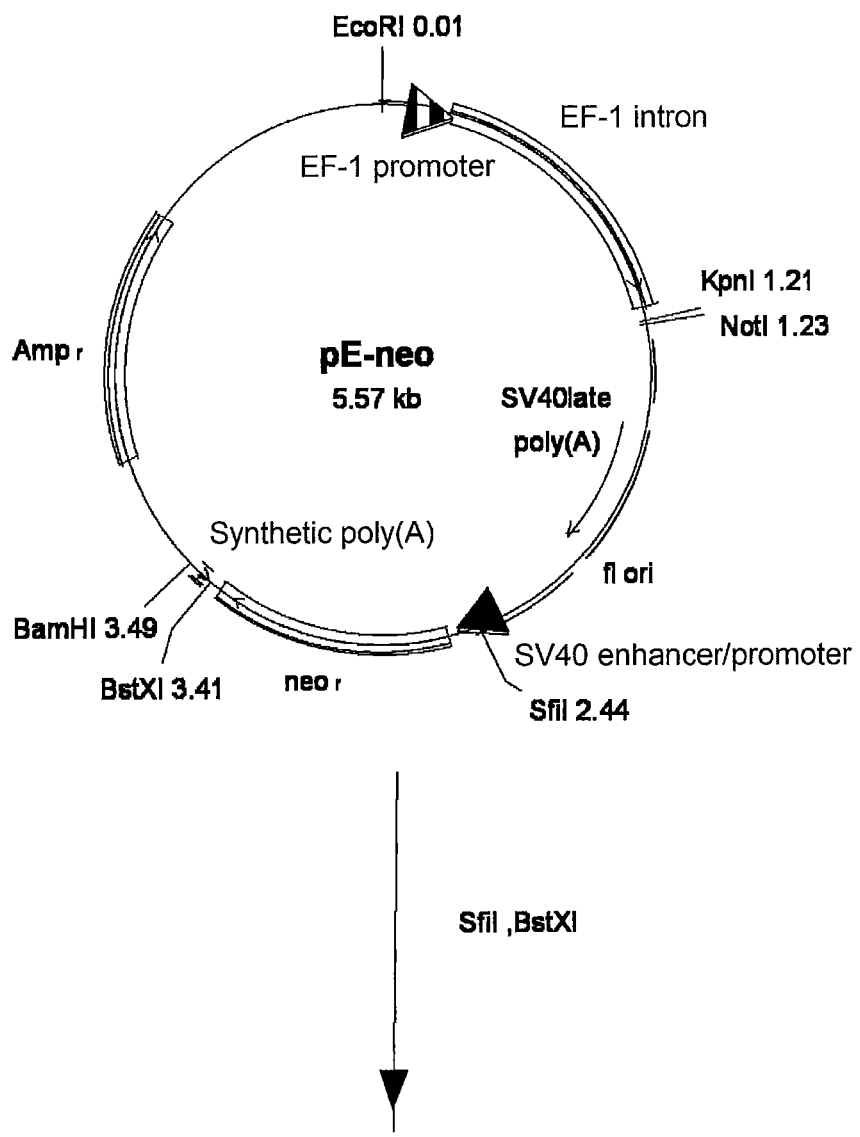
Figure 2:
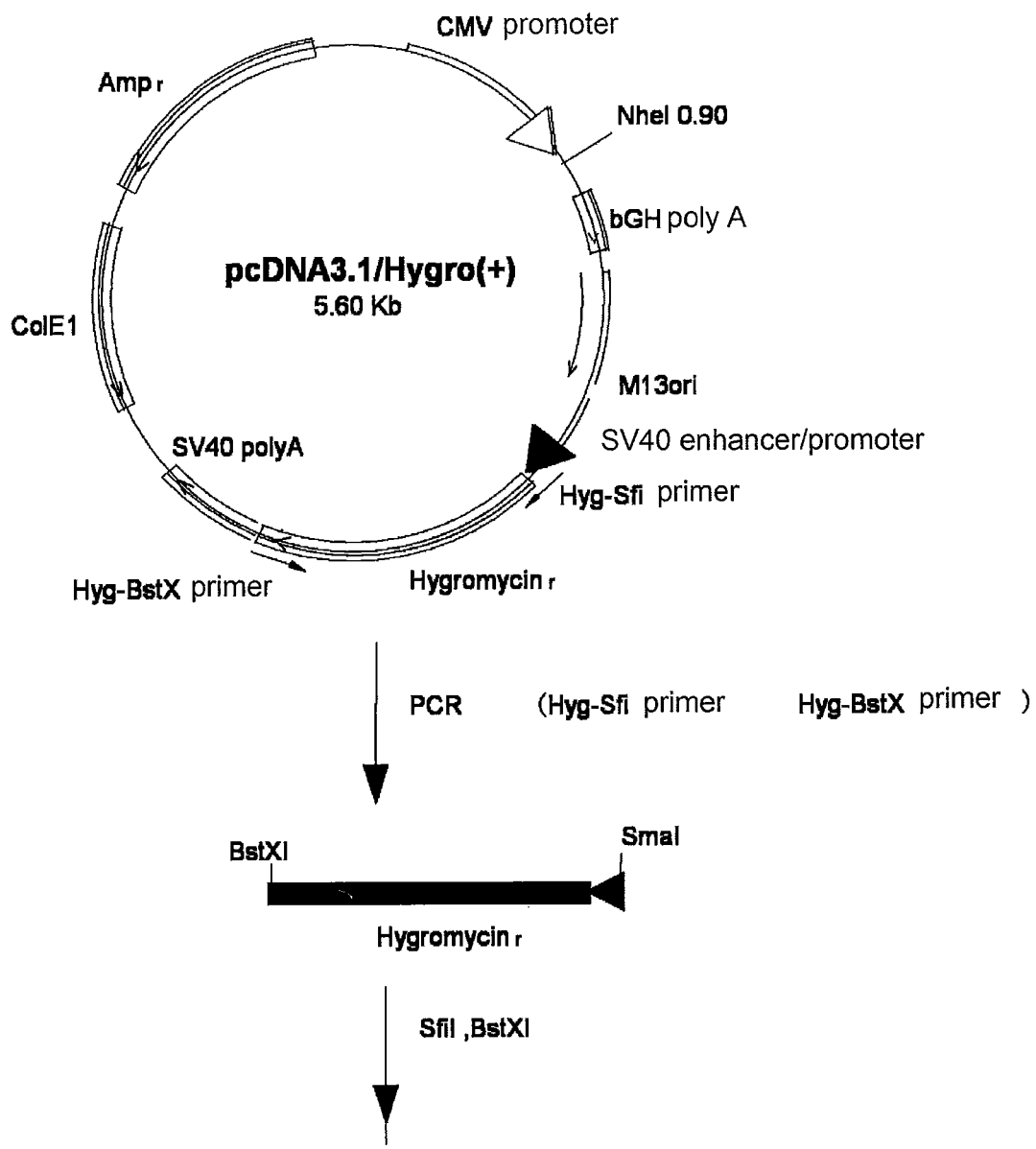
Figures 2, 3:
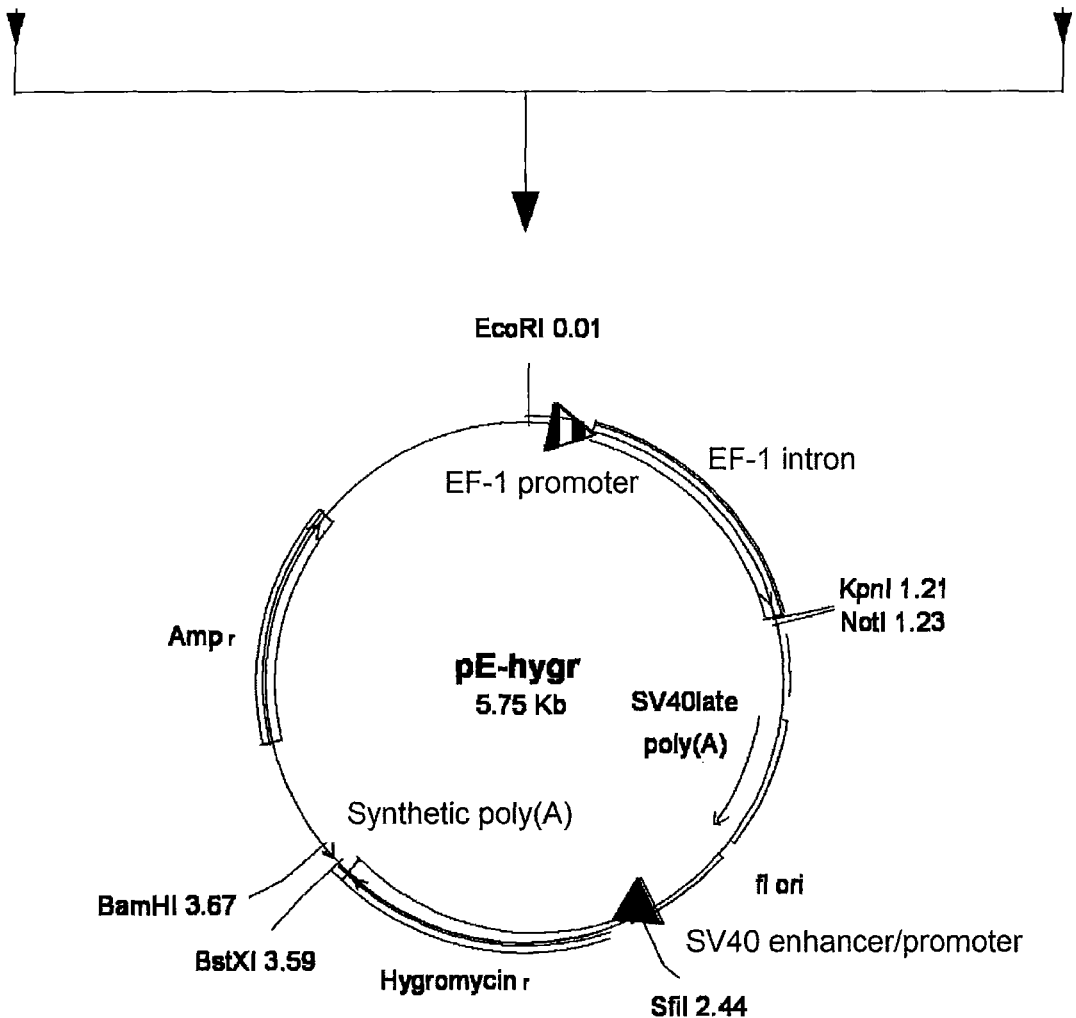

An expression vector pPGKIH (Miyahara M. et. al., J. Biol. Chem. 275, 613-618(2000)) was digested with restriction enzymes (XhoI and BamHI) to cut out a DNA fragment consisting of a nucleotide sequence IRES-Hygr-mPGKpA, which included an internal ribosome entry site (IRES) derived from mouse encephalomyocarditis virus (EMCV), a hygromycin resistance gene (Hygr gene), and the polyadenylation region (mPGKpA) of mouse phosphoglycerate kinase (mPGK)(SEQ ID NO:15; from the 5' end, the region consisting of nucleotides 1-6 represents a "XhoI site"; the region consisting of nucleotides 120-715 and nucleotides 716-718 (atg) that follow represents a "nucleotide sequence including the internal ribosome entry site derived from the 5' untranslated region of mouse encephalomyocarditis virus"; the region consisting of nucleotides 716-1741 including in itself the nucleotides 716-718 (atg) represents the "nucleotide sequence encoding a hygromycin resistance gene"; the region consisting of nucleotides 1747-2210 represents a "nucleotide sequence including the polyadenylation region of mouse phosphoglycerate kinase"; and the region at the 3' end consisting of six nucleotides (nucleotides 2211-2216) represents a "BamHI site"). (Besides, the amino acid sequence corresponding to the Hygrr gene is set forth as SEQ ID NO:16). This DNA fragment was inserted into pBluescript SK(-)(Stratagene) between its XhoI and BamHI sites, and the resulting product was designated pBSK(IRES-Hygr-mPGKpA)(FIG. 3-1).

A DNA fragment containing part of the IRES of EMCV was amplified by PCR using pBSK (IRES-Hygr-mPGKpA), as a template, and primer IRES5' (SEQ ID NO:17) and primer IRES3' (SEQ ID NO:18). This fragment then was digested with restriction enzymes (XhoI) and HindIII) and inserted into pBSK(IRES-Hygr-mPGKpA) between its XhoI and HindIII sites, and the resulting product was designated pBSK(NotI-IRES-Hygr-mPGKpA) (FIG. 3-2). pBSK(NotI-IRES-Hygro-mPGKpA) was digested with restriction enzymes (NotI and BamHI) and inserted into the pE-hygr vector between its NotI and BamHI sites, and the resulting product was designated plasmid pE-IRES-Hygr (FIG. 3-3).

Figures 1, 3:
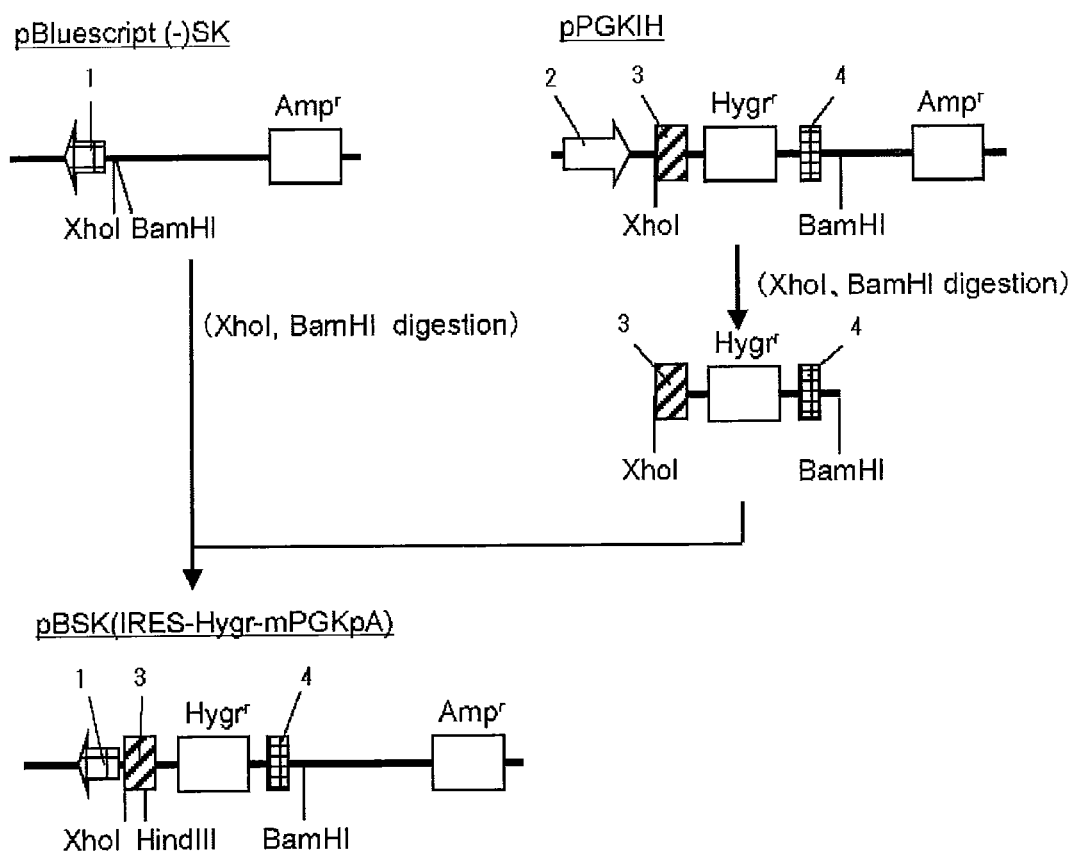
Figures 2, 3:
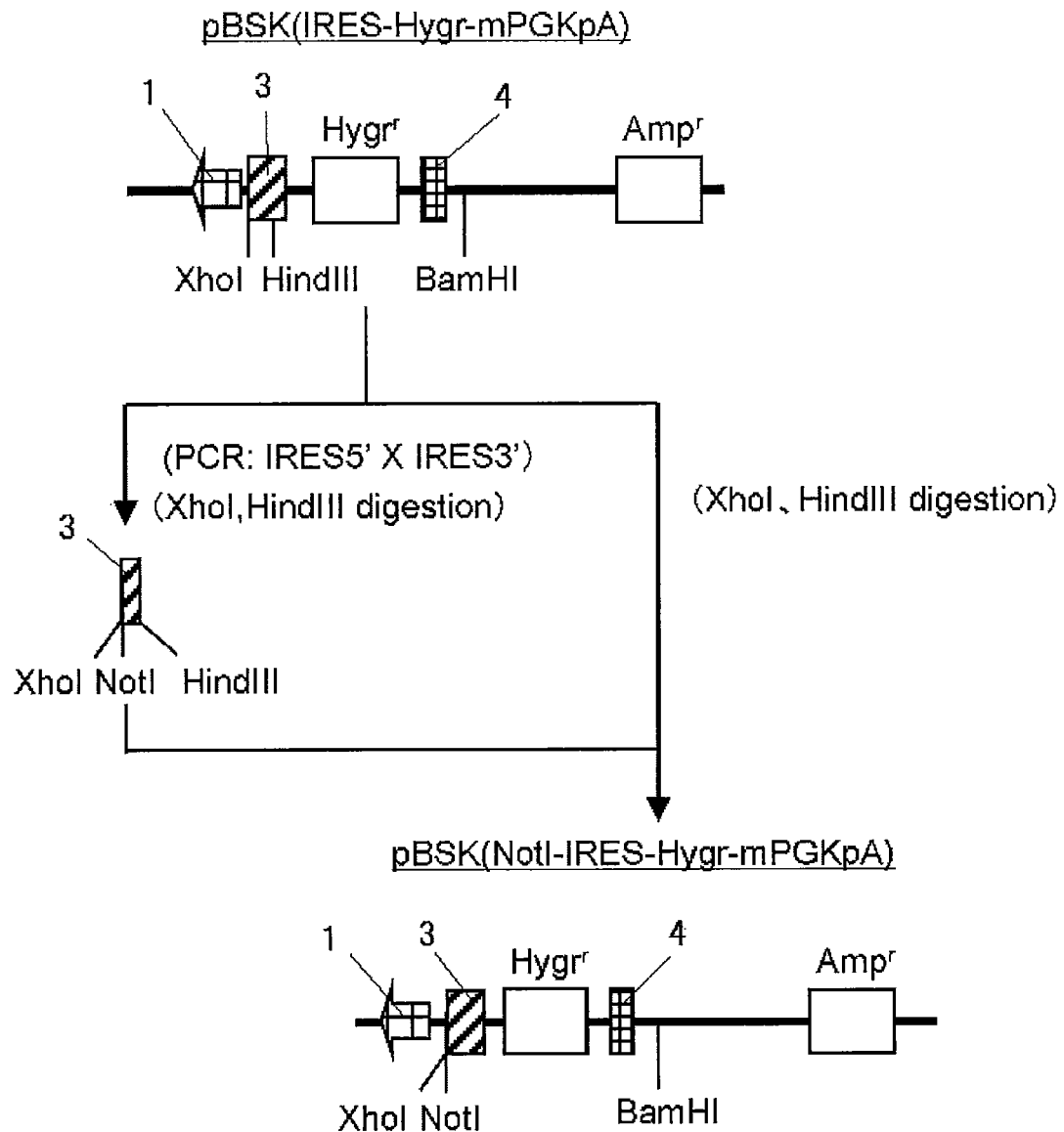
Figure 3:
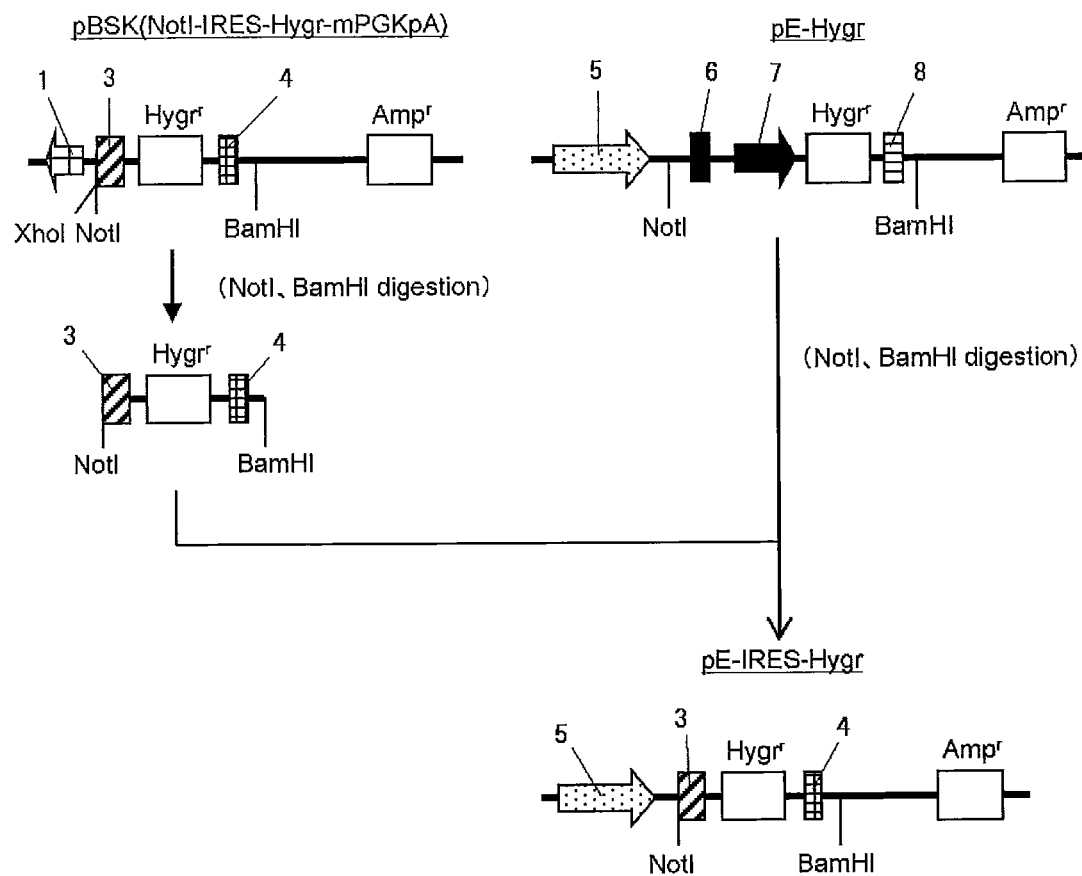
Figures 3, 4:
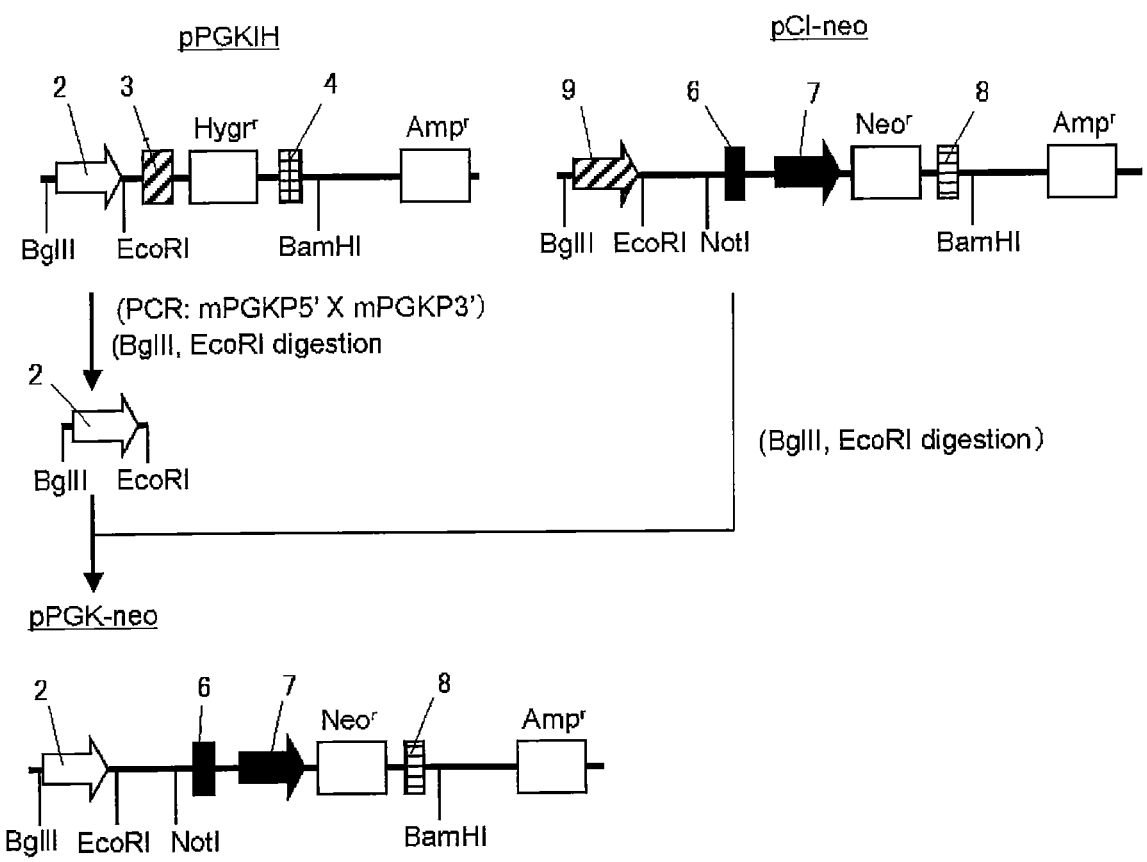
Figures 3, 4, 5:
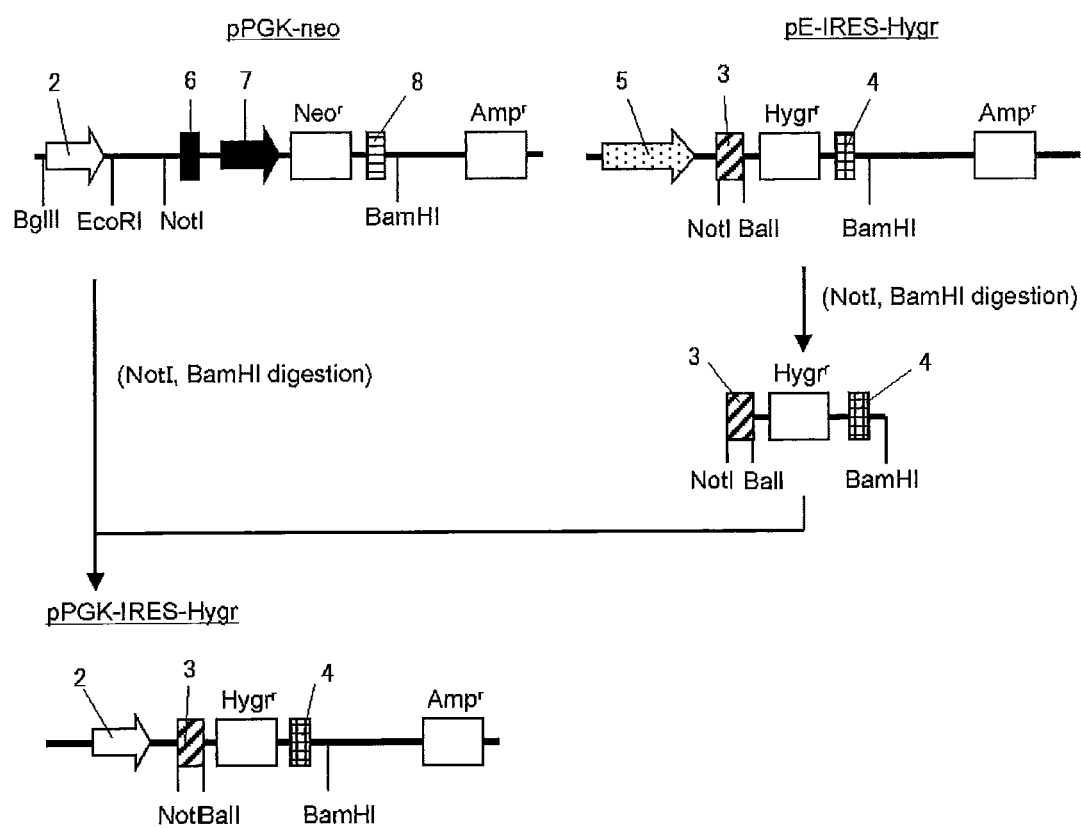

Using the expression vector pPGKIH, as a template, and primer mPGKP5' (SEQ ID NO:19) and primer mPGKP3' (SEQ ID NO:20), PCR was performed to amplify a DNA fragment consisting of a nucleotide sequence including the promoter region of mPGK (mPGKp)(SEQ ID NO:21, from the 5' end, nucleotides 4-9 represents a "BglII site", the region that follows consisting of nucleotides 10-516 represents a "nucleotide sequence including the promoter region of mouse phosphoglycerate kinase (mPGKp)", and the region that follows consisting of nucleotides 524-529 represents an "EcoRI site"). This DNA fragment then was digested with restriction enzymes (BglII and EcoRI) and inserted into pCI-neo (Promega) between its BglII and EcoRI sites, and the resulting product was designated pPGK-neo (FIG. 3-4). pE-IRES-Hygr was digested with restriction enzymes (NotI and BamHI) to cut out a DNA fragment (IRES-Hygr), and this was inserted into pPGK-neo between its NotI and BamHI sites. The resulting product was designated pPGK-IRES-Hygr (FIG. 3-5).

cDNA was prepared from CHO-K1 cells, and using it, as a template, and primer GS5' (SEQ ID NO:22) and primer GS3' (SEQ ID NO:23), PCR was performed to amplify a DNA fragment including the GS gene. The DNA fragment was digested with restriction enzymes (BalI and BamHI) and inserted into pPGK-IRES-Hygr between its BalI and BamHI sites. The resulting product was designated pPGK-IRES-GS-ΔpolyA (FIG. 3-6).

Using pCAGIPuro (Miyahara M. et. al., J. Biol. Chem. 275, 613-618 (2000)), as a template, and primer puro5' (SEQ ID NO:24) and primer puro3' (SEQ ID NO:25), PCR was performed to amplify a nucleotide sequence including a puromycin resistance gene (puro$^r$ gene) (SEQ ID NO:26, from the 5'-end, the region consisting of nucleotides 2-7 represents a "AflII" site, the region that follows consisting of nucleotides 8-607 represents a "nucleotide sequence encoding the puromycin resistance gene (puro$^r$ gene)", and the region that follows consisting of nucleotides 608-619 represents a "BstXI site") (Besides, the amino acid sequence corresponding to the puro$^r$ gene is set forth as SEQ ID NO:27). This DNA fragment was digested with restriction enzymes (AflII and BstXI) and inserted into the expression vector pE-neo between its AflII and BstXI sites. The resulting product was designated pE-puro (FIG. 3-7).

Using pE-puro, as a template, and primer SV40polyA5' (SEQ ID NO:28) and primer SV40polyA3' (SEQ ID NO:29), PCR was performed to amplify a DNA fragment including SV40 late polyadenylation region. This DNA fragment then was digested with restriction enzymes (NotI and HpaI) and inserted into pE-puro between its NotI and HpaI sites. The resulting product was designated pE-puro (XhoI) (FIG. 3-8). pPGK-IRES-GS-ΔpolyA was digested with restriction enzymes (NotI and XhoI) to cut out a DNA fragment including the IRES-GS region, which then was inserted into the expression vector pE-puro(XhoI) between its NotI and XhoI sites. The resulting product was designated pE-IRES-GS-puro (FIG. 3-9).

[Construction of pE-mIRES-GS-puro]

Using the expression vector pE-IRES-GS-puro, as a template, and primer mIRES-GS5' (SEQ ID NO:30) and primer mIRES-GS3' (SEQ ID NO:31), PCR was performed to amplify a region from the IRES to GS of EMCV, and thus a DNA fragment was amplified in which the second start codon (ATG) from the 5' end of the IRES of EMCV was destroyed by introduction of a mutation. Using the expression vector pE-IRES-GS-puro, as a template, and the DNA fragment and the above-mentioned primer IRES5', PCR was performed to amplify a DNA fragment including a region from IRES to GS. This DNA fragment was digested with restriction enzymes (NotI and PstI), and a DNA fragment thus cut out was inserted into the expression vector pE-IRES-GS-puro between its NotI and PstI sites. The resulting product was designated pE-mIRES-GS-puro (FIG. 4).

[Construction of pE-mIRES-GS]

Using the expression vector pE-neo, as a template, and primer SV40polyA5'-2 (SEQ ID NO:32) and primer SV40polyA3'-2 (SEQ ID NO:33), PCR was performed to amplify a DNA fragment including the SV40 late polyA region. This DNA fragment was digested with restriction enzymes (XhoI and BamHI) and inserted into pE-mIRES-GS-puro between its XhoI and BamHI sites. The resulting product was designated pE-mIRES-GS (FIG. 5).

[Construction of Human Thyroid Stimulating Hormone (hTSH) Expression Vector]

[Construction of pE-mIRES-GS-mNeo]

Figures 3, 4, 5, 6:
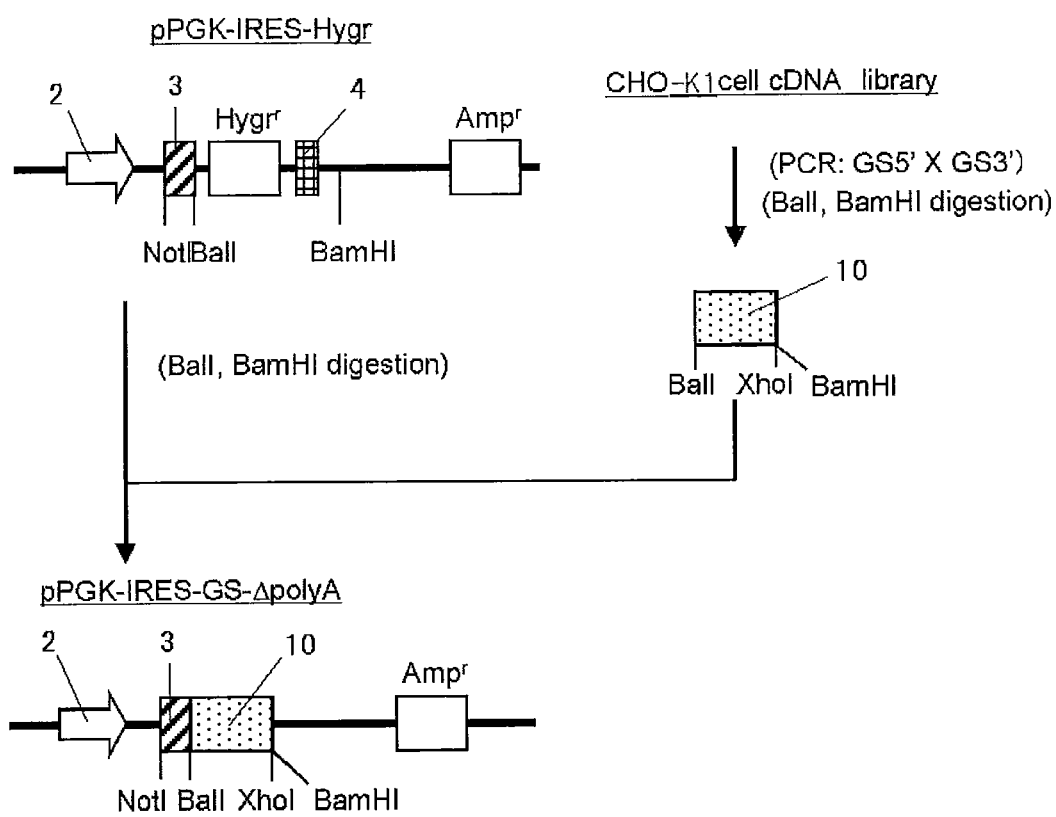

Using pCI-neo (Invitrogen), as a template, and primer mNeoA5' (SEQ ID NO:34) and primer mNeoA3' (SEQ ID NO:35), PCR was performed to amplify the full length of this plasmid, and through self-ligation, plasmid pCI-mNeo containing E182D mutant-type neomycin resistance gene (mNeo$^r$ gene) was constructed. Using the pCI-mNeo vector, as a template, and primer mNeoB5' (SEQ ID NO:36) and primer mNeoB3' (SEQ ID NO:37), PCR was performed to amplify a DNA fragment containing mNeo$^r$ gene. This DNA fragment was digested with a restriction enzyme (EagI) and inserted into pUC57-IE1 (Gene Scrip) at its NotI site. The resulting product was designated pUC57-IE1-mNeo. Using pCI-neo, as a template, and primer mNeoC5' (SEQ ID NO:38) and primer mNeoC3' (SEQ ID NO:39), PCR was performed to amplify a region containing a 3' region of the neomycin resistance gene (neon gene) and the synthetic poly A signal, and the product was used as a megaprimer (neo-polyA). Then, using pUC57-IE1-mNeo, as a template, and primer mNeoD5' (SEQ ID NO:40) and the megaprimer (neo-polyA), PCR was performed to amplify a region containing the mNeo$^r$ gene and the synthetic poly A signal. The DNA fragment thus obtained was digested with restriction enzymes (AflII and BamHI), and inserted into pE-mIRES-GS-puro between its AnII and BamHI sites. The product thus obtained was designated pE-mIRES-GS-mNeo (FIG. 6).

Figures 3, 4, 5, 6, 7:
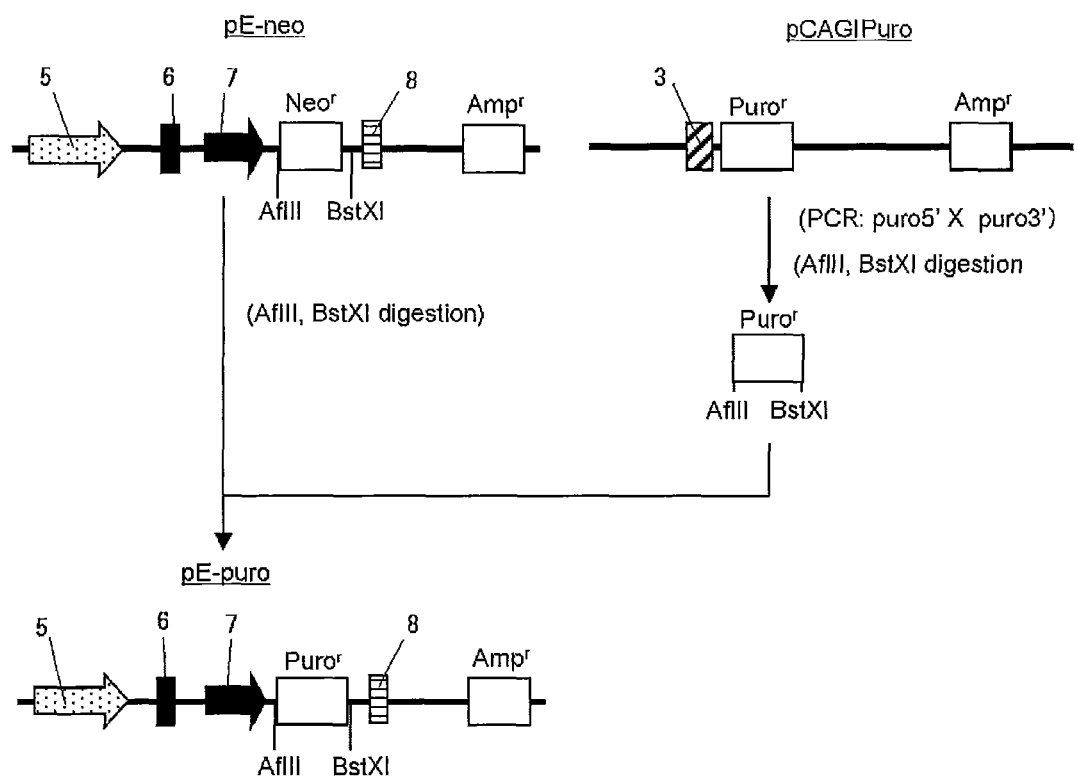

[Construction of pBlue-EF1/mIRES-mNeo]

pE-mIRES-GS-mNeo was digested with a restriction enzyme (EcoRI) to cut out a DNA fragment containing the elongation factor 1 promoter (EF-1p), the mutant-type internal ribosome entry site (mIRES) and part of the glutamine synthetase (GS). This DNA fragment was inserted into pBluescript SK(+) (Stratagene) at its EcoRI site. The product thus obtained was designated pBlue-EF1/mIRES (FIG. 7).

pE-mIRES-GS-mNeo was digested with a restriction enzyme (PvuI) to cut out a DNA fragment containing the mutant-type neomycin resistance gene (mNeo$^r$ gene) and a DNA fragment containing the SV40 late polyA region. Using the DNA fragment containing the SV40 late polyA region, as a template, and primer SVpA-Mega-F (SEQ ID NO:41) and primer SVpA-BstXI-R (SEQ ID NO:42), PCR was performed to amplify the same DNA fragment containing the SV40 polyA region. By ligating this gene fragment and the above-mentioned DNA fragment containing the mNeo$^r$ gene, a DNA fragment was prepared which contained SV40 late polyA region downstream of the mNeo$^r$ gene. This DNA fragment was digested with a restriction enzyme (BstXI), and inserted into pBlue-EF1/mIRES between its BstXI sites. The product thus obtained was designated pBlue-EF1/mIRES-mNeo (FIG. 7).

[Construction of pBlue-EF1/SVpA]

Figures 3, 4, 5, 6, 7, 8:
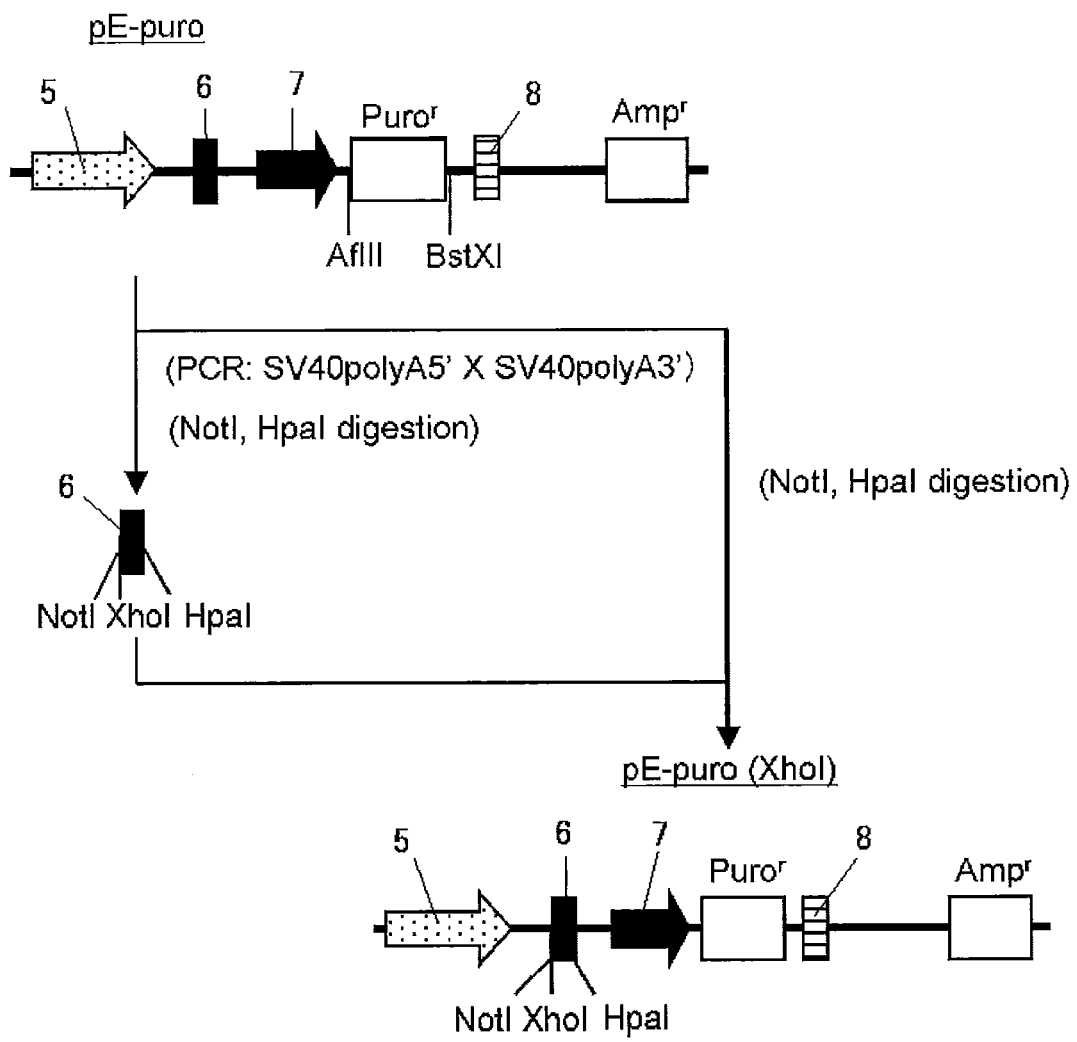

Using the expression vector pE-mIRES-GS-mNeo, as a template, and primer SVpA-Not-F (SEQ ID NO:43) and primer SVpA-BstXI-R (SEQ ID NO:44), PCR was performed to amplify a DNA fragment containing the SV40 late polyA region. This DNA fragment was digested with restriction enzymes (NotI and BstXI), and inserted into pBlue-EF1/mIRES between its NotI and BstXI sites. The product thus obtained was designated pBlue-EF1/SVpA (FIG. 8).

[Construction of pE-mDHFR31]

Figures 3, 4, 5, 6, 7, 8, 9:
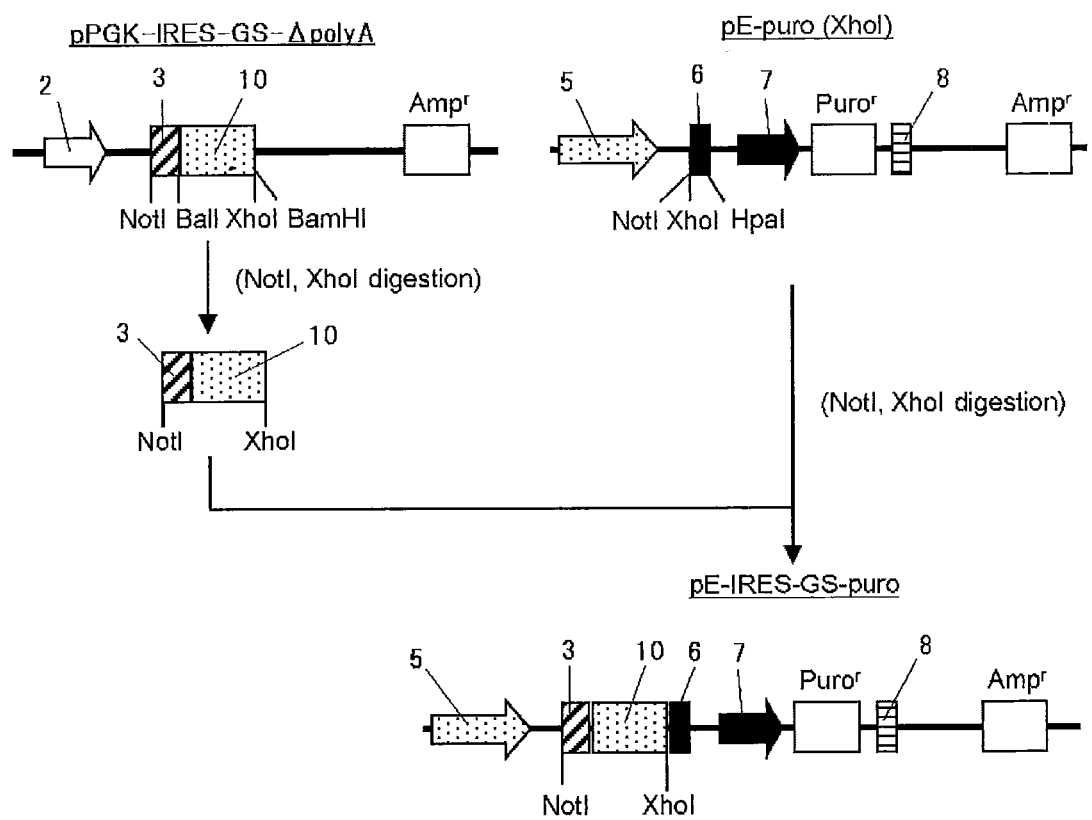
Figure 4:
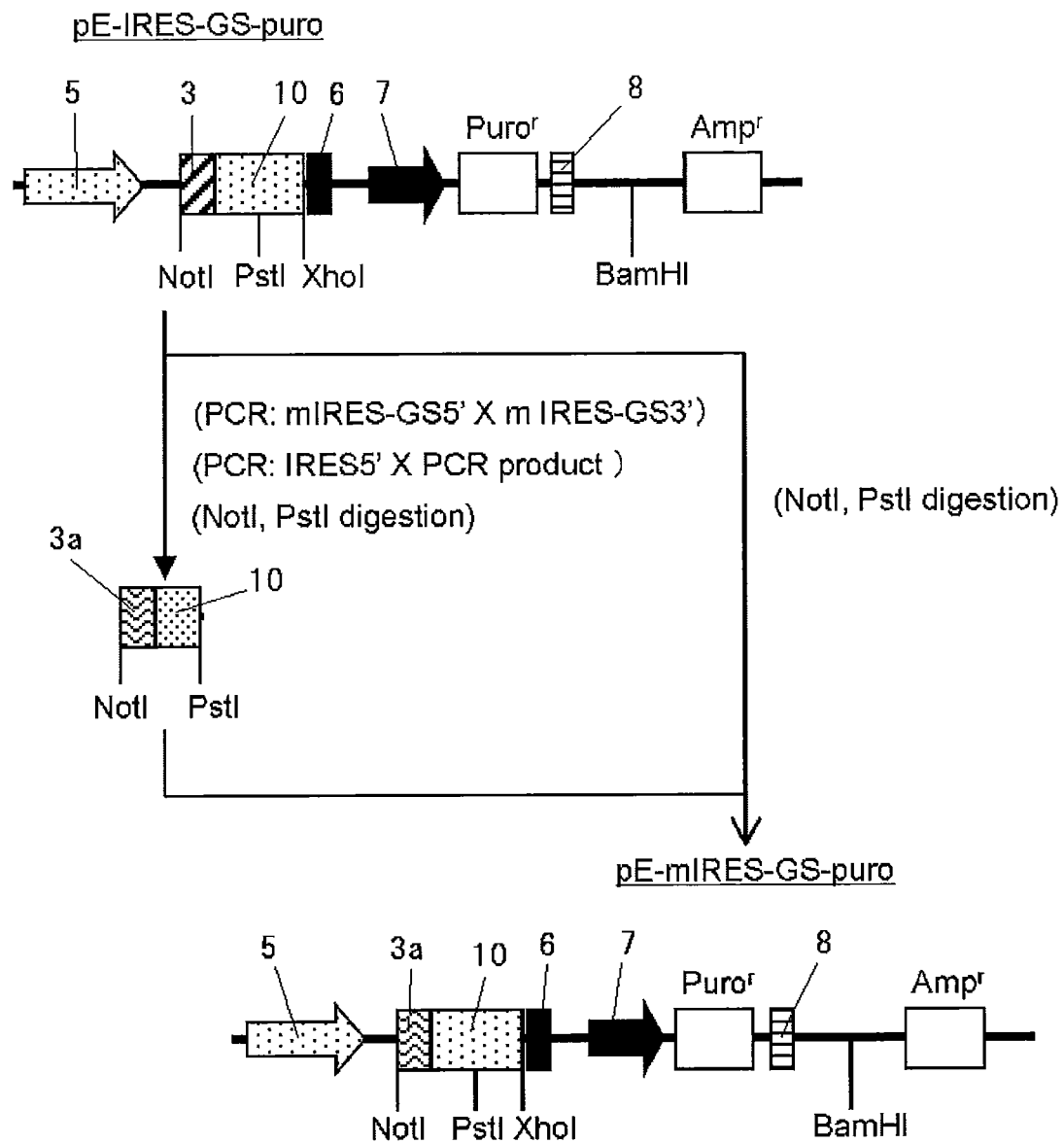
Figure 5:
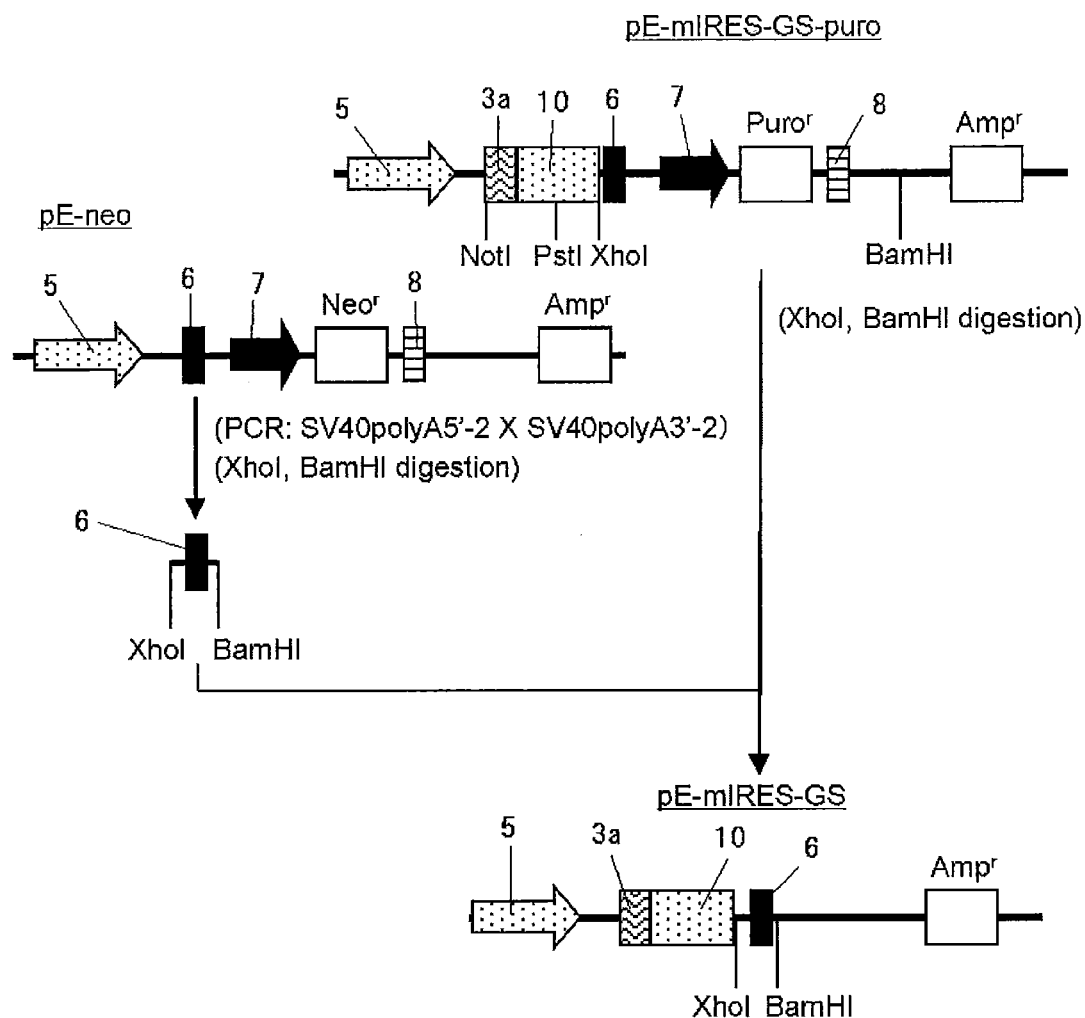
Figure 6:
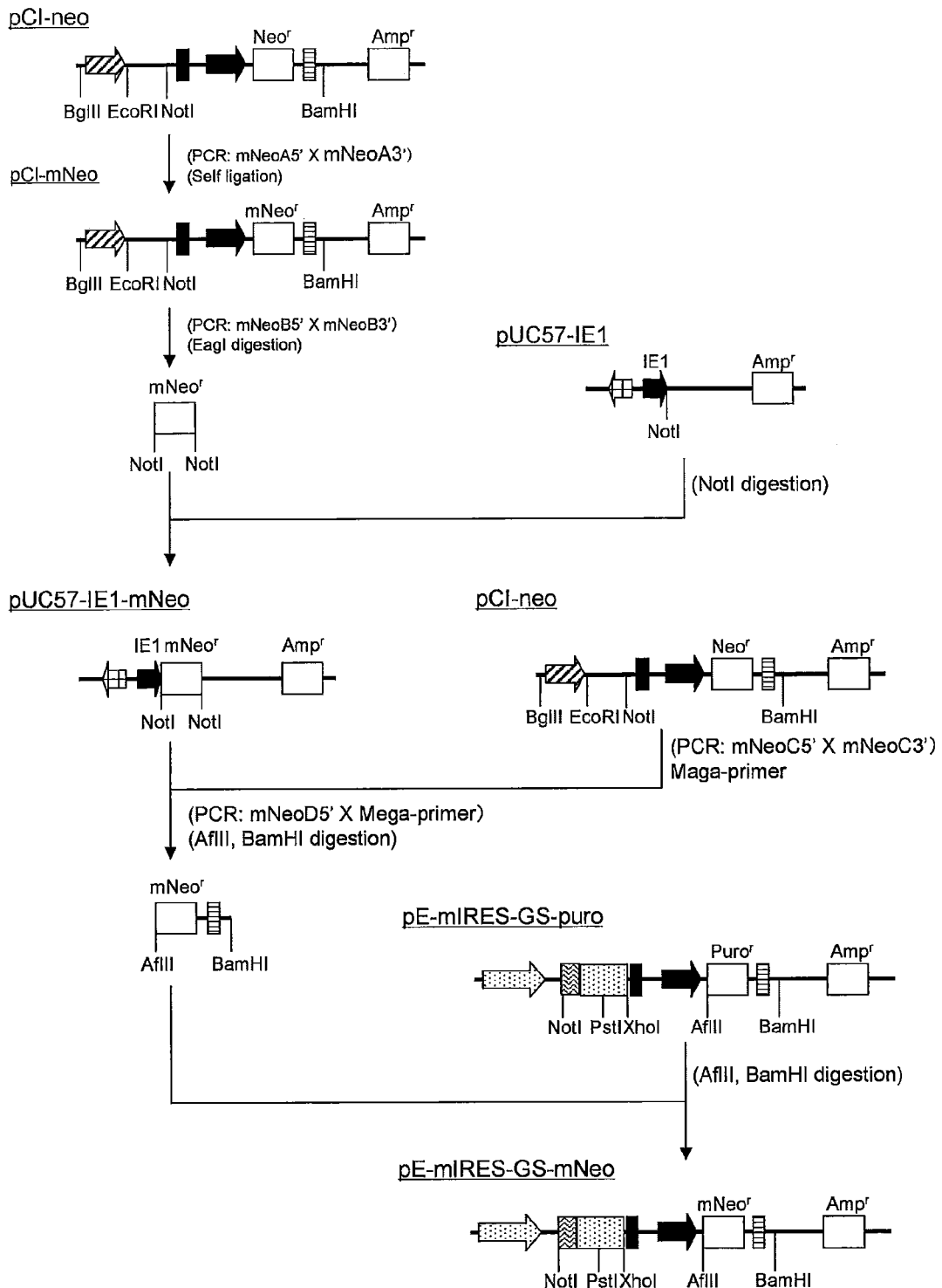
Figure 7:
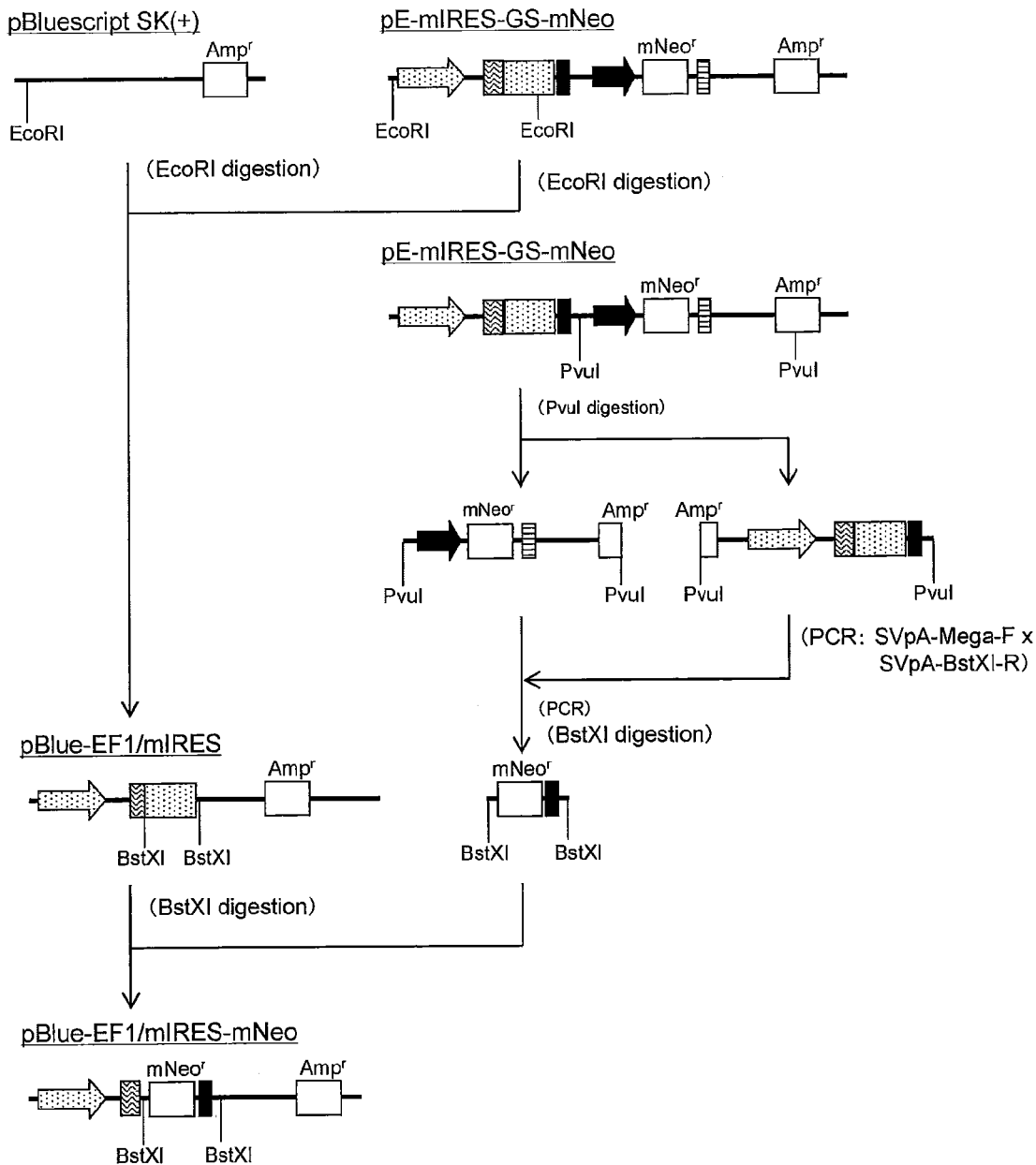
Figure 8:
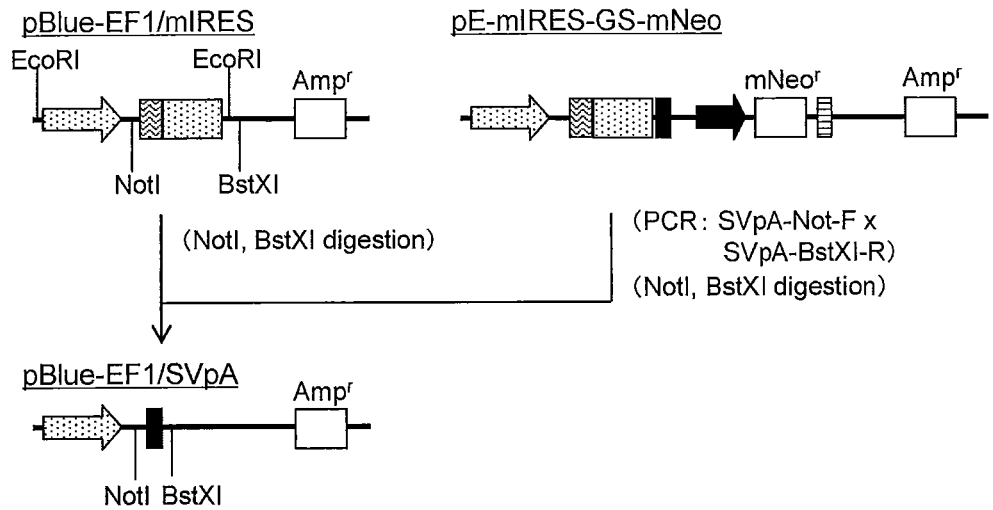
Figure 9:
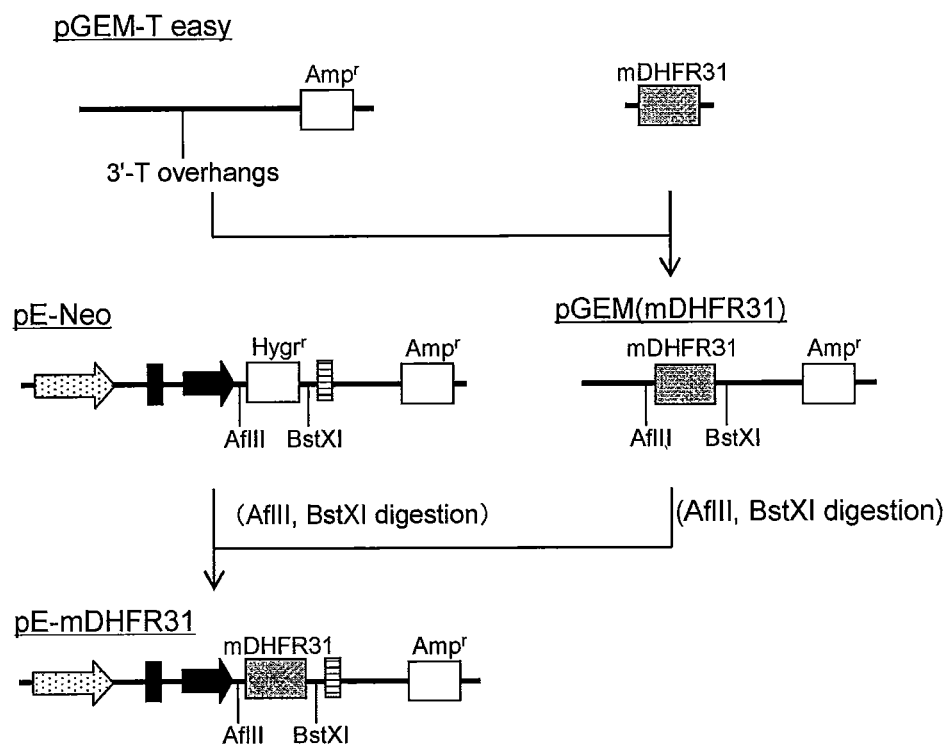

A DNA (SEQ ID NO:45) was synthesized that contained a mutant-type DHFR (F31W) gene (mDHFR31)(SEQ ID NO:11), a gene in which phenylalanine at position 31 from the N-terminus of the mouse wild-type DHFR has been replaced with tryptophan. This DNA was inserted into pGEM-T easy vector (Promega) at its 3'-T overhang portion, and the resulting product was designated pGEM(mDHFR31). pGEM(mDHFR31) then was digested with restriction enzymes (AflII and BstXI) to cut out a DNA fragment containing the mutant-type DHFR(F31W), and this DNA fragment was inserted into pE-neo between its AflII and BstXI sites. The product thus obtained was designated pE-mDHFR31 (FIG. 9).

[Construction of pCI-Neo(hTSHα-WAP3'UTR) and pCI-Neo(hTSHβ-WAP3'UTR)]

A DNA containing a gene for the α chain of human thyroid stimulating hormone (hTSHα) (SEQ ID NO:46, in which, from the 5' end, the region consisting of nucleotides 1-6 represents a "MluI site", the region consisting of nucleotides 14-364 represents the "nucleotide sequence encoding hTSHα chain", and the region that follows consisting of nucleotides 365-372 represents a "NotI" site) and a DNA containing a gene for the β chain of human thyroid stimulating hormone (hTSHβ) (SEQ ID NO:47, in which, from the 5' end, the region consisting of nucleotides 1-6 represents a "MluI site", the region consisting of nucleotides 14-433 represents the "nucleotide sequence encoding TSHβ chain", and the region that follows consisting of nucleotides 434-441 represents a "NotI site") were synthesized, and they were respectively inserted into pUC57 to prepare pUC57-hTSHα, and pUC57-hTSHβ (Shanghai ShineGene Molecular Biotech). Separately, a DNA (SEQ ID NO:48) was synthesized containing the 3' untranslated region of rabbit whey acidic protein (WAP), and then was incorporated into pUC57 to prepare pUC57-WAP3'UTR (Shanghai Shine-Gene Molecular Biotech).

Using pUC57-hTSHα containing hTSHα gene, as a template, and primer TSHα5' (SEQ ID NO:49) and primer TSHα3' (SEQ ID NO:50), PCR was performed to amplify a DNA fragment containing TSHα gene, and the DNA fragment thus obtained was used as a megaprimer TSHα. Separately, using a DNA containing hTSHβ gene, as a template, and primer TSHβ5' (SEQ ID NO:51) and primer TSHβ3' (SEQ ID NO:52), PCR was performed to amplify a DNA fragment containing TSHβ gene. This DNA fragment thus obtained was used as a megaprimer TSHβ.

Figures 1, 10:
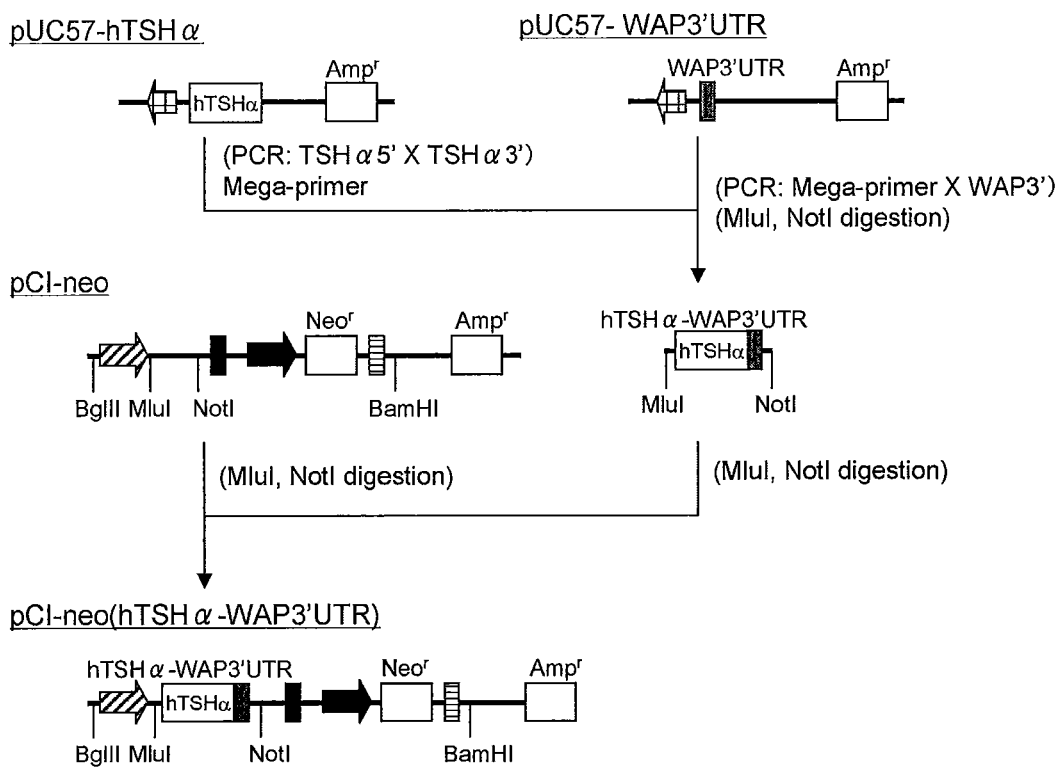
Figures 2, 10:
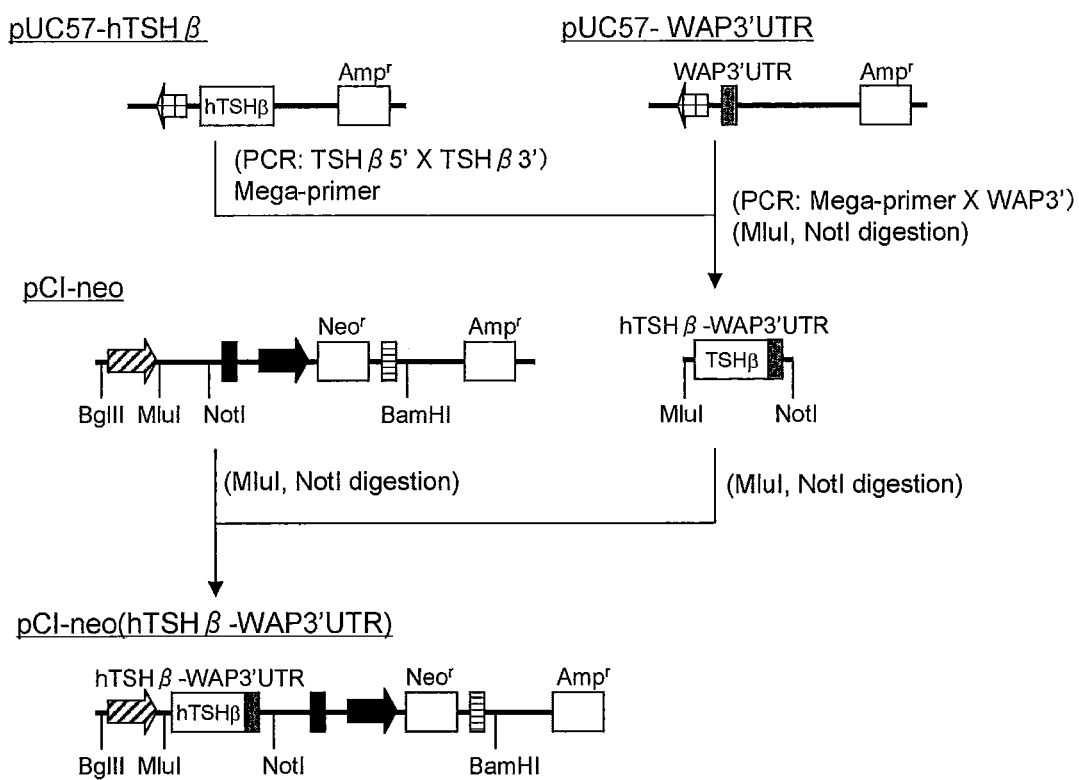

Using pUC57-WAP3'UTR containing WAP3'UTR, as a template, and the megaprimer TSHα and primer WAP3' (SEQ ID NO:53), PCR was performed to amplify a DNA fragment containing the TSHα gene and WAP3'UTR downstream of it (hTSHα-WAP3'UTR). Separately, using pUC57-WAP3'UTR containing WAP3'UTR, as a template, and the megaprimer TSHβ and primer WAP3', PCR was performed to amplify a DNA fragment containing TSHβ gene and WAP3'UTR downstream of it (hTSHβ-WAP3'UTR). Each of the fragments thus obtained was digested with restriction enzymes (MluI and NotI), and inserted into pCI-neo between its MluI and NotI sites to prepare pCI-neo(hTSHα-WAP3'UTR) and pCI-neo(hTSHβ-WAP3'UTR) (FIGS. 10-1, and 10-2).

Figure 11:
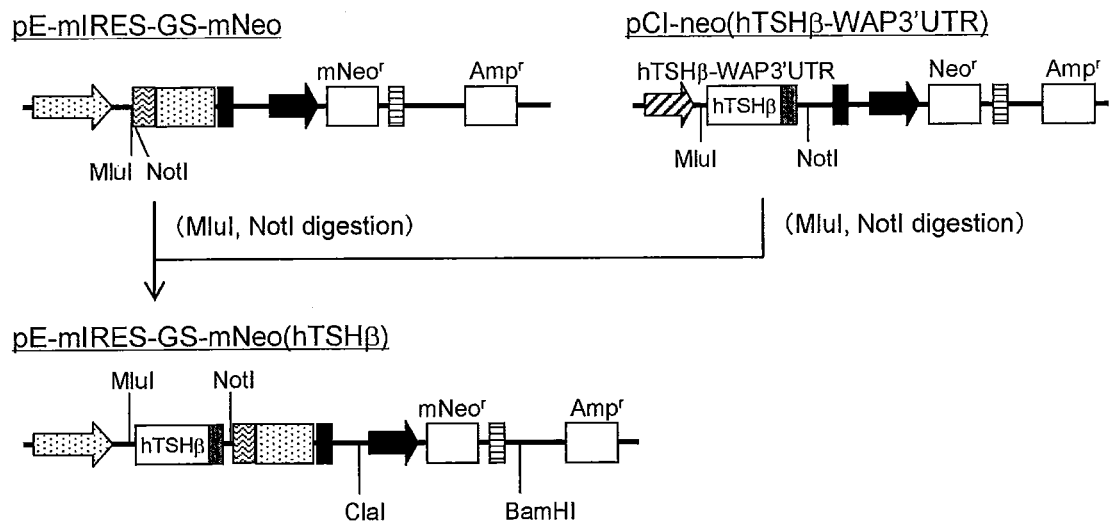
FIG. 11 A diagram illustrating a flow of the method for construction of pE-mIRES-GS-mNeo FIG. 12 A diagram illustrating a flow of the method for construction of pBlue-EF1/mIRES-mNeo(hTSHα)

[Construction of pE-mIRES-GS-mNeo(hTSHβ)]

pCI-neo(hTSHβ-WAP3'UTR) was digested with restriction enzymes (MluI and NotI) to cut out a DNA fragment containing the hTSHβ gene and WAP3'UTR. This DNA fragment was inserted into pE-mIRES-GS-mNeo between its MluI and NotI sites. The product thus obtained was designated pE-mIRES-GS-mNeo(hTSHβ) (FIG. 11).

Figure 12:
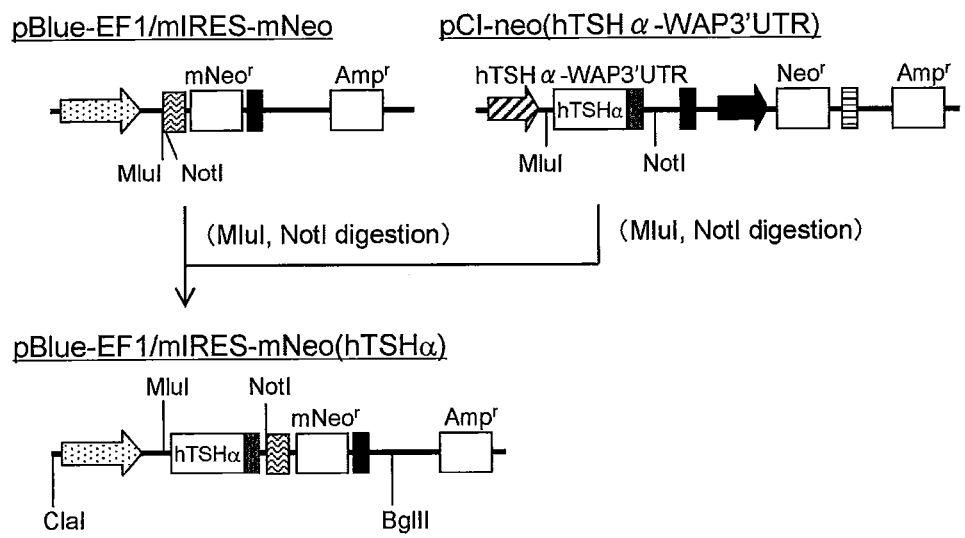

[Construction of pBlue-EF1/mIRES-mNeo(hTSHα)]

pCI-neo(hTSHα-WAP3'UTR) was digested with restriction enzymes (MluI and NotI) to cut out a DNA fragment containing hTSHα gene and WAP3'UTR. This DNA fragment was inserted into pBlue-EF1/mIRES-mNeo between its MluI and NotI sites. The product thus obtained was designated pBlue-EF1/mIRES-mNeo(hTSHα) (FIG. 12).

Figure 13:
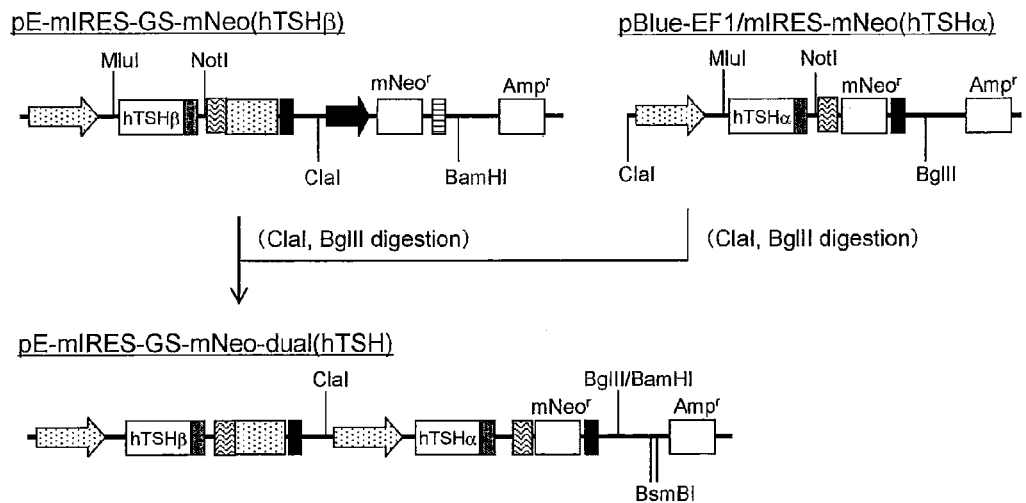
FIG. 13 A diagram illustrating a flow of the method for construction of pE-mIRES-GS-mNeo-dual(hTSH)

[Construction of pE-mIRES-GS-mNeo-dual(hTSH)]

pBlue-EF1/mIRES-mNeo(hTSHα) was digested with restriction enzymes (ClaI and BglII) to cut out a DNA fragment containing the elongation factor 1 promoter (EF-1p), hTSHα gene, mIRES, and the mutant-type neomycin resistance gene (mNeo$^r$). This DNA fragment was inserted into pE-mIRES-GS-mNeo(hTSHβ) between its ClaI and BamHI sites. The product thus obtained was designated pE-mIRES-GS-mNeo-dual(hTSH), a vector for expression of human thyroid stimulating hormone (hTSH) (FIG. 13).

[Construction of pE-mIRES-GS-mNeo-Dual+mDHFR31 (hTSH)]

Figure 14:
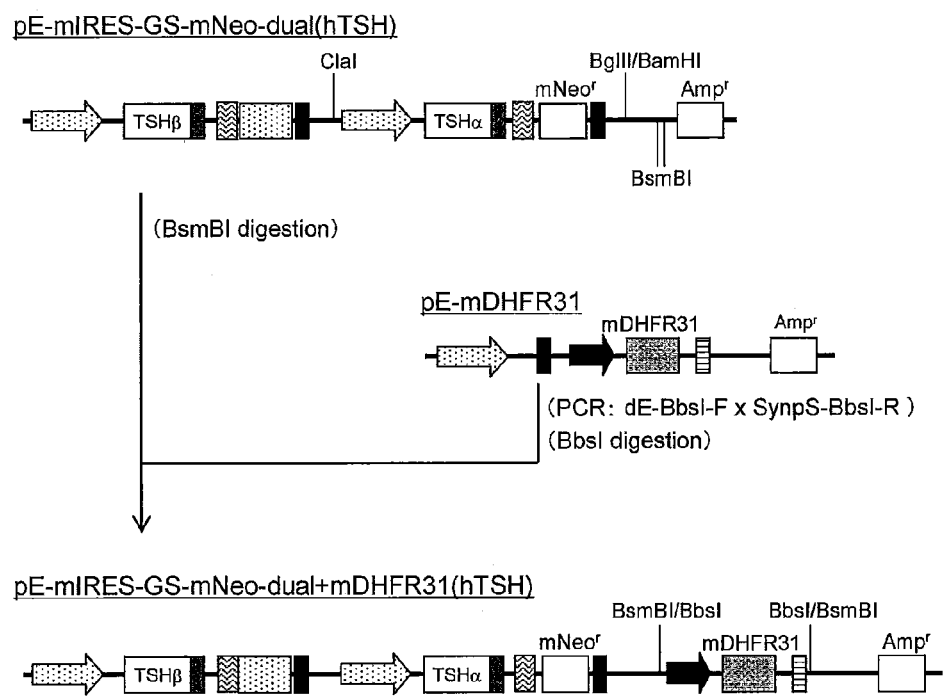
FIG. 14 A diagram illustrating a flow of the method for construction of pE-mIRES-GS-mNeo-dual+mDHFR31 (hTSH)

Using pE-mDHFR31, as a template, and primer dE-BbsI-F (SEQ ID NO:54) and primer SynpA-BbsI-R (SEQ ID NO:55), PCR was performed to amplify a DNA fragment containing SV40 early promoter (SV40 enhancer/promoter), mutant-type DHFR (F31W), and a synthetic polyadenylation signal (a synthesized region for polyadenylation). The DNA fragment thus obtained was digested with a restriction enzyme (BbsI) and inserted into pE-mIRES-GS-mNeo-dual(hTSH) between its BsmBI sites. The product thus obtained was designated pE-mIRES-GS-mNeo-dual+mDHFR31(hTSH), a vector for expression of human thyroid stimulating hormone (hTSH) (FIG. 14).

[Construction of pE-mIRES-GS-mNeo(RTX-H)]

Figure 15:
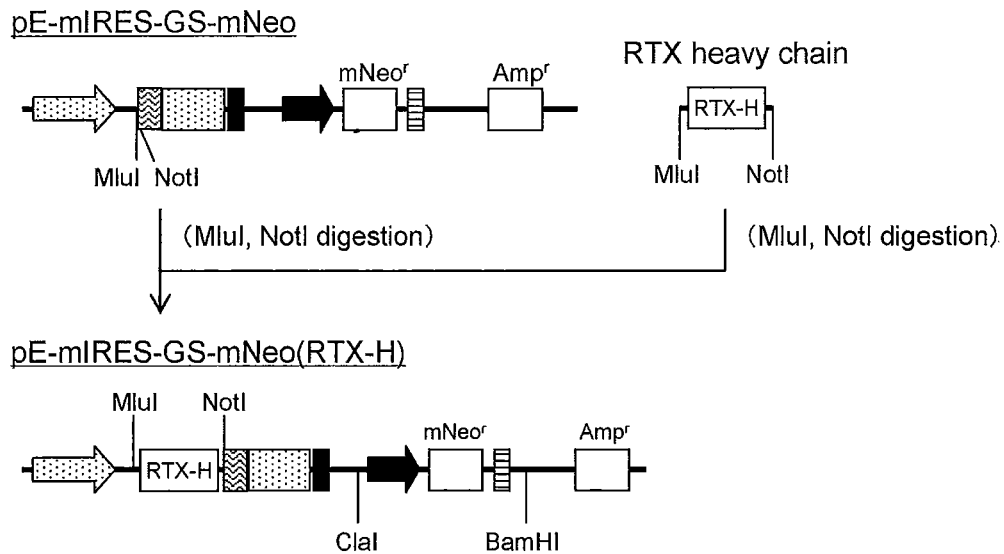
FIG. 15 A diagram illustrating a flow of the method for construction of pE-mIRES-GS-mNeo (RTX-H)

A DNA containing the gene for the heavy chain of rituximab (SEQ ID NO:56; from the 5' end, the region consisting of nucleotides 1-6 represents a "MluI site", the region consisting of nucleotides 18-1430 represents the "nucleotide sequence encoding the heavy chain of rituximab", and the region that follows consisting of nucleotide 1431-1438 represents a "NotI site") was synthesized. This DNA was digested with restriction enzymes (MluI and NotI), and the DNA fragment thus obtained was inserted into pE-mIRES-GS-mNeo between its MluI and NotI sites. The product thus obtained was designated pE-mIRES-GS-mNeo (RTX-H) (FIG. 15).

[Construction of pBlue-EF1/mIRES-mNeo(RTX-L)]

Figure 16:
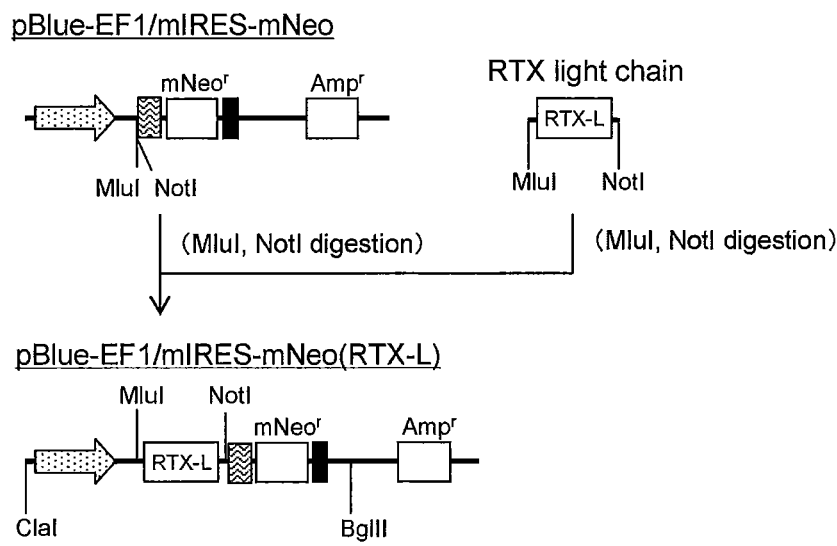
FIG. 16 A diagram illustrating a flow of the method for construction of pBlue-EF1/mIRES-mNeo (RTX-L)

A DNA containing the gene for the light chain of rituximab (SEQ ID NO:57; from the 5' end, the region consisting of nucleotides 1-6 represents a "MluI site", the region consisting of nucleotides 18-725 represents the "nucleotide sequence encoding the light chain of rituximab", and the region that follows consisting of nucleotides 726-733 represents a "NotI site") was synthesized. This DNA was digested with restriction enzymes (MluI and NotI), and the DNA fragment thus obtained was inserted into pBlue-EF1/mIRES-mNeo between its MluI and NotI sites. The product thus obtained was designated pBlue-EF1/mIRES-mNeo (RTX-L) (FIG. 16).

Figure 17:
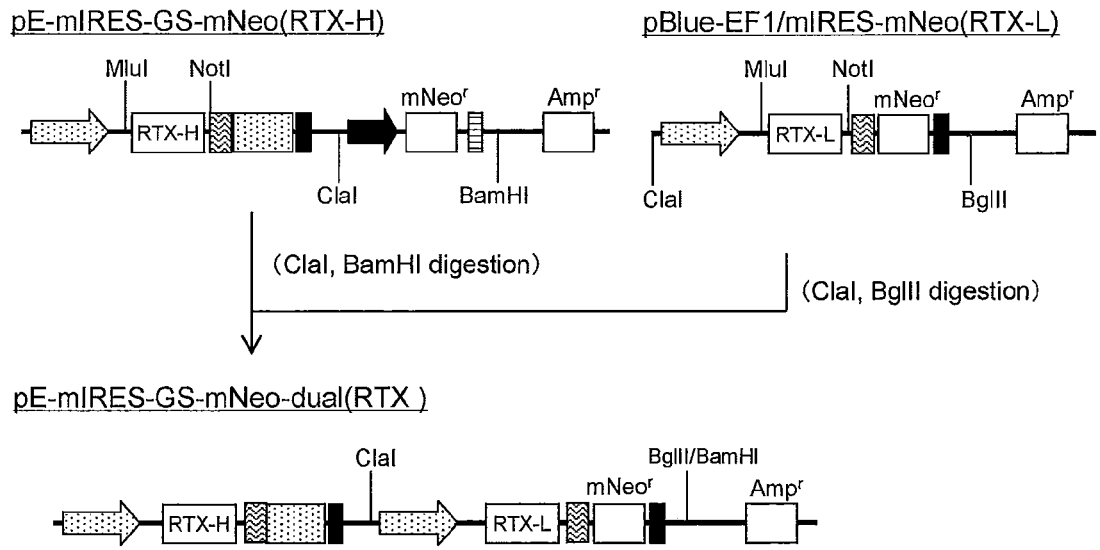
FIG. 17 A diagram illustrating a flow of the method for construction of pE-mIRES-GS-mNeo-dual(RTX)

[Construction of pE-mIRES-GS-mNeo-Dual(RTX)]

pBlue-EF1/mIRES-mNeo(RTX-L) was digested with restriction enzymes (ClaI and BglII), and the DNA fragment obtained was inserted into pE-mIRES-GS-mNeo(RTX-H) between ClaI and BglII sites. The product thus obtained was designated pE-mIRES-GS-mNeo-dual(RTX), a vector for expression of rituximab (FIG. 17).

[Construction of pE-mIRES-GS-dual+mDHFR31(RTX)]

Figures 1, 18:
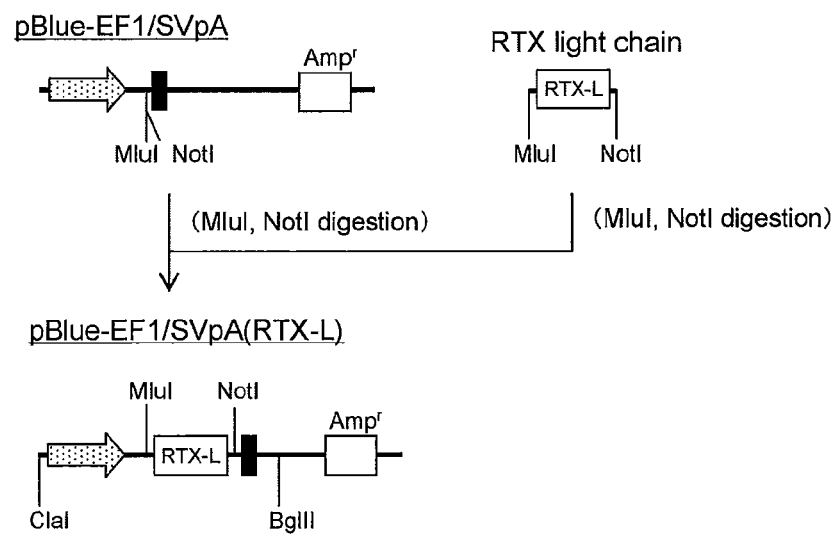
Figures 2, 18:
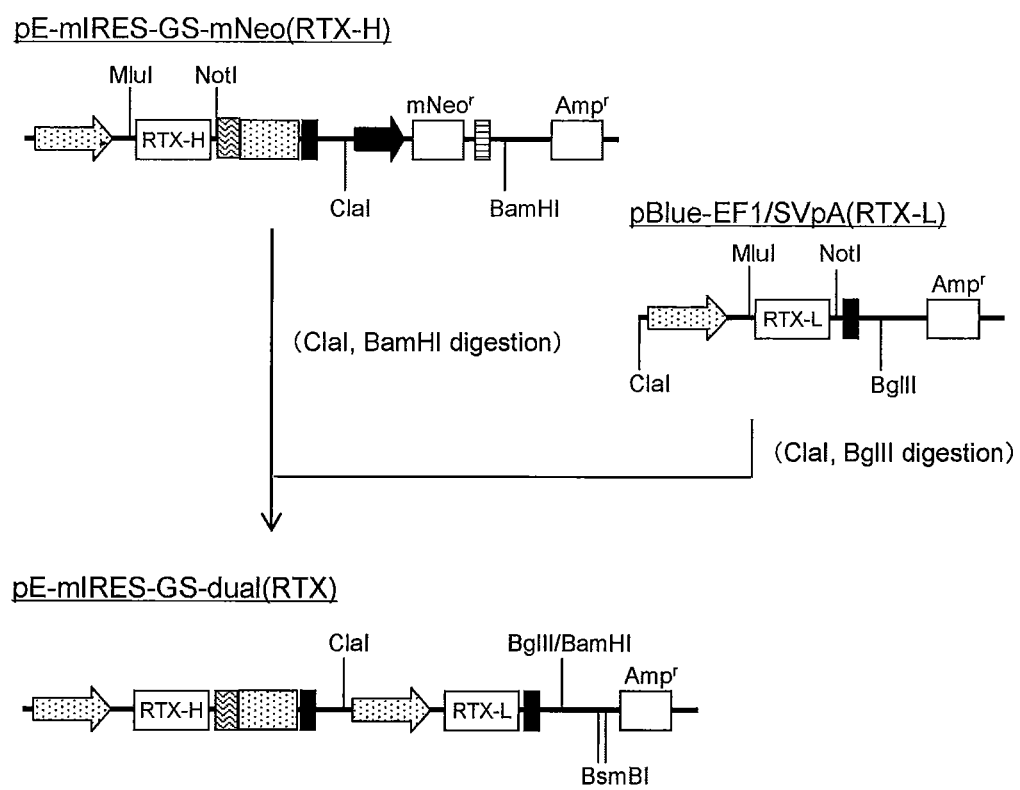
Figures 3, 18:
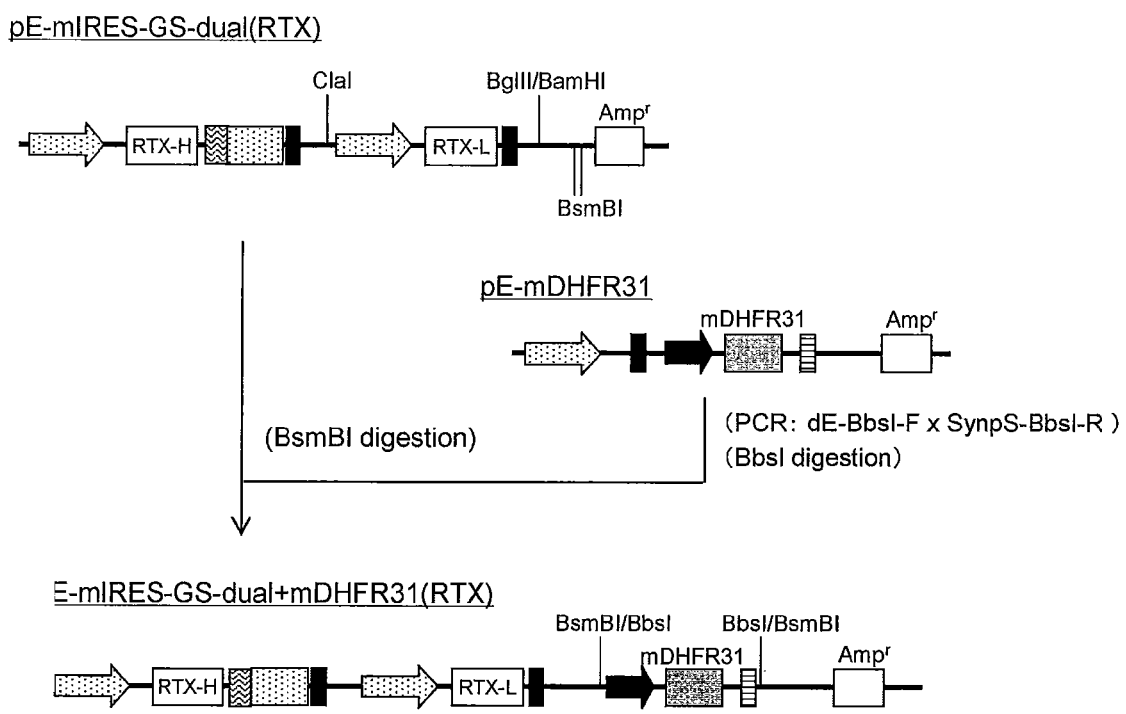

A synthetic DNA containing the DNA set forth as SEQ ID NO:57 which contained the DNA for the light chain of rituximab was digested with restriction enzymes (MluI and NotI), and the DNA fragment thus obtained was inserted into pBlue-EF1/SVpA between its MluI and NotI sites. The product thus obtained was designated pBlue-EF1/SVpA (RTX-L) (FIG. 18-1).

pBlue-EF1/SVpA(RTX-L) was digested with restriction enzymes (ClaI and BglII), and the DNA fragment thus obtained was inserted into pE-mIRES-GS-mNeo(RTX-H) between its ClaI and BamHI sites. The product thus obtained was designated pE-mIRES-GS-dual(RTX) (FIG. 18-2).

Using pE-mDHFR31, as a template, and primer dE-BbsI-F (SEQ ID NO:58) and primer SynpA-BbsI-R (SEQ ID NO:59), PCR was performed to amplify a DNA fragment containing SV40 early promoter (SV40 enhancer/promoter), the mutant-type DHFR (F31W), and the synthetic polyadenylation signal. This DNA fragment was digested with a restriction enzyme (BbsI) and inserted into pE-mIRES-GS-dual(RTX) between its BsmBI sites. The product thus obtained was designated pE-mIRES-GS-dual+mDHFR31 (RTX), a vector for expression of rituximab (FIG. 18-3).

[Production of hTSH Expressing Cells and Rituximab Expressing Cells]

By electroporation (Invitrogen), CHO-K1 cells, which was cells derived from a Chinese hamster ovary cell, were transformed with pE-mIRES-GS-mNeo-dual(hTSH), pE-mIRES-GS-mNeo-dual+mDHFR31(hTSH), pE-mIRES-GS-mNeo-dual(RTX), and pE-mIRES-GS-dual+mDHFR31(RTX), respectively. The cells thus transformed were selective cultured in selective mediums, and hTSH expressing cells and RTX expressing cells were respectively obtained.

In the selective culture of cells that had been transformed with pE-mIRES-GS-mNeo-dual+mDHFR31(TSH) and pE-mIRES-GS-dual+mDHFR31(RTX), the cells were at first cultured in CD Opti CHO medium (Invitrogen) supplemented with methotrexate (Wako), with stepwise increasing the concentration of methotrexate in the medium, and finally in the medium containing 0.5 µM methotrexate, to allow cells exhibiting resistance to methotrexate to grow selectively. Then, the medium was replaced with a CD Opti CHO medium (Invitrogen) supplemented with methionine sulfoximine (Sigma), and the cells were cultured with stepwise increase of the concentration of methionine sulfoximine, and finally in the medium containing 300 µM methionine sulfoximine, to allow cells exhibiting resistance to methionine sulfoximine to grow selectively. The cells thus obtained were treated as bulk cells.

In selective culture of cells transformed with pE-mIRES-GS-mNeo-dual(TSH) and E-mIRES-GS-mNeo-dual(RTX), the cells were cultured in CD Opti CHO medium (Invitrogen) supplemented with methionine sulfoximine and G418, with stepwise increasing the concentration of methotrexate and G418 in the medium, and finally in the medium containing 300 µM methionine sulfoximine and 1 mg/mL G418, to allow cells exhibiting resistance to both of the drugs to grow selectively. The cells thus obtained were treated as bulk cells.

The respective bulk cells obtained by the selective culture described above were seeded to a 96-well plate so that 1-3 cells were to be contained per well, and cultured for about two weeks in CD Opti CHO medium (Invitrogen) until colonies formed. Through measurement of the concentration of hTSH and RTX in the culture supernatant, cells with high expression levels were collected. In doing this, methionine sulfoximine was added to the medium at the concentration of 300 µM. These cloned cells were used in the following experiments as TSH expressing cells and RTX expressing cells.

[Measurement of Expression Levels of hTSH in hTSH Expressing Cells]

The TSH expressing cells obtained through the selective culture were cultured at a cell density of $2 \times 10^5$ cells/mL in 5 mL of CD Opti CHO medium containing 300 µM methionine sulfoximine for 10 days at 37° C., 5% $CO_2$. The culture supernatant was sampled on days 3, 7, and 10 of the culture.

A solution of mouse anti-hTSH-beta monoclonal antibody (Leinco Technologies) was added 100 µL each to a 96-well plate, and the plate was left undisturbed for one hour at room temperature to let the antibody adhere to the plate. The solution was discarded, and after the plate was washed three times with TBS-T solution (Tris: 0.05M, NaCl: 0.138 M, KCl: 0.0027 M, 0.05% Tween20, pH 8.0), 1% BSA/TBS-T solution was added 200 µL each to the plate, and the plate was left undisturbed for one hour at room temperature for blocking. The solution was discarded and after the plate was washed three times with TBS-T solution, the sampled culture supernatant was added to the plate 100 µL each as a test sample, and the plate was left undisturbed for one hour at room temperature. In doing this, as needed, the culture supernatant was diluted with TBS-T solution. Further, a solution prepared by diluting hTSH (Nibsc) to 0.244~62.5 ng/mL with TBS-T solution was added as a standard solution to the plate in the same manner as the test samples, and the plate was left undisturbed. The solution was discarded, and after the plate was washed three times with TBS-T solution, HRP-labeled mouse anti-hTSH-alpha monoclonal antibody (Leinco Technologies) was added 100 μL each to the plate as the secondary antibody, and the plate was left undisturbed for one hour at room temperature. The plate was washed three times with TBS-T solution, and after addition of HRP substrate (Wako), the plate was left undisturbed for 15 minutes at room temperature, and sulfuric acid then was added to stop the reaction. Absorption was measured at 490 nm on a microwell plate reader, and the values for test samples were interposed into the standard curve produced from the measurements of the standard solution to determine the concentration of hTSH contained in the test sample.

[Measurement of Expression Levels of Rituximab in RTX Expression Cells]

The RTX expressing cells obtained through the selective culture were cultured at a cell density of $2 \times 10^5$ cells/mL in 5 mL of CD Opti CHO medium containing 300 μM methionine sulfoximine for 10 days at 37° C., 5% $CO_2$. The culture supernatant was sampled on days 3, 7, and 10 of the culture.

Expression levels of rituximab were measured using Human IgG ELISA Quantitation Set (Bethyl Laboratories). Solution of goat anti-hIgG antibody (Bethyl Laboratories) was added 100 μL each to a 96-well plate, and the plate was left undisturbed for one hour at room temperature to let the antibody adhere to the plate. The solution was discarded, and after the plate was washed three times with TBS-T solution, 1% BSA/TBS-T solution was added 200 μL each, and the plate was left undisturbed for one hour at room temperature for blocking. The solution was discarded, and after the plate was washed three times with TBS-T solution, the sampled culture supernatant was added to the plate 100 μL each as a test sample, and the plate was left undisturbed for one hour at room temperature. In doing this, as needed, the culture supernatant was diluted with TBS-T solution. Further, a solution prepared by diluting rituximab (Chugai Pharmaceutical) to 3.9-500 ng/mL with TBS-T solution was added as a standard solution to the plate in the same manner as the test samples, and the plate was left undisturbed. The solution was discarded, and after the plate was washed three times with TBS-T solution, HRP-labeled goat anti-hIgG antibody (Bethyl Laboratories) was added 100 μL each to the plate as the secondary antibody, and the plate was left undisturbed for one hour at room temperature. The plate was washed three times with TBS-T solution, and after addition of HRP substrate (Wako), the plate was left undisturbed for 15 minutes at room temperature, and sulfuric acid then was added to the plate to stop the reaction. Absorption was measured at 490 nm on a microwell plate reader, and the values for test samples were interposed into the standard curve produced from the measurements of the standard solution to determine the concentration of rituximab contained in the test sample.

[Results (Expression Levels of hTSH in hTSH Expressing Cells)]

With the CHO cells transformed with the human thyroid stimulating hormone (hTSH) expression vector pE-mIRES-GS-mNeo-dual(hTSH), the concentration of hTSH in the medium on day 10 after starting the culture was 22.0 μg/mL for the bulk cells, and 29.2 μg/mL for the cloned cells. On the other hand, with the CHO cells transformed with pE-mIRES-GS-mNeo-dual+mDHFR31(hTSH), an expression vector containing incorporated DHFR gene as the second selection marker, the concentration of hTSH in the medium on day 10 after starting the culture was 35.3 μg/mL for the bulk cells, and 85.2 μg/mL for the cloned cells (Table 1).

Namely, compared with the case of the hTSH expression vector pE-mIRES-GS-mNeo-dual(hTSH) that contains elongation factor 1 promoter(EF-1p), hTSH gene, mutant-type internal ribosome entry site (mIRES), and GS gene as the first selection marker in this order, the CHO cells transformed with pE-mIRES-GS-mNeo-dual+mDHFR31 (hTSH), which was a hTSH expression vector containing additionally incorporated DHFR gene as the second selection marker, exhibited strikingly increased expression levels of hTSH, i.e., about 1.6 times between respective bulk cells, and about 2.9 times between respective cloned cells.

TABLE 1

Expression levels of human thyroid stimulating hormone (hTSH)
(hTSH concentration in medium: μg/mL)

| Names of vectors | | terms of culture (day) | | |
|---|---|---|---|---|
| | | 3 | 7 | 10 |
| pE-mIRES-GS-mNeo-dual (hTSH) | Bulk cells | 7.4 | 15.6 | 22.0 |
| | Cloned cells | 12.2 | 20.6 | 29.2 |
| pE-mIRES-GS-mNeo-dual + mDHFR31 (hTSH) | Bulk cells | 13.5 | 25.4 | 35.3 |
| | Cloned cells | 21.5 | 63.2 | 85.2 |

[Result (Expression Levels of Rituximab in RTX Expression Cells)]

With the CHO cells transformed with the RTX expression vector pE-mIRES-GS-mNeo-dual(RTX), the concentration of rituximab in the medium on day 10 after starting the culture was 188.6 μg/mL for the bulk cells, and 318.9 μg/mL for the cloned cells. On the other hand, with the CHO cells transformed with pE-mIRES-GS-dual+mDHFR31(RTX), an expression vector containing incorporated DHFR gene as the second selection marker, the concentration of rituximab in the medium on day 10 after the start of the culture was 174.1 μg/mL for the bulk cells, and 401.5 μg/mL for the cloned cells (Table 2).

Namely, compared with the case of the RTX expression vector pE-mIRES-GS-mNeo-dual(RTX) that contains elongation factor 1 promoter (EF-1p), rituximab gene, mutant-type internal ribosome entry site (mIRES), and GS gene as the first selection marker in this order, the cells transformed with pE-mIRES-GS-dual+mDHFR31(RTX), an RTX expression vector containing additionally incorporated DHFR gene as the second selection marker, exhibited levels of RTX expression which, while almost the same between respective bulk cells, was found increases about 1.26 times between respective cloned cells.

TABLE 2

Expression levels of rituximab
(Rituximab concentration in medium: μg/mL)

| Names of vectors | | terms of culture (day) | | |
|---|---|---|---|---|
| | | 3 | 7 | 10 |
| pE-mIRES-GS-mNeo-dual (RTX) | Bulk cells | 37.5 | 123.1 | 188.6 |
| | Cloned cells | 81.3 | 198.2 | 318.9 |
| pE-mIRES-GS-dual + mDHFR31 (RTX) | Bulk cells | 37.3 | 84.2 | 174.1 |
| | Cloned cells | 99.6 | 350.6 | 401.5 |

[Results (Summary)]

The above results indicates that an expression vector that contains, downstream of a gene expression regulatory site, an exogenous gene, a mutant-type internal ribosome entry site, and a glutamine synthetase as a first selection marker, incorporated in this order, and an additionally incorporated dihydrofolate reductase gene as a second selection marker, functions as an expression vector that enables expression of the exogenous gene at high levels.

INDUSTRIAL APPLICABILITY

As the present invention enables expression of a recombinant protein at high levels using mammalian cells, it can be utilized to realize a great reduction of cost for production of products containing a recombinant protein, such as ethical drugs containing a recombinant protein.

DESCRIPTION OF SIGNS

1 LacZ promoter
2 mPGK promoter
3 Internal ribosome entry site (EMCV-IRES) derived from wild-type mouse encephalomyocarditis virus, containing a nucleotide sequence set forth as SEQ ID NO:1
3a Internal ribosome entry site (EMCV-mIRES) derived from mutant-type mouse encephalomyocarditis virus, containing a nucleotide sequence set forth as SEQ ID NO:4
4 Polyadenylation region (mPGKpA) of mPGK
5 Nucleotide sequence containing EF-1p and the first intron
6 SV40 late polyadenylation region
7 Region containing SV40 early promoter (SV40 enhancer/promoter)
8 Synthetic polyadenylation region
9 Region containing cytomegalovirus promoter
10 Glutamine synthetase gene

SEQUENCE LISTING FREE TEXT

SEQ ID NO:2: Modified murine encephalomyocarditis virus; n is a, c, g, or t
SEQ ID NO:3: Modified murine encephalomyocarditis virus; n is a, c, g, or t
SEQ ID NO:4: Modified murine encephalomyocarditis virus
SEQ ID NO:6: Modified murine encephalomyocarditis virus
SEQ ID NO:7: Modified murine encephalomyocarditis virus; n is a, c, g, or t
SEQ ID NO:8: Modified murine encephalomyocarditis virus; n is a, c, g, or t
SEQ ID NO:11: Modified *Mus musculus* DHFR
SEQ ID NO:12: Synthetic Construct
SEQ ID NO:13: Primer Hyg-Sfi5', synthetic sequence
SEQ ID NO:14: Primer Hyg-BstX3', synthetic sequence
SEQ ID NO:15: IRES-Hygr-mPGKpA, synthetic sequence
SEQ ID NO:16: Synthetic Construct
SEQ ID NO:17: Primer IRES5', synthetic sequence
SEQ ID NO:18: Primer IRES3', synthetic sequence
SEQ ID NO:19: Primer mPGKP5', synthetic sequence
SEQ ID NO:20: Primer mPGKP3', synthetic sequence
SEQ ID NO:21: mPGKp, synthetic sequence
SEQ ID NO:22: Primer GS5', synthetic sequence
SEQ ID NO:23: Primer GS3', synthetic sequence
SEQ ID NO:24: Primer puro5', synthetic sequence
SEQ ID NO:25: Primer puro3', synthetic sequence
SEQ ID NO:26: Synthetic sequence containing puromycin resistance gene
SEQ ID NO:27: Synthetic Construct
SEQ ID NO:28: Primer SV40polyA5', synthetic sequence
SEQ ID NO:29: Primer SV40polyA3', synthetic sequence
SEQ ID NO:30: Primer mIRES-GS5', synthetic sequence
SEQ ID NO:31: Primer mIRES-GS3', synthetic sequence
SEQ ID NO:32: Primer SV40polyA5'-2, synthetic sequence
SEQ ID NO:33: Primer SV40polyA3'-2, synthetic sequence
SEQ ID NO:34: Primer mNeoA5', synthetic sequence
SEQ ID NO:35: Primer mNeoA3', synthetic sequence
SEQ ID NO:36: Primer mNeoB5', synthetic sequence
SEQ ID NO:37: Primer mNeoB3', synthetic sequence
SEQ ID NO:38: Primer mNeoC5', synthetic sequence
SEQ ID NO:39: Primer mNeoC3', synthetic sequence
SEQ ID NO:40: Primer mNeoD5', synthetic sequence
SEQ ID NO:41: Primer SVpA-Mega-F, synthetic sequence
SEQ ID NO:42: Primer SVpA-BstXI-R, synthetic sequence
SEQ ID NO:43: Primer SVpA-Not-F, synthetic sequence
SEQ ID NO:44: Primer SVpA-BstXI-R, synthetic sequence
SEQ ID NO:45: Synthetic sequence containing Modified DHFR(F31W)
SEQ ID NO:46: Synthetic sequence containing human TSHα
SEQ ID NO:47: Synthetic sequence containing human TSHβ
SEQ ID NO:48: Synthetic sequence containing WAP3'UTR
SEQ ID NO:49: Primer TSHα5', synthetic sequence
SEQ ID NO:50: Primer TSHα3', synthetic sequence
SEQ ID NO:51: Primer TSHβ5', synthetic sequence
SEQ ID NO:52: Primer TSHβ3', synthetic sequence
SEQ ID NO:53: Primer WAP3', synthetic sequence
SEQ ID NO:54: Primer dE-BbsI-F, synthetic sequence
SEQ ID NO:55: Primer SynpA-BbsI-R, synthetic sequence
SEQ ID NO:56: Rituximab heavy chain, synthetic sequence
SEQ ID NO:57: Rituximab light chain, synthetic sequence
SEQ ID NO:58: Primer dE-BbsI-F, synthetic sequence
SEQ ID NO:59: Primer SynpA-BbsI-R, synthetic sequence

SEQUENCE LISTING

GP167-PCT ST25

The invention claimed is:

1. An expression vector for expression of a protein, comprising a gene expression regulatory site (A), and a gene encoding the protein downstream thereof, an internal ribosome entry site further downstream thereof, a gene encoding a glutamine synthetase still further downstream thereof, and additionally a dihydrofolate reductase gene downstream of another gene expression regulatory site (B) in addition to the former,
    wherein the internal ribosome entry site is derived from the 5' untranslated region of mouse encephalomyocarditis virus,
    wherein the internal ribosome entry site is that in which the 2nd or 3rd start codon from the 5' end has been destroyed by introducing one or more mutations into the nucleotide sequence of a wild-type internal ribosome entry site, and
    wherein the internal ribosome entry site comprises the nucleotide sequence set forth as SEQ ID NO:4.

2. The expression vector according to claim 1, wherein the gene expression regulatory site (A) is an elongation factor 1 promoter, and the gene expression regulatory site (B) is an SV40 early promoter.

3. The expression vector according to claim 1, further comprising, either in the region between the gene encoding the protein and the internal ribosome entry site or in the region downstream of the gene encoding the glutamine synthetase, another internal ribosome entry site in addition to the former internal ribosome entry site, and a drug resistance gene downstream thereof.

4. The expression vector according to claim 1, wherein the expression vector, in addition to the gene expression regulatory site (A) and the gene expression regulatory site (B), further comprises another gene expression regulatory site (C) and a drug resistance gene downstream thereof.

5. The expression vector according to claim 3, wherein the drug resistance gene is a neomycin resistance gene.

6. The expression vector according to claim 1, wherein the gene encoding the protein is a human-derived gene.

7. The expression vector according to claim 6, wherein the human-derived gene is selected from the group consisting of the genes encoding lysosomal enzymes, tissue plasminogen activator (t-PA), blood coagulation factors, erythropoietin, interferon, thrombomodulin, thyroid stimulating hormone (TSH), follicle-stimulating hormone, granulocyte colony-stimulating factor (G-CSF), and antibodies.

8. The expression vector according to claim 6, wherein the human-derived gene is a gene encoding a lysosomal enzyme.

9. The expression vector according to claim 8, wherein the lysosomal enzyme is selected from the group consisting of α-galactosidase A, iduronate-2-sulfatase, glucocerebrosidase, galsulfase, α-L-iduronidase, and acid α-glucosidase.

10. The expression vector according to claim 6, wherein the human-derived gene is a gene encoding erythropoietin.

11. An isolated mammalian cell transformed with the expression vector according to claim 1.

12. The isolated mammalian cell according to claim 11, wherein the cell lacks the intrinsic dihydrofolate reductase gene.

13. The isolated mammalian cell according to claim 11, wherein the cell is a CHO cell.

14. A method for production of a transformed cell expressing a gene encoding the protein comprising the steps of:
    (a) introducing the expression vector according to claim 1 into an isolated mammalian cell,
    (b) subjecting the mammalian cell containing the introduced expression vector to a selective culture in the presence of an inhibitor of dihydrofolate reductase, and
    (c) subjecting the cells selected through the selective culture to a further selective culture in the presence of an inhibitor of glutamine synthetase.

15. A method for production of a transformed cell expressing a gene encoding the protein comprising the steps of:
    (a) introducing the expression vector according to claim 3 into an isolated mammalian cell,
    (b) subjecting the mammalian cell containing the introduced expression vector to a selective culture in the presence of an inhibitor of dihydrofolate reductase, and
    (c) subjecting the cells selected through the selective culture to a further selective culture in the presence of an inhibitor of glutamine synthetase,
    further comprising the step of subjecting the mammalian cell containing the introduced expression vector to a selective culture in the presence of a drug corresponding to the drug resistance gene.

16. The expression vector according to claim 4, wherein the drug resistance gene is a neomycin resistance gene.

* * * * *